US012516337B2

(12) United States Patent

Hilfiker et al.

(10) Patent No.: US 12,516,337 B2

(45) Date of Patent: Jan. 6, 2026

(54) MODULATING AMINO ACID CONTENT IN A PLANT

(71) Applicant: PHILIP MORRIS PRODUCTS S.A., Neuchatel (CH)

(72) Inventors: Aurore Hilfiker, Lausanne (CH); Lucien Bovet, La Chaux-de-Fonds (CH)

(73) Assignee: Philip Morris Products S.A., Neuchatel (CH)

( * ) Notice: Subject to any disclaimer, the term of this patent is extended or adjusted under 35 U.S.C. 154(b) by 488 days.

(21) Appl. No.: 17/041,111

(22) PCT Filed: Mar. 27, 2019

(86) PCT No.: PCT/EP2019/057707

§ 371 (c)(1),
(2) Date: Sep. 24, 2020

(87) PCT Pub. No.: WO2019/185703

PCT Pub. Date: Oct. 3, 2019

(65) Prior Publication Data

US 2021/0115461 A1 Apr. 22, 2021

(30) Foreign Application Priority Data

Mar. 28, 2018 (EP) .................................... 18164766

(51) Int. Cl.

*A01H 5/12* (2018.01)
*A01H 1/00* (2006.01)
*A01H 6/82* (2018.01)
*C12N 15/113* (2010.01)
*C12N 15/82* (2006.01)

(52) U.S. Cl.

CPC ......... *C12N 15/8243* (2013.01); *A01H 1/101* (2021.01); *A01H 5/12* (2013.01); *A01H 6/823* (2018.05); *C12N 15/113* (2013.01); *C12Y 206/01001* (2013.01)

(58) Field of Classification Search

None

See application file for complete search history.

(56) References Cited

U.S. PATENT DOCUMENTS

| | | | | |
|---|---|---|---|---|
| 1,327,692 A * | 1/1920 | Beinhart | A24B 3/04 131/300 |
| 2009/0123626 A1 | 5/2009 | Rommens | |
| 2011/0271404 A1* | 11/2011 | Hatzfeld | C12N 15/8243 800/290 |
| 2014/0020694 A1* | 1/2014 | Moldoveanu | A01H 5/12 435/68.1 |
| 2020/0002708 A1* | 1/2020 | Suzuki | C12N 15/8262 |

FOREIGN PATENT DOCUMENTS

| | | |
|---|---|---|
| JP | 2015-530078 | 10/2015 |
| WO | WO 2010/034681 | 4/2010 |
| WO | WO 2014/015228 | 1/2014 |
| WO | WO 2016/009006 | 1/2016 |
| WO | WO 2017/042162 | 1/2016 |

OTHER PUBLICATIONS

Senthil-Kumar et al. (2011). "Caveat of RNAi in Plants: The Off-Target Effect." In: Kodama, H., Komamine, A. (eds) RNAi and Plant Gene Function Analysis. Methods in Molecular Biology, vol. 744. Humana Press. https://doi.org/10.1007/978-1-61779-123-9_2.*

Chen et al., N_GeneSeq Database, Acc. No. BBU47888, CN104152475, Nov. 19, 2014.*

Du et al., N_GeneSeq Database, Acc. No. ATD15677, CN101210251, Jul. 2, 2008.*

International Search Report and Written Opinion for PCT/EP2019/057707 dated Aug. 19, 2019 (26 pages).

Extended European Search Report for Application No. 181647660.0 dated Nov. 7, 2018 (17 pages).

Schoenbeck, et al., "Modification of Aspartate Aminotransferase Activity in Transgenic Medicago Sativa and Lotus Corniculatus Nodules Using Antisense Transgenes", *Plant Physiology*, American Society of Plant Physiologists, vol. 105, No. 1, Jan. 1, 1994.

De La Torre et al., "Deciphering the Role of Aspartate and Prephenate Aminotransferase Activities in Plastid Nitrogen Metabolism", *Plant Physiology*, vol. 164, No. 1, Dec. 2, 2013.

Miesak et al., "Molecular and Physiological Analysis of *Arabidopsis* Mutants Defective in Cytosolic or Chloroplastic Aspartate Aminotransferase", *Plant Physiology*, American Society of Plant Physiologists, vol. 129, No. 2, Jun. 1, 2002.

Database Uniport [online] Apr. 12, 2017, RecName: Full=Aspartate (Continued)

*Primary Examiner* — Phuong T Bui

(74) *Attorney, Agent, or Firm* — Mueting Raasch Group

(57) ABSTRACT

The present invention discloses the polynucleotide sequences of genes encoding aspartate transaminase (AAT) from *Nicotiana tabacum* and the modulation of their expression. There is described a plant cell comprising: (i) a polynucleotide comprising, consisting or consisting essentially of a sequence having at least 80% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15; (ii) a polypeptide encoded by the polynucleotide set forth in (i); (iii) a polypeptide comprising, consisting or consisting essentially of a sequence having at least 95% sequence identity to SEQ ID NO: 6 or SEQ ID No: 8, at least 93% sequence identity to SEQ ID NO: 2 or SEQ ID NO: 10 or SEQ ID No: 12, or at least 94% sequence identity to SEQ ID NO: 4 or SEQ ID NO: 14 or SEQ ID NO: 16; or (iv) a construct, vector or expression vector comprising the isolated polynucleotide set forth in (i), wherein said plant cell comprises at least one modification which modulates the expression or activity of the polynucleotide or the polypeptide as compared to a control plant cell in which the expression or activity of the polynucleotide or polypeptide has not been modified.

7 Claims, 4 Drawing Sheets

Specification includes a Sequence Listing.

(56) References Cited

OTHER PUBLICATIONS minotransferase {ECO:0000256, RuleBase: RU000480]; XP002783109, retrieved from EBI accession No. A0A1S4D3Y8; database accession No. AOA1S4D3Y8.
Database Uniport [online] Apr. 12, 2017, RecName: Full=Aspartate Aminotransferase {ECO:0000256, RuleBase: RU000480]; XP002783110, retrieved from EBI accession No. A0A1S3Y9E9; database accession No. A0A1S3Y9E9.
Database Uniport [online] May 10, 2017, RecName: Full=Aspartate Aminotransferase {ECO:0000256, RuleBase: RU000480]; XP002785986, retrieved from EBI accession No. A0A1U7YVS5; database accession No. A0A1U7YVS5.
Database Uniport [online] Apr. 12, 2017, RecName: Full=Aspartate Aminotransferase {ECO:0000256, RuleBase: RU000480]; XP002785987, retrieved from EBI accession No. A0A1S3ZLW1; database accession No. A0A1S3ZLW1.
Database Uniport [online] Apr. 12, 2017, RecName: Full=Aspartate Aminotransferase {ECO:0000256, RuleBase: RU000480]; XP002785988, retrieved from EBI accession No. A0A1S4AT92; database accession No. A0A1S4AT92.
Avila-Ospina L, Marmagne A, Talbotec T, Krupinska K, Masclaux-Daubresse C (2015) The identification of new cytosolic glutamine synthetase and asparagine synthetase genes in barley (*Hordeum vulgare* L.), and their expression during leaf senescence. J Exp Bot 66(7): 2013-2026. doi: 10.1093/jxb/ervo03.
Baud S, Vaultier MN, Rochat C (2004) Structure and expression profile of the sucrose synthase multigene family in Arabidopsis. J Exp Bot 55(396)397-409 doi:10.1093/jxb/erho47.
Bieniawska Z, Barratt DHP, Garlick AP, Thole V, Kruger NJ, Martin C, Zrenner R, M. Smith AM (2007) Analysis of the sucrose synthase gene family in Arabidopsis. Plant J 49:810-828. doi:10.1111/j.1365-313X.2006.03011.x.
Chen D, Wang S, Xiong B, Cao B, Deng X (2015) Carbon/Nitrogen imbalance associated with drought-induced leaf senescence in sorghum bicolor, PLOS One 10(8):e0137026. doi: 10.1371/journal.pone.0137026.
Cheng M, Hu T, Layton J, Liu CN, Fry JE (2003) Desiccation of plant tissues post-Agrobacterium infection enhances T-DNA delivery and increases stable transformation efficiency in wheat. In Vitro Cellular & Developmental Biology—Plant 39: 595-604.
Christ B, Egert A, Süssenbacher I, Kräutler B, Bartels D, Peters S, Hörtensteiner S (2014) Water deficit induces chlorophyll degradation via the 'PAO/phyllobilin' pathway in leaves of homoio—(*Craterostigma pumilum*) and poikilochlorophyllous (*Xerophyta viscosa*) resurrection plants. Plant Cell Environ 37(11):2521-2531. doi: 10.1111/pce.12308.
De la Torre F, El-Azaz J, Ávila C, Cánovas FM (2014) Deciphering the role of aspartate and prephenate aminotransferase activities in plastid nitrogen metabolism Plant Physiol 164(1):92-104. doi: 10.1104/pp.113.232462.
Edwards KD, Ferandez-Poro N, Drake-Stowe K, Humphry M, Evans AD, Bombarely A, Mueller LA (2017) A reference genome for Nicotiana tabacum enables map-based cloning of homeologous loci implicated in nitrogen utilization efficiency. BCM Genomics 18:448. doi: 10.1186/s12864-017-3791-6.
Gepstein S, Thimann KV (1980) Changes in the abscisic acid content of oat leaves during senescence. Proc Natl Acad Sci USA 77(4): 2050-2053.
Gaufichon L, Rothstein SJ, Suzuki A (2016) Asparagine metabolic pathways in Arabidopsis. Plant Cell Physiol 57(4): 675-689. doi: 10.1093/pcp/pcv184.
Jin Y, Ni D-A, Ruan Y-L (2009) Posttranslational elevation of cell wall invertase activity by silencing its inhibitor in tomato delays leaf senescence and increases seed weight and fruit hexose level. Plant Cell 21(7):2072-2089. doi:10.1105/tpc.108.063719.
Leffingwell JC (1999) Leaf chemistry. In: Tobacco: Production, Chemistry, And Technology. Davis DL, Nieslson MT (eds), Blackwell Science.
Legg PD, Chaplin JF, Williamson RE (1997). Genetic diversity in Burley and flue-cured tobacco. Crop Sci 17:943-7. doi:10.2135/cropsci1977.0011183X001700060032x.
Lewis RS, Bowen SW, Keogh MR and Dewey RE. (2010) Three nicotine demethylase genes mediate nornicotine biosynthesis in *Nicotiana tabacum* L.: functional characterization of the CYP82E10 gene. Phytochemistry 71: 17-18.
Li L, Zhao J, Zhao Y,Lu X, Zhou Z, Zhao C, Xu G (2016) Comprehensive investigation of tobacco leaves during natural early senescence via multi-platform metabolomics analyses. Sci Rep 6: 37976. doi: 10.1038/srep37976.
Masclaux-Daubresse C, Carrayol E, Valadier MH (2005) The two nitrogen mobilisation- and senescence-associated GS1 and GDH genes are controlled by C and N metabolites. Planta 221(4): 580-588. doi: 10.1007/s00425-004-1468-2.
Masclaux-Daubresse C, Reisdorf-Cren M, Pageau K, Lelandais M, Grandjean O, Kronenberger J, Valadier MH, Feraud M, Jouglet T and Suzuki A. (2006) Glutamine synthetase-glutamate synthase pathway and glutamate dehydrogenase play distinct roles in the sink-source nitrogen cycle in tobacco. Plant Physiol. 140:444-56.
Olvera-Carrillo Y, Campos F, Reyes JL, Garciarrubio A, Covarrubias AA (2010) Functional analysis of the group 4 late embryogenesis abundant proteins reveals their relevance in the adaptive response during water deficit in *Arabidopsis*. Plant Physiol 154(1):373-390. doi:10.1104/pp.110.158964.
Patro L, Mohapatra PK, Biswal UC, Biswal B (2014) Dehydration induced loss of photosynthesis in *Arabidopsis* leaves during senescence is accompanied by the reversible enhancement in the activity of cell wall B-glucosidase. J Photochem Photobiol B 137:49-54. doi: 10.1016/j.jphotobiol.2014.03.018.
Pourtau N, Jennings R, Pelzer E, Pallas J, Wingler A (2006) Effect of sugar-induced senescence on gene expression and implications for the regulation of senescence in Arabidopsis. Planta 224(3):556-68. doi:10.1007/s00425-006-0243.
Shi H, Wang B, Yang P, Li Y, Miao F (2016) Differences in sugar accumulation and mobilization between sequential and non-sequential senescence wheat cultivars under natural and drought conditions. PLoS One 11(11): e0166155. doi:10.1371/journal.pone.0166155.
Sierro N, Battey JND, Ouadi S, Bakaher N, Bovet L, Willig A, Goepfert S, Peitsch MC, Ivanov NV (2014) The tobacco genome sequence and its comparison with those of tomato and potato. Nature Com 5, 3833. doi.org/10.1038/ncomms4833.
Sonnewald U, Brauer M, von Schaewen A, Stitt M, Willmitzer L (1991) Transgenic tobacco plants expressing yeast-derived invertase in either the cytosol, vacuole or apoplast: a powerful tool for studying sucrose metabolism and sink/source interactions. Plant J 1(1):95-106. doi: 10.1111/j.1365-313X.1991.00095.x.
Stitt M, Wilke I, Feil R, Heldt HW (1988) Coarse control of sucrose-phosphate synthase in leaves: Alterations of the kinetic properties in response to the rate of photosynthesis and the accumulation of sucrose. Planta 174(2):217-30. doi:10.1007/BF00394774.
Uzelac B, Janošević D, Simonović A, Motyka V, Dobrev PI, Budimir S (2016) Characterization of natural leaf senescence in tobacco (Nicotiana tabacum) plants grown in vitro. Protoplasma (2): 259-275. doi: 10.1007/s00709-015-0802-9.
Wang W, Hao Q, Tian F, Li Q and Wang W. (2016) Cytokinin-Regulated Sucrose Metabolism in Stay-Green Wheat Phenotype. PLoS One. 11: e0161351. doi: 10.1371/journal.pone.0161351. eCollection 2016.
Wingler A, Masclaux-Daubresse C, Fischer AM (2009) Sugars, senescence, and ageing in plants and heterotrophic organisms. J Exp Bot 60(4): 1063-1066. doi: 10.1093/jxb/erpo67.
Yang J, Zhang J, Wang Z, Zhu Q, Liu L (2002) Abscisic acid and cytokinins in the root exudates and leaves and their relationship to senescence and remobilization of carbon reserves in rice subjected to water stress during grain filling. Planta 215(4):645-52. doi:10.1007/s00425-002-0789-2.
Zhang K, Xia X, Zhang Y, Gan S-S (2012) An ABA-regulated and Golgi-localized protein phosphatase controls water loss during leaf senescence in Arabidopsis. Plant J 69(4): 667-678. doi: 10.1111/j.1365-313X.2011.04821.

(56) References Cited

OTHER PUBLICATIONS

Diaz-Mendoza M, Velasco-Arroyo B, Santamaria ME, González-Melendi P, Martinez M, Diaz I, (2016) Plant senescence and proteolysis: two processes with one destiny. Genet Mol Biol 39(3): 329-338. doi: 10.1590/1678-4685-GMB-2016-0015.

Office Action issued in Japan for Application No. 2020-552367 dated Jan. 24, 2023 (5 pages). English translation included.

* cited by examiner

SEQUENCE LISTING

<160> NUMBER OF SEQ ID NOS: 17

<210> SEQ ID NO 1
<211> LENGTH: 6933
<212> TYPE: DNA
<213> ORGANISM: Nicotiana tabacum

<400> SEQUENCE: 1

```
atgaacatgt cacaacaatc accgtcaccg tccgctgacc ggaggttgag tgttctggcg     60

agacaccttg aactgtcgtc ctccgccacc gtcgaatcct ctatcgtcgc tgctcctacc    120

tctggaaatg ctggaaccaa ctctgtcttc tctcacatcg ttcgcgctcc cgaagatcct    180

attctcggcg taactctctc tctctctctc tctctctctc ttcatccaca cacacacgca    240

ctcactcaca taacatatta agtatatgcg tgctcaaatg ttctgtatgt attcatttgt    300

tccgtatcaa atgttctctt gttataagct gaattttaga ggaattgtag tgctatttgc    360

taatcgaaag agcttgatac tcattctctt cctattgaat taaatattcc tttttttctta    420

tggatgatga atttaagact ttttttagt ccgatcacta cgaaatttcg atttcaagtt    480

gatagaagtg aaaaatgatg ggttaacat atcaattgag cgaataaaaa gagaaattcg    540

tgtgttgata tcttcaaaag tgtatttaaa tgtagagata tattgtgatt tagtttctgt    600

tattatcttt gtcttttttc tattgaaatt tgaatattat ttgttgaagt cttcgtgaca    660

tatcttggtg ttatgttttg gttattaggt cactattgct tacaataaag atagtagccc    720

catgaagttg aatttgggag ttggtgcata tcgcacagag gtgatcatcc tttttggatt    780

ttgtatttgc gctattatgg tcaatggagc actattatca gttgctggat aatcatcctt    840

tttgatattt ccttgattga aatctaaaaa cacgaataaa aagatattta ctgatggatc    900

tgtgttttgg tttcttcaga ttgacgcatt tctgttaatt gaaaagaatt gtgattgttt    960

tggtgattgt ggtgttattt tagcttcata cagttaatcc gacgccgtag tgtactagtg   1020

tttggctgat gtgctgccaa gagataatgt ttaagattat ggtttgccat aattgataaa   1080

atttaatatt aaaagtactt ggctggatgt tctgcgtttg cataacttgt aatgcatatg   1140

aaaaagttac ctttgatttt cataattagt gagaaaactc aagtagcttc cgcattcctg   1200

tcattgcact atcaaacaca ttaaacggtt tccgacatat ctacctagtt tggaacttca   1260

tgatttctat ttttcacacc ttgtaataaa tgataattct tggatctgtg gtgtctttgt   1320

tcaaaagatc acagagaaga ttgcatttat tttttgtagt ctagttggct cagagtctgt   1380

caaacacaac ttgttacatc gcattttacc tgttagttaa gaaacttggg tcatcaacaa   1440

atttgtcatg aggtggttat ttcttggggc tttgtgaatt gctctcagca atctgctagc   1500

tttcttatgt ggactcaaaa caatgaagct cttgagttga tgtgttgatt tttcaatcag   1560

agtaaaacaa gttctatatt tggctgtgag agtaaagtgg gagctattaa aattcctagc   1620

tgaatttatg tttcttaata tcttaaatcc ttaaaggtag agggagagga aggaggttta   1680

ttgatgaagg gctagtagtt gtgtatactt agttcttttt caaatttcat aagtatctct   1740

tgatggtttt tctcgctgac tgttgaatat ggggctccac agtttgtgtt gctatattga   1800

aatgtttcag ctaataaaac taacgtgttt ctttttcttt ctccctttttt tggggttatc   1860

aggaaggaaa acctcttgtt ttgaatgttg taagacaagc agagcagcta ctagtaaatg   1920

acaggtactt gcattgccat ttcatggagt atgaataaaa tgtttcctta attctatgtg   1980

attaaacttc aagatttctg caggtctcgc gttaaagagt acctatctat tacgggactg   2040

gcagacttca ataaattgag tgctaagctg atacttggcg ccgacaggta taaaagttcc   2100
```

```
tgttctctgt atagtgttgc cgataagata tgcagggaga taaagcatgt attttcctgt   2160
tgcataggat gatatcttca gataataagg ctccattcca agtgtttgat ggcttggtag   2220
atctttgtga agcatctatt aacatttggt cacatttttt taaaaccaac ttcccatccc   2280
atccatgcca ttccacgtgt cagttattca tgaaaatgct gttcacttgc atacatgtta   2340
ctgccgttgt gttgatttcc tcaactctac tcataatttc tctgtgtggt cgcattctgg   2400
tgatctgatt tatctgataa tatctgtaca tgttttgaaa tttgggtagt gtctctttga   2460
ttagcgtgta aagcaagcaa ctcttgatgc gtgtgatcaa gtgtattgct gtctagagct   2520
gacagatgtt aaatttatct tatgcgtttc caagatcttc cagatgttct atgtaatctt   2580
tttaggccag cttaaacttt gacttgcttc atatacattt atgttaaagg agagttgtta   2640
atatacttca atttttcaca tttttaattc ctctttttac ctgtggtcct cacgagctct   2700
tactttcttt gcttggtaca gccccgctat tcaagagaac agagtaacaa ctgtgcagtg   2760
cttgtctggc acaggctcat tgagggttgg agctgaattt ttggctcgac attatcatca   2820
agtaaactgc tacatcttcc taacctacct ttcattttcc ttcgttttct tagccttcgt   2880
gggtaaacaa tcttcaaagt tgaattaacc ttgatgtaac cattcctgca gcgcacaatt   2940
tatattcccc aaccaacatg gggaaaccac ccaaaagttt tcactttagc tggattatcg   3000
gtaaagagtt accgctacta tgatccagca actcgtggac tcaattttca aggtatgaaa   3060
cacttcccta caatataatg atgtaacagg atattgtccc attagatatc tatggctatg   3120
ctgtttacta ttactctctt ccaggatgat ggatgttctt ttagtcttat tctggtattt   3180
gattacaaat tatcacaagt ctgaatcaag ttgtggatgg atggtttcac ttgtttgatt   3240
gcattgtaat ccagcaaact tgtaaagtca tcgtcatcta tgctttttct ttatacettt   3300
ttctgcgagg aaataagcga agagagatgg agatataact tgataataat ggaatgcaac   3360
aaacgcctaa tttaacatat tagggaccaa ctaacgtcta catttgacat tagctcttaa   3420
cattttgact ttttaatacc ttaccaaaaa taaaaaagat tgacattcta atgtcgcacg   3480
gaaccaaagg tgggaatagc tgataacata gaaaagtaac caaacaagtc ctggaatctt   3540
gtcaaaaaag aaattcagtt gtcgaaatgt tcttgaaaaa agttactgca accgcaatgg   3600
tcggaagaat aggaggaaga aattcaataa tgcgggtcaa atagaggagg tgccactaaa   3660
aggccattgg agaggggccg ggaaacacca tctgaaagag gtacagtggt accagaagga   3720
ttatcgaatg ctgatgcata gaaacgagtc agagattgaa acagtcactg gaaagaggtt   3780
tgatgttgtg acagcagtca caataaagaa aagtggtgca atcagaatga tcactggaaa   3840
ggctagaatt gtagaactat cataagaaag tgaattgtgg agggaaatct ctgtgaaaag   3900
acaaaatcta tttaggtcca caagatcata gaggctctaa tgccatgtga gaaactgaga   3960
gagtggacgg aaataaatag attacttgat aaaatacaat ccatacgttt aaatccgaat   4020
gactaacttt aattttaaca caacttttac atctaaaagt atgacacgtg acattctaac   4080
ctttcgtgct tgtgttcaca actttgcata tcgccgactt gtttacaaga actttctttt   4140
tcgtacatga caggtttgtt ggaagacctt ggatctgctc catcgggagc ggtagtgcta   4200
cttcacgctt gtgcccataa ccccactggt gttgatccaa ccattgatca gtgggagcaa   4260
attaggagat tgatgagatc aagaggattg ttgcccttct ttgatagtgc atatcaggta   4320
agagatcatc aacagatgtg cagagcactt tggctgttgg agttgttgct gtgtgagcat   4380
ttaaaagtga tgtggtttgt tcagtatatg tcaattaacc ttgatattca aactttgata   4440
```

```
ttctagggct ttgccagtgg aagcctagat acagatgcac agtctgttcg catgtttgtg   4500
gcagatggag gtgaagtact tgttgctcaa agttatgcaa agaatatggg gctttatggt   4560
gaacgtgttg gagctctaag cattgtacgt cttaaaggac aatggacaac tgtgccttat   4620
ttctgaaaat ttatatctcc agttggtcat ttgttgcatt acctttattt ttctcagatt   4680
gattctcatg atgcataaac tgtcttactg ttttcatagt ggccttcttt tgtgatgtta   4740
aaatttggta gttatgaact gtttaaagct tatatagctt acttccaaat aaataactgt   4800
gagccttgga catcacatat aaattatttt atatcacgga ttcgagccgt ggaaacaacc   4860
tcttgcagaa atgtagggta aggttgcgta taatagaccc ttgtcatccg gcccttcccc   4920
ggacccctgc gcatagcggg agcttagtgc aacgggttgc cttttttca tcctgaggca   4980
taaaaagttt gtaatttctc aagaatgaat aaagagcctg ttataacagg caatttgcat   5040
atcatatggt gttgtttgtc gcacagtgat gacatattta tcacacaaat gaaagaaaaa   5100
tgaaggatat agttctgaac cctcagttaa actctgctga cagttataat tcttcaaatt   5160
ttctcaaatc tgtaggtctg caggaatgct gatgtggcga gcagagttga gagccagctg   5220
aagttggtga ttaggccaat gtattccaat ccgcccatcc atggtgcgtc aatagttgcc   5280
acaatcctta aagacaggta atatatcaac catcaggaaa ttgcttcttg ggaccctaaa   5340
aagccatttc ctttctttct atatgataga atccagtgta tgttcaaaaa ttatgtttag   5400
tcattgttct gcaaaataaa tcactaattt tctgcagaaa catgtaccgt gaatggaccc   5460
ttgagctgaa agcaatggct gatagaatca tcagaatgcg tcagcaatta tttgatgctt   5520
tacgtgctag aggtaaattt gctgcattat tttcacgtat gtgtgctctt attacatgtt   5580
tcttgttgca tcgacttcgg atatttttct catttttgat aatttcggtt caagtgtcat   5640
tataaatgct acatgttcgt ggcatatact tctacccata aaatatgctg caacttgttc   5700
cagctcattt gtctagataa tttatcaaaa ggaccaatct tcaccagctg actctcctga   5760
atgaaagctt aatttaggaa aaagattaag caaacaaaac atggaattcg acaaattcaa   5820
acatttctcc aaatcttaat agatctcgat cctccttagt gctttcatca acttcttagg   5880
taattcacct cttaactttg gctctgactg ggttctctac ctttggaaaa ccatccccaa   5940
agatgtccct tgcacgatcc ttttggggac atgaactgtt ggatcaggca agaaactatc   6000
ccccaataaa gaaaaattgt tggatcagat tttttcctga taggttgcat tctttcagca   6060
ttccccttaa agtttgtgat ttggacgttg tcctcatttt ggtataaaaa atgtcattgg   6120
aaactttcca ttttggcaca tcaggtgtta gaatcatcat gtcttcataa attggctata   6180
gacaaagtct catgtcgtca gctcctttct tcagtatcag gcattcttta atcaatgtaa   6240
gtgtcgagca ttgcatgagt aggatactta tttctattta catgaattga tgggcaagtc   6300
gggcattttt tagtcgactt aaaggtcaag cattgcatgt ataagatatc tatttctgtt   6360
gaattcaatt gattggcagg tacacctggt gactggagtc acattatcaa gcagattgga   6420
atgtttactt tcacgggact taactcagag caagttgcct tcatgaccaa agagtaccac   6480
atctacatga catcagatgg gtaatatgtc atttctcagc aaaaagtact gtatatcata   6540
tcagactacc atgtctcctc cacatctgat atgtgatttt attacctcgt aagaatttct   6600
accctcggat ggtaaaacag aaagagggaa gggagttaaa atcttttcag ccatcagtta   6660
gttcttttct tgcagtattc ttgctacctt agctttgatg aacgctaaga gaaatgtggc   6720
tgtattaatg aacatttcta gagcatggtt ctttctaagt ttgtatttaa ttgtggcaac   6780
ttcaattaag cttgggatat cagataatcc caaagccttt gacatacatc acatatttca   6840
```

ttttgcagac gcatcagtat ggcaggtctg agctccagga cagttccaca tctagcagat 6900
gccatacatg ctgctgtcgc tcgggctcgt tga 6933

<210> SEQ ID NO 2
<211> LENGTH: 450
<212> TYPE: PRT
<213> ORGANISM: Nicotiana tabacum

<400> SEQUENCE: 2

Met Asn Met Ser Gln Gln Ser Pro Ser Pro Ser Ala Asp Arg Arg Leu
1 5 10 15

Ser Val Leu Ala Arg His Leu Glu Leu Ser Ser Ser Ala Thr Val Glu
20 25 30

Ser Ser Ile Val Ala Ala Pro Thr Ser Gly Asn Ala Gly Thr Asn Ser
35 40 45

Val Phe Ser His Ile Val Arg Ala Pro Glu Asp Pro Ile Leu Gly Val
50 55 60

Thr Ile Ala Tyr Asn Lys Asp Ser Ser Pro Met Lys Leu Asn Leu Gly
65 70 75 80

Val Gly Ala Tyr Arg Thr Glu Glu Gly Lys Pro Leu Val Leu Asn Val
85 90 95

Val Arg Gln Ala Glu Gln Leu Leu Val Asn Asp Arg Ser Arg Val Lys
100 105 110

Glu Tyr Leu Ser Ile Thr Gly Leu Ala Asp Phe Asn Lys Leu Ser Ala
115 120 125

Lys Leu Ile Leu Gly Ala Asp Ser Pro Ala Ile Gln Glu Asn Arg Val
130 135 140

Thr Thr Val Gln Cys Leu Ser Gly Thr Gly Ser Leu Arg Val Gly Ala
145 150 155 160

Glu Phe Leu Ala Arg His Tyr His Gln Arg Thr Ile Tyr Ile Pro Gln
165 170 175

Pro Thr Trp Gly Asn His Pro Lys Val Phe Thr Leu Ala Gly Leu Ser
180 185 190

Val Lys Ser Tyr Arg Tyr Tyr Asp Pro Ala Thr Arg Gly Leu Asn Phe
195 200 205

Gln Gly Leu Leu Glu Asp Leu Gly Ser Ala Pro Ser Gly Ala Val Val
210 215 220

Leu Leu His Ala Cys Ala His Asn Pro Thr Gly Val Asp Pro Thr Ile
225 230 235 240

Asp Gln Trp Glu Gln Ile Arg Arg Leu Met Arg Ser Arg Gly Leu Leu
245 250 255

Pro Phe Phe Asp Ser Ala Tyr Gln Gly Phe Ala Ser Gly Ser Leu Asp
260 265 270

Thr Asp Ala Gln Ser Val Arg Met Phe Val Ala Asp Gly Gly Glu Val
275 280 285

Leu Val Ala Gln Ser Tyr Ala Lys Asn Met Gly Leu Tyr Gly Glu Arg
290 295 300

Val Gly Ala Leu Ser Ile Val Cys Arg Asn Ala Asp Val Ala Ser Arg
305 310 315 320

Val Glu Ser Gln Leu Lys Leu Val Ile Arg Pro Met Tyr Ser Asn Pro
325 330 335

Pro Ile His Gly Ala Ser Ile Val Ala Thr Ile Leu Lys Asp Arg Asn
340 345 350

```
Met Tyr Arg Glu Trp Thr Leu Glu Leu Lys Ala Met Ala Asp Arg Ile
        355                 360                 365

Ile Arg Met Arg Gln Gln Leu Phe Asp Ala Leu Arg Ala Arg Gly Thr
    370                 375                 380

Pro Gly Asp Trp Ser His Ile Ile Lys Gln Ile Gly Met Phe Thr Phe
385                 390                 395                 400

Thr Gly Leu Asn Ser Glu Gln Val Ala Phe Met Thr Lys Glu Tyr His
                405                 410                 415

Ile Tyr Met Thr Ser Asp Gly Arg Ile Ser Met Ala Gly Leu Ser Ser
            420                 425                 430

Arg Thr Val Pro His Leu Ala Asp Ala Ile His Ala Ala Val Ala Arg
        435                 440                 445

Ala Arg
    450


<210> SEQ ID NO 3
<211> LENGTH: 6935
<212> TYPE: DNA
<213> ORGANISM: Nicotiana tabacum

<400> SEQUENCE: 3

atgaacatgt cacaacaatc accgtccgct gaccggaggt tgagtgtttt ggcgaggcac     60

cttgaaccgt cgtcctccgc caccgtcgaa acctccatcg tcgctgctcc tacctctgga    120

aatgctggaa ccaactctgt cttctctcac atcgttcgtg ctcccgaaga tcctattctc    180

ggggtaactt tctctctctc tctctctctc tctcttcatc cacacgcact cactcacata    240

acatatgtat aagtatttaa gtatatgcgt gctcaaatgt tctgtatata ttcatttgtt    300

ccgtatcaaa tgttctcttg ttataagctg aattttagag gaattgtagt gttatttgct    360

aatcgcaaga gcttgcatac tcattctctt cgtattgaat taaatattcc tttttttctta    420

tggatgacga atttaagcag ttttttgagt ccgatcacta cgaaatttcg atttcaagtt    480

gatagaagtg aaaaatgatg gtgtttacat attaattgag cgaataaaaa gagaaattcg    540

agtgttgata tcttcaaaaa tgttgttaaa tgtagagata tactgtgatt tagtttctgt    600

tataatcttt gcctttttttc ttttgaaatt tgaatattgt ttgttgaagt cttcgtgaca    660

tattggtgtt atgttttggt tattaggtta ctattgcata caataaagat agcagcccca    720

tgaagttgaa tttgggagtt ggtgcatatc gcacagaggt gatcatcctt tttggctttt    780

gtatttgcgc tattatcgtc gatggagcac tattatcagt agctggataa tcatcctttt    840

tgatatttcc ttgattgaaa tccaaaaaca cgaataaaaa gaaatttact gatggatctg    900

tgttttggtt tcttcagatt tacgcatttc tgttaattga aaaaatatta tgattgtctt    960

ggtgattgtg gtgttgtttt ggcttcatat agttaatccg acgccgtagt gtactaatgt   1020

ttggctgatg tgctgccaag agaaatgttt aagattatgg tctgccataa ctgataaaat   1080

ttaatattaa aagtacttgg ctggatgttc tgcgtttgca taacttgtaa cgcatatgaa   1140

aaaattacct ttgattttca taattagtga gaaaattaag tagcttccgc attcctgtca   1200

ttgcactatc aaacacatac ggtttatgat atatctacct agtttggaac tttgtgattt   1260

ctatttttca caccttgtaa taaatgataa ttcttggatc tgtggtgtct ttgttcaaaa   1320

gatcacagag aagattgcac ttatgttttg tagtctagtt ggctcagact ctgtcaaaca   1380

caacttgtta catcgcattt tacctgttag ttaagaaact tgggtcatca acaaatttgt   1440

catgaggtgg ttatttcttg ggttttgtg aattgctctc agcaatctgc tagctttctt   1500
```

```
atgtggactc aaaacaatga atctcttgag ttgatgtgtt gatttttcaa tcgagtaaaa   1560
caagttctat atttggctgt gagagtaaag tgggagctat taaaattcct agctgaattt   1620
atgtttctta atatcttaaa tccttaaagg tagagggaga ggaaggaggc ttattgatga   1680
aggactagta gttgtgtata cttagttctt tctcaaattt cataagaatc tcttgagggt   1740
ttttctcgct gactgttgaa tatggggctc cacagtttgt gttgctatat tgaaatgttt   1800
cagctaataa tactaacgtg tttctttttc tttctccctt ttgtggggtt atcaggaagg   1860
aaaaccgctt gttttgaatg ttgtaagaca agcagagcag ctactagtaa atgacaggta   1920
cttgtgttgc catttcatgg agtatgaata aaatgtttcc ttaattctat gtgattaaac   1980
ttcaagattt ctgcaggtct cgcgttaaag agtacctatc tattactgga ctggcagact   2040
tcaataaatt gagtgctaag ctgatacttg gtgccgacag gtatacaagt tcctgttctc   2100
tgtatagtgt tgctgataag atatgcaggg agataaagca tgtattttcc tgttgcatag   2160
gatgatatct tccgataata aggctccgtt ccaagtgttt gatggcttgg tagatctttg   2220
tgaagcatct attaacattt gctcacgttt ttttaaaacc aacttcccat cccatccatg   2280
ccattccacg tgtcagttat tcatgaaaat gctgttcact tgcatacatg ttactgccgt   2340
agtgttggtt tctctcaact ctactcataa tttctgtgtg gtcgcattct ggtgatctga   2400
tttatgtgat aatatctgta catgttgttt tgaaatttgg gtagtgtctc tttgattagc   2460
gtgtaaagca ggcaactctt gatgcatgtg gtgaagtgta tgattgctgt ctagagctgt   2520
cagatgttaa atttatctta tgcgtttgca agatcttcca gatgttctat gtaatctttt   2580
taggccagct taaactttga cttgcttcat atacatttat gttaaaggag agttgttaat   2640
atacttcaat tttcacattt ttaattcctc ttttacctgt ggtccttacg agctcttact   2700
ttctttgctt ggtacagccc tgctattcaa gagaacagag taacaactgt gcagtgcttg   2760
tctggcacag gctcattgag ggttggagct gaatttttgg ctcgacatta tcatcaagta   2820
aactgctacg tcttcttaac ctacctttca ctctccttcg ttttcttagc cttcgtgggt   2880
aaacaatctt caaagttgaa ttgaccttga tgtaaccatt cctgcagcgc actatttata   2940
ttccccaacc aacatgggga aaccacccaa aagttttcac tttagctggg ttatcagtaa   3000
agagttaccg ctactatgat ccagcaactc gtggactcaa ttttcaaggt atgaaacact   3060
tcccttcaat ataatgatgt aacgggatat tgtcccatta gatatctatg gccatgctgt   3120
ttcctattac tctcttccag gatgatggat gttcttttag tcttattctg gtatttgatt   3180
acaaattatc acaagtctga atcaagttgt ggatagatgg tttcacttga ttgattgcat   3240
tgtaatccag caaacttgta aatccgtcat catctatgct tttctttat acctttttc    3300
tgcgaggaaa taagagcaga gagatggaga tataacttga taataatgga atgcaacaaa   3360
cgcctaattt aacatattag ggaccaacta acatcagcat ttgacattag ctcttaacat   3420
tttgactttt taacacctta tcaaaaaaaa gaaggaaaaa gattgacatt ctaatgtcgc   3480
acggaaccaa aggtgggaat agctgataac atagaaaagt aaccaaacaa gtcctggaat   3540
cttgtcaaaa aaaaattcag ttgccaaaat gttcttggaa aaaattactg caaccacaat   3600
ggtcggaaga ataggaggaa gaaattcaat aatgcgggtc aaatagagga ggtgccacta   3660
aaaggccatt ggagaggggc cgggaaacac catctgaaag aggcacagtg gtaccagaag   3720
gattatcgaa tgctgatgca tagaaacgag tcagagattg aaacagtcac tggaaagaag   3780
gcttgatgtt gtgacagcag tcagtcagaa taaagagaag tggtgccatc agaatggtca   3840
ctggaaaggc tcgaattgta gaactatcat aagaaagtga attgtggctg ggagactctt   3900
```

tgaaagacaa aatctattta ggtctccaca agatcatgga tgctctaatg ctatgtgaga 3960
aactaagaga gtggacgaaa ataaatggat tacttgataa aatacaatcc atacgtttaa 4020
atccgaatga ctaactttaa ttttaacaca acttttacat ctaaaagtat gacacgtgac 4080
acttaacctt tcatgcttgt gttcacaact tcgcatgtcg ccgacttgtt tacaagaact 4140
ttatttttca tacatgacag gtttgttgga agaccttgga tctgctccat cgggagcgat 4200
agtgctactt catgcttgtg cccataaccc cactggtgtt gatccaacca ttgatcagtg 4260
ggagcaaatt aggagattga tgagatcaag aggattgttg cccttctttg atagtgcata 4320
tcaggtaaga aatcatcaac agatgttcag agcactttgg ctgttggagt tgttgctgta 4380
tgagcattta aaagtgaggc ggtttattca gtatatgtca attaaccttg atattcaaac 4440
tttgatattc tagggctttg ccagtggaag cctagataca gatgcacagt ctgttcgcat 4500
gtttgtcgca gatggaggtg aagtacttgt tgctcaaagt tatgcaaaga atatggggct 4560
ttatggtgaa cgtgtcggag ctctaagcat cgtatgtctc aaaggacaaa ggacaactgt 4620
gccttgtttc tgaaaattta tatctccagt tgttcatttg ttgcattacc tttatttttc 4680
tcagattgat tctcatgatg catgaactgt cttactgttt tcatagtgtt cttttgtgat 4740
cttaaaattt ggtagttatg aactgttaaa gcttatatag cttacttcca aatatataac 4800
tgtgagcctt ggacatcaca tataaattat tttatatcac ggggtcgaga tgtggaaaca 4860
acctcttgca gaaatgtagg gtaaggttgc gtacaataga cccttgtggt ccggcccttc 4920
ctcggacccc tgcacatagc gggagcttag tgcactgggt tgcccttgtt ttcatcctga 4980
ggcataaaaa gtttttaatt tctcaagaat gaataaagag cctgttataa caggcacttt 5040
gcatgtcata tggtgttgtt tgtcacacag ttatgcatat agtgtagttt atcacacaaa 5100
tgaaaaaaat tgaaggatat agttctgaac cctcagttaa actctgctga cagatataat 5160
tcttcaaaat tttctcgaat ctgtaggtct gcagaaatgc tgatgtggcg agcagagttg 5220
agagccagct gaagttggtg attaggccaa tgtattccaa tccgcccatc catggtgcgt 5280
caatagttgc cacaatcctt aaagacaggt aatatatcaa ccatcaggaa attgcttctt 5340
gggaccccaa aaaagccatt tcctttcttt ctatatgata gaatccagtg tatgatcaaa 5400
aattatgttt agtcattgtt ctgcaaaata aatcactaaa tttctgcaga aacatgtacc 5460
atgaatggac ccttgagctg aaagcaatgg ctgatagaat catcagaatg cgtcagcaat 5520
tatttgatgc tttacgtgct agaggtaaat ttgctgcatt attttcacgt atgcgtgctc 5580
ttattacatg tttcttgctg catcgacttc ggatattttt ctcatttttg ataatttcgg 5640
ttcaagtgtc attataaatg ctacatgttc gtggcgtata cttctacata taaaatatgc 5700
tgcaactcgt tccagctcat ttgtctagat aattgatgaa aaggaccaat cttcacagct 5760
gactctcctg aatgaaagct taacgaagga aaaagattaa gcaaacaaaa catggaattc 5820
gacaaattca aacatttctc caaatcttaa tacatctcga tccttcttag tgctttcatc 5880
aacttcttag gtaattcacc tcttaacttt ggctctgact ggattctcta cctttggaaa 5940
accatcccca aagatgtccc ttgcacgatc cttttgggga catgaactgt tggatcaggc 6000
aagaaactat cccccaataa agaaaaattg ttggatcaga ttttttcctg ataggttgca 6060
ttctttcagc attcccctta aagtttgtga tttggacgtt gtcctcattg tgttacaaaa 6120
aaatgtcatt ggaaacttcc attttggcac atcaggtgtt agaatcatca tgtcttcata 6180
aattggcaat agacaaagtc tcatgtcgtc aactcctttc ttcagtgtca ggcattcttt 6240

```
aatcaatgca agtgtcgagc attgcatgaa taggatacct attactattt acatgaattg   6300

atgggcaagt cgggcatttt ttagtcggct taaaggtcaa gcattgcatg aacaagatat   6360

ctatttctat tgacttcaat tgattggcag gtacacctgg tgactggagt cacattatca   6420

agcagattgg aatgtttact ttcacgggac ttaactcaga gcaagttgcc ttcatgacca   6480

aagagtacca catctacatg acatcagatg ggtaatgtgt catttcttag cacaaagttc   6540

tgtatatgtc atatcagact accatgtccc ccctacatct gatatgtgat tttattacct   6600

cgtaagctcg gatggtaaaa cagaaagagg gaagggattt aaaatcttat cagccgtcag   6660

tttgttcttt tcttgtagta ttcttgctac cttagctttg atgttcgcta agagaaatgt   6720

ggcggtacta atgaacattt ctagagcatg gttctttcta agtttgtatt taattgtggc   6780

aacttcaatt aagcttagga tatcagataa tccaaagcct ttgacataca tcacatattt   6840

cattttgcag acgcatcagt atggcaggtc tgagctccag gacagttcca catctagcag   6900

atgccataca tgctgctgtt gctcgagctc gttga                              6935
```

<210> SEQ ID NO 4
<211> LENGTH: 448
<212> TYPE: PRT
<213> ORGANISM: Nicotiana tabacum

<400> SEQUENCE: 4

```
Met Asn Met Ser Gln Gln Ser Pro Ser Ala Asp Arg Arg Leu Ser Val
1               5                   10                  15

Leu Ala Arg His Leu Glu Pro Ser Ser Ser Ala Thr Val Glu Thr Ser
            20                  25                  30

Ile Val Ala Ala Pro Thr Ser Gly Asn Ala Gly Thr Asn Ser Val Phe
        35                  40                  45

Ser His Ile Val Arg Ala Pro Glu Asp Pro Ile Leu Gly Val Thr Ile
    50                  55                  60

Ala Tyr Asn Lys Asp Ser Ser Pro Met Lys Leu Asn Leu Gly Val Gly
65                  70                  75                  80

Ala Tyr Arg Thr Glu Glu Gly Lys Pro Leu Val Leu Asn Val Val Arg
                85                  90                  95

Gln Ala Glu Gln Leu Leu Val Asn Asp Arg Ser Arg Val Lys Glu Tyr
            100                 105                 110

Leu Ser Ile Thr Gly Leu Ala Asp Phe Asn Lys Leu Ser Ala Lys Leu
        115                 120                 125

Ile Leu Gly Ala Asp Ser Pro Ala Ile Gln Glu Asn Arg Val Thr Thr
    130                 135                 140

Val Gln Cys Leu Ser Gly Thr Gly Ser Leu Arg Val Gly Ala Glu Phe
145                 150                 155                 160

Leu Ala Arg His Tyr His Gln Arg Thr Ile Tyr Ile Pro Gln Pro Thr
                165                 170                 175

Trp Gly Asn His Pro Lys Val Phe Thr Leu Ala Gly Leu Ser Val Lys
            180                 185                 190

Ser Tyr Arg Tyr Tyr Asp Pro Ala Thr Arg Gly Leu Asn Phe Gln Gly
        195                 200                 205

Leu Leu Glu Asp Leu Gly Ser Ala Pro Ser Gly Ala Ile Val Leu Leu
    210                 215                 220

His Ala Cys Ala His Asn Pro Thr Gly Val Asp Pro Thr Ile Asp Gln
225                 230                 235                 240

Trp Glu Gln Ile Arg Arg Leu Met Arg Ser Arg Gly Leu Leu Pro Phe
                245                 250                 255
```

Phe Asp Ser Ala Tyr Gln Gly Phe Ala Ser Gly Ser Leu Asp Thr Asp
260 265 270

Ala Gln Ser Val Arg Met Phe Val Ala Asp Gly Gly Glu Val Leu Val
275 280 285

Ala Gln Ser Tyr Ala Lys Asn Met Gly Leu Tyr Gly Glu Arg Val Gly
290 295 300

Ala Leu Ser Ile Val Cys Arg Asn Ala Asp Val Ala Ser Arg Val Glu
305 310 315 320

Ser Gln Leu Lys Leu Val Ile Arg Pro Met Tyr Ser Asn Pro Pro Ile
325 330 335

His Gly Ala Ser Ile Val Ala Thr Ile Leu Lys Asp Arg Asn Met Tyr
340 345 350

His Glu Trp Thr Leu Glu Leu Lys Ala Met Ala Asp Arg Ile Ile Arg
355 360 365

Met Arg Gln Gln Leu Phe Asp Ala Leu Arg Ala Arg Gly Thr Pro Gly
370 375 380

Asp Trp Ser His Ile Ile Lys Gln Ile Gly Met Phe Thr Phe Thr Gly
385 390 395 400

Leu Asn Ser Glu Gln Val Ala Phe Met Thr Lys Glu Tyr His Ile Tyr
405 410 415

Met Thr Ser Asp Gly Arg Ile Ser Met Ala Gly Leu Ser Ser Arg Thr
420 425 430

Val Pro His Leu Ala Asp Ala Ile His Ala Ala Val Ala Arg Ala Arg
435 440 445

<210> SEQ ID NO 5
<211> LENGTH: 6388
<212> TYPE: DNA
<213> ORGANISM: Nicotiana tabacum

<400> SEQUENCE: 5
atggcgatcc gagccgcgat ttccggtcgt cccctcaagt ttagctcgtc ggtcggagcg 60
cgatctttgt cgtcgttgtg gcgaaacgtc gagccggctc ctaaagatcc tatcctcggc 120
gttaccgaag ctttcctcgc cgatcctact cctcataaag tcaatgttgg tgttgtaagt 180 tttttttct ctttgctttg tttgattttc cacttcattt cgtgtaagct aggatttagc 240
ttacttgacc atttcgctat tcttcatagg ccatagctgt aaaaatggtt ttactgtgac 300
gaatcttcga cgatctcaat cgctttggga ttgggagaga gtttattgat ttaatttttg 360
tatgcattcc actttttca acttgatcta tttaagaaaa aaattgaaaa agatttgacc 420 tttttctta aattatttct tttaaatttt ttatttttgt gattattata tagggagctt 480
acagagacaa caatggaaaa cccgtggtac tggagtgtgt tagagaagca gagcggagga 540
tcgctggcag tttcaacatg tgagtgctct cctgatttat tcaagttttt ctgttatttt 600
atttgtaatt aattacgatt acgttaactt tgatctatta gaaaatagaa acttcagcca 660
gtaagattac tttttttctt cgaggagtgt gagatgtaaa cccaggtcgg atgcactgga 720
attcttcact agtttgtgca aatatattct taatattttt caaaaacttc ctgtgtacac 780
acacacatac atgtaattaa ttaagtaatt acctactgat ctaggatttt taggtagttc 840
ggaaaaatat attttcaata tcgtttaaga attttctggg tatgcgtagt ttgagtatga 900
taaaatgggt gcatgtgcac cactgcttac gctagggaac agcctctaat tagctgttgg 960
tgagtctggt gagtggtgac tgttctttat tttcagttac ttcgcacatt gttggtttt 1020

-continued gattaagtat aaataaacga atgttttagt gagtgcttat ttctatgaag catctttttt 1080
aggtctacag aaatgggtgg tacgatattt tccagccgtc agctccacta accagtttga 1140
ttctttggga ctttttcttt gtattctcac gtttacttct agtggatggt gcagatggat 1200
ttctttacta attctttctt ctgcgtttgc agagctttct cccaagataa attattaata 1260
tcaaattgac ctttcgatag ttcaatggtg tttaactttt tcaaatattg cccattttat 1320
attatgaagt ttgaaagttt aactagacat gttgtaataa attttatttg acttgtgtat 1380
tttattcatt gtggttggag aaagtattaa aataacaagt gaaaagtctg ttttacgtca 1440
agtttgaatt tgaattttg aattgatttg cttctttaag tttatgaaac catctatgag 1500
aatattattg gcactccatt gtctcatttt atgtgaaggc atttgacgtt gcacaaaatt 1560
taaaaatata aagaaactta tgacgtgtaa gttagatata tgcagagtac catagttatc 1620
cttttaagta agtgatagtg agagtttcac atttcttttt gttctctctt cttataaaag 1680
aatgaatttt tgtatcccaa caagtcatat cattaatgtt aacacgggga tactaagatt 1740
aactaatgtc taaaaagaga aagatttcat tcttcttgga cgggctaaaa aggaaagtat 1800
gtcacataaa atgagacaga gatatgttag gatttgtcct gaatttctaa tcaattagga 1860
ctctctttct tgaaggaatg gaaaaagact cctaaaagga ttaaatctcc ttaatatgtc 1920
ttatcctttt cttggaagac aagttttgca catctataaa ttaaggatct ctgcttttca 1980
caagaacaca aaaaaaaaat atccacaatg tagttattaa agagtttgtt taggggggaga 2040 tttttctctc gatagttttt cttcttttat attagtttta tcatatgtag atcaattgac 2100
caaatcatta taaactatta tgcttagttt aatatatttt tcttttgttg tctgatttat 2160
cgtccatcaa gttttgtatt gttagttttc gcatgcacca tgttatttcg aacccaacaa 2220
gtggtatcag agccaatggt tcagagtcaa cggttgaacg aggttgaaga aagattcaat 2280
gcgtgtttag atcaagacga taatgaagat ttattcaaca tgctacatgt ggagataaat 2340
ttacaattac aattgtattc aacacgcctg ctgttgcatc tttattggaa taaaaactct 2400
ttctaaccca tattttggcc actttaaacc aatgccaatt ttaagtcatg cctacttgca 2460
acacatgagt tccagtgcca gttttaactc acgcttcttt ttaatgcatg agcttctttt 2520
atcccatgtt tattcttaac acgcgggctc cttttaaccc atacttggtt ttttttaac 2580 caataccaag attttcaatt tttaatcatg gcaagcagca gtgatgaaga ttatgtgaag 2640
aaggtgaatc aactttgtca agaaaattca ggccaagggg agattgttag gatttgtcct 2700
gaatttctaa tcaattagga ctctctttct tgaaggaatg gaaaaagact cctaaaagga 2760
ttaaatctct ttactatgtc ttatcatttt cttggaagac aagttttgca catctataaa 2820
ttaaggatct ctgcttctca caagagcaca aaaaaaaaaa tatccacaat gtagttatta 2880
aagagttttg tttaggggga gatttttctt tcaatagttt ttcttctttt atattagttt 2940
tatcatatgc agatcaattg accaaactat tatgcttagt ttaatatttt tttttttgt 3000 cgtctgattt atcgtccacc aagttttgta ttgttagttt ccgcatgcac catgttattt 3060
cgaaccctcg tataagtttg tcaaacattt tgtgacttcc taaactagaa agtgtcttgg 3120
gatgggggag aactacgcta tctgatctca aaaaaagtgt gcatcatgtg atactatgtg 3180
gatagtttag ttcacatgtt gacaattcat catttatcag ggaatatctt cctatgggag 3240
gtagtgtcaa catgatcgag gagtcactga agttagccta tggggagaac tcagacttga 3300
taaaagataa gcgcattgca gcaattcaag ctttatccgg gactggagca tgccgaattt 3360
ttgcagactt ccaaaggcgc ttttgtcctg attcacagat ttatattcct gttcctacat 3420
ggtctaagta agtgtattct tctgcttctc ggcatctcta cagcatccta attgatcttc 3480
ctcaattggt ttttgcactt taaaacatga gtatgcaaat accttcaaaa ttttctaatt 3540
tcctgtcatt actaatataa agttcttggc agtcatcata acatttggag agatgctcat 3600
gtccctcaga aaatgtatca ttattatcat cctgaaacaa aggggttgga cttcgctgca 3660
ctgatggatg atataaaggt aagaaaacat atatttgagg ttgtttgcca tgatggttgg 3720
ttctcctgtt tgatgatata gtgtccctcc tcaagtggca attatgtgtt ctatcctgac 3780
gtatttcaat tttcattgac atagaatgcc ccaaatggat cattctttct gcttcatgct 3840
tgcgctcaca atcctactgg ggtggatcct acagaggaac aatggaggga gatctcacac 3900
cagttcaagg taatgatttg tatgttttgt ctctcccttt tcttgtcata agtcatatta 3960
aatttattac actggttcca ggtgaaggga cattttgctt tctttgacat ggcctatcaa 4020
ggatttgcta gtgggaatcc agagaaggat gctaaggcta tcaggatatt tcttgaagat 4080
ggtcatccga taggatgtgc ccaatcatat gcaaaaaata tgggactata tggccagaga 4140
gttggttgcc taaggtaaac tactactccc accatcatat cttatttgcc ctagttacaa 4200
tctggagagt caaacaaact ttttattaga ccatagttgg tctatttttc aaatgatcta 4260
attccaaaag cagttactac tatttcatgc aaattctaga ttaattaacc ttttgctata 4320
cctcattatc ttcatttagt aggcagtagc taattttacc atatatcata tttttcatat 4380
aatcaatatg tagagttatt tatttattta tatattttaa atttatttag gataaatttt 4440
gttctttccg gtaatttcag ttcatttcca cctaaaagtc caactcgaag agaaaaacag 4500
aattttgcta gtcaaaactt agatccaatg aaaagcacca aaattttggt tttaaattat 4560
aaaacatgtc tactctaggt ttttttccta ggcaagcgat gtgattttac aatcttacaa 4620
taaggcatca atcaatccca aactagtttg gttcaacaat ataaatcttt gttcctattt 4680
catggcattg ggcccattgc attccaataa tggtaaataa gacaaattag aggttatcta 4740
agattagaga ttccttatta aaatctcata cttatatcta cattgtcacg caagtctctg 4800
accttaaaag aagacttcta gcagacacca gacttaacgt aagtgtaaca acaacaacta 4860
agttttaatc caaactagtt agtatcgctt atatgaatcc cttgcttcca ttgtgtagca 4920
ctaaacaaca acaacaacat accgagtata atctcacata gtggggtctg gggagggtag 4980
tgtgtacgca gactttaccc ctgccttgtg gagaaagaga ggctatttcc aatagaccct 5040
cggctcaaaa ccattgtgta gcaatggagg catgaaatag aaaacttgtc ttctgattaa 5100
aatctgttat taaattaatg aggagaaaaa attggattac ttgttggtaa atcttatttg 5160
ttgttttaaa cacacacaaa gccgaaagac ctctgatact tttcctgaga tgcttccgca 5220
attcactgca gtgtggtttg tgaggatgaa aaacaagcag tggcagtgaa aagtcagttg 5280
cagcagcttg ctaggcccat gtatagtaat ccacctgttc atggcgcgct cgttgtttct 5340
accatccttg gagatccaaa cttgaaaaag ctatggcttg gggaagtgaa ggtaatatgg 5400
ttagaacaag aaaagattta tgattatata actatcattg gtattttgac aaaaggtagg 5460
aactaggaac cttgctatta aagatatttt cttcccttta ttttggaaaa aaaggtattt 5520
tcttgctttc ttcaaatgtt tgagatttgg atagagccgt tacatggaaa tgctgtgcaa 5580
ttttctgcta ctcacatgga aaagatcttt ttctttttgct gatctgttta agcacctatt 5640
tgctaaagcc tactatgtca gtatgttgtt caatcttttc agccacagaa acaggtctaa 5700
accagttcca aactttaaat aatcttacca tggtagtttc agcaaagata aattggtccg 5760

-continued

```
tgcagccatt aactgttttc tttgtcgggc ttcttaaact tgttttctcc aaggtctagt   5820

tgttggtgct gtggctgctt tttagctttg tgctcattat cagagcatca tatgtttaag   5880

tgtaaaggtt caatgactaa gttctttttc cagggcatgg ctgatcgcat tatcgggatg   5940

agaactgctt taagagaaaa ccttgagaag ttggggtcac ctctatcctg ggagcacata   6000

accaatcagg tattgaaatc aacaacttct gttgttttct atgctactag tatataacta   6060

ttaagaaaat tactgtggtt cacctactgc gccattaata ctcgatacca ccaacagatt   6120

ggcatgttct gttatagtgg gatgacaccc gaacaagtcg accgtttgac aaaagagtat   6180

cacatctaca tgactcgtaa tggtcgtatc aggtataatc attaggtcac caatttctgc   6240

ttaatgctcc ggtgttcttg tacagagtta tatctcatta tttttccac tatgttgtgt    6300

gttttgtacg tgcagtatgg caggagttac tactggaaat gttggttact tggcaaatgc   6360

tattcatgag gccaccaaat cagcttaa                                      6388
```

<210> SEQ ID NO 6
<211> LENGTH: 424
<212> TYPE: PRT
<213> ORGANISM: Nicotiana tabacum

<400> SEQUENCE: 6

```
Met Ala Ile Arg Ala Ala Ile Ser Gly Arg Pro Leu Lys Phe Ser Ser
1               5                   10                  15

Ser Val Gly Ala Arg Ser Leu Ser Ser Leu Trp Arg Asn Val Glu Pro
            20                  25                  30

Ala Pro Lys Asp Pro Ile Leu Gly Val Thr Glu Ala Phe Leu Ala Asp
        35                  40                  45

Pro Thr Pro His Lys Val Asn Val Gly Val Gly Ala Tyr Arg Asp Asn
    50                  55                  60

Asn Gly Lys Pro Val Val Leu Glu Cys Val Arg Glu Ala Glu Arg Arg
65                  70                  75                  80

Ile Ala Gly Ser Phe Asn Met Glu Tyr Leu Pro Met Gly Gly Ser Val
                85                  90                  95

Asn Met Ile Glu Glu Ser Leu Lys Leu Ala Tyr Gly Glu Asn Ser Asp
            100                 105                 110

Leu Ile Lys Asp Lys Arg Ile Ala Ala Ile Gln Ala Leu Ser Gly Thr
        115                 120                 125

Gly Ala Cys Arg Ile Phe Ala Asp Phe Gln Arg Arg Phe Cys Pro Asp
    130                 135                 140

Ser Gln Ile Tyr Ile Pro Val Pro Thr Trp Ser Asn His His Asn Ile
145                 150                 155                 160

Trp Arg Asp Ala His Val Pro Gln Lys Met Tyr His Tyr Tyr His Pro
                165                 170                 175

Glu Thr Lys Gly Leu Asp Phe Ala Ala Leu Met Asp Asp Ile Lys Asn
            180                 185                 190

Ala Pro Asn Gly Ser Phe Phe Leu Leu His Ala Cys Ala His Asn Pro
        195                 200                 205

Thr Gly Val Asp Pro Thr Glu Glu Gln Trp Arg Glu Ile Ser His Gln
    210                 215                 220

Phe Lys Val Lys Gly His Phe Ala Phe Phe Asp Met Ala Tyr Gln Gly
225                 230                 235                 240

Phe Ala Ser Gly Asn Pro Glu Lys Asp Ala Lys Ala Ile Arg Ile Phe
                245                 250                 255

Leu Glu Asp Gly His Pro Ile Gly Cys Ala Gln Ser Tyr Ala Lys Asn
```

```
            260                 265                 270

Met Gly Leu Tyr Gly Gln Arg Val Gly Cys Leu Ser Val Val Cys Glu
        275                 280                 285

Asp Glu Lys Gln Ala Val Ala Val Lys Ser Gln Leu Gln Gln Leu Ala
    290                 295                 300

Arg Pro Met Tyr Ser Asn Pro Pro Val His Gly Ala Leu Val Val Ser
305                 310                 315                 320

Thr Ile Leu Gly Asp Pro Asn Leu Lys Lys Leu Trp Leu Gly Glu Val
                325                 330                 335

Lys Gly Met Ala Asp Arg Ile Ile Gly Met Arg Thr Ala Leu Arg Glu
            340                 345                 350

Asn Leu Glu Lys Leu Gly Ser Pro Leu Ser Trp Glu His Ile Thr Asn
        355                 360                 365

Gln Ile Gly Met Phe Cys Tyr Ser Gly Met Thr Pro Glu Gln Val Asp
    370                 375                 380

Arg Leu Thr Lys Glu Tyr His Ile Tyr Met Thr Arg Asn Gly Arg Ile
385                 390                 395                 400

Ser Met Ala Gly Val Thr Thr Gly Asn Val Gly Tyr Leu Ala Asn Ala
                405                 410                 415

Ile His Glu Ala Thr Lys Ser Ala
            420


<210> SEQ ID NO 7
<211> LENGTH: 4789
<212> TYPE: DNA
<213> ORGANISM: Nicotiana tabacum

<400> SEQUENCE: 7

atggcgattc gagccgcgat ttccggtcgt tccctcaagc atattagctc gtcggtcgga      60

gcgcgatctt tgtcgtcgtt gtggcgaaac gtcgagccgg ctcctaaaga tcctatcctt     120

ggcgttaccg aagctttcct cgccgatcct actccccata aagtcaatgt tggcgttgtg     180

agtttttttt tcctctttgt tttgcttcat tttccacctc atttcgtgta tgcaaggatt     240

tagcttactt gaccatttcg ctatacttcc cttggtaggc catagctgta aaaaatagtt     300

ttactgtgac gaatcatcga catatggata cagagtattc taatggagta gtcaacaaca     360

taagtcgatc tcaatcgctt tgggattgag aaagagttta ttgatttaat ttttgtatgc     420

gttccacttt tttcaacttg atctatttaa gaaaaaaatt gaaaaagatt tgaccttttt     480

tcttaaatta tttcttttat aaaatttgct tttgtgatta ttatacaggg agcttacagg     540

gacgacaacg gaaaacccgt ggtactggag tgtgtcagag aagcagagcg gaggatcgct     600

ggcagtttca acatgtgagt gcttctcctg atttattcat ttttttctgt tatttatttg     660

taattaatta cgattacgtt aaatttgatc tattagaaaa tataaacttc agccagtaag     720

attacttttt ttcttcgagg agtttgagat gtaaaaccca ggtcggatgc actgggattc     780

ttaagtagtt tgtacaaata tattcttaat agttttgtaa aatttgctgt atacacacac     840

atgtaattaa ttacctactg atctaggatt tataggtagt tcggaaaaat atattttcaa     900

tatcgtttaa gaatttcctg ggtgtgtata gtttgagtat gagaaaatgg gtgcatgtgc     960

accactgctt acgctaggga tcagcttcta aatagctggt ggtgagtctg gtgagtggtg    1020

actgttcttt attttcagtt actgtagcca caaattgttg gttattgatt aagtataaat    1080

aaacgaatgt attagtgagt gcttatttgt atgaagcatc ttttttaagt ctacagaaat    1140

gggtggtccg atattttcca cccgtcagtt cctctaacta gtttgattct ttgggacttt    1200
```

```
ttctttgtat tctcacgttt acgcctagtg gatggtgcag atggatttct ttactaattc   1260
tttcttctgc gcttgcagag ctttctccca agataaatta ttaatatcaa attgaccttt   1320
cgatagttca atggtgttta actttttcaa atattgcccc acatcccatt ttatattatg   1380
aagtttgaaa agtttaacta gacatgttgt aataaatttt tatttgagtt gtgtatttta   1440
ttcattgtgg taggagaaac tagaaagtat taaaataaca agtgaaaagt ctgttttatg   1500
gataaagaat attacgtcaa gtttgaattt gaaattttga attgatttgc ttctttaaat   1560
ttatgaaacc atctatgaga atattattag cactccattt gtctcatttt atgtgaaggc   1620
atctgacttt gcacaaagtt aaaaaatata aagatactta cgacgtgaaa gtttgatata   1680
tgccaagtac cataattatc cttttaagca agtgatagtg agagtttaac atttcttttt   1740
gttctctctt cttataaaag aatgaatttt gtatcaagtg ggtcccaaca agtcattcat   1800
taagggtaaa acggggatgc taagattaac taatttccaa aaagagaaag atttaattct   1860
tctaggacag gctaaaaatg gaaagtgttt cacataaaat gagacataga caatataagt   1920
ttgtcaaaca ttttgtgacg tcctaaaata gaaagtgtcc tgagatggag gagaactacg   1980
ttatctgttc tcaaaaaagt gtgtatcatg tgatactatg tggatagttt agttcacatg   2040
ttaacaattc atcatttatc agggaatatc ttcctatggg aggtagtgtc aacatgatcg   2100
aggagtcact gaagttagcc tatgggggaga actcagactt gataaaagat aagcgcattg   2160
cagcaattca agctttatct gggactggag catgccgaat ttttgcagac ttccaaaggc   2220
gcttttgtcc tgattcacag atttatattc ctgttcctac atggtctaag taagtgtatt   2280
cttctgcttc tcggcatctc tacagcatcc taattgatct tcctcaattg gtttttgcac   2340
attaaaacat gagtatgcaa ataccttcaa aattttctaa tttcctgtca ttactaatat   2400
aaaattcttg gcagtcatca taacatttgg agagatgctc atgtccctca gaaaacgtat   2460
cattattatc atcctgaaac aaaggggttg gacttcactg cactgatgga tgatataaag   2520
gtaagaaaac atatatttga ggttgttttc catgatggtt tgttctcctg tttgatgata   2580
tagcgtccct cctcaagtgg caattatgtg ttctatcctg acgtatttca attttcattg   2640
acatagaatg ccccaaatgg atcattcttt ctgcttcatg cttgtgctca caatcctact   2700
ggggtggatc ctacagagga acaatggagg gagatctcgc accacttcaa ggtaatgatt   2760
ttgtatattt tgtctctcct ttttcttgta ccaagtcata ctaaatttat tacactggtt   2820
ccaggtgaag ggacattttg ctttctttga catggcctat caaggatttg ctagtgggaa   2880
tccagagaag gatgctaagg caatcaggat atttcttgaa gatggtcatc cgataggatg   2940
tgcccaatca tatgcaaaaa atatgggact atatggccag agagttggtt gcctaaggta   3000
aactactact cccaccatca tatcttattt gccctagtta caatctggag agtcaaacta   3060
actttttgtt agaccttagt cggtctattt ttcaaatgtt ctaattccaa aagcagttac   3120
tactatttcc tgtaaattct agattaatta actttttatt atacctcatt atcttcattt   3180
agtagctaat tttaccatat atcatatttt tcatattatc aatatgtaga gagaattatt   3240
tatttaaata ttttaagttt atttataaaa aattgagttc tttccgataa cttcagttca   3300
tttccacctc aaagtccaac tcgacgtgaa aagcagaatt ttgctagtca aaacttggat   3360
ccaacaatta tttagaataa attgagttct ttccgataac ttcagttcat ttccacctca   3420
aagtccaact cgacgagaaa aacagaattt tgctagtcaa aacttggatc caatgaaaag   3480
caccaaaatt ttggttttaa attacaaaat aatgtatact ctaggttttt gtcctatgca   3540
```

-continued

```
agtgatttta cggtcttaaa ataaagcatc aatcaatccc ttaaacacac acaaagccct   3600

ctaatacatt tgctgagatg cttccgcaat tcactgcagt gtggtttgtg aggatgaaaa   3660

gcaagcagtg gcagtgaaaa gtcagttgca gcaacttgct aggcccatgt acagtaatcc   3720

acctgttcat ggtgcgctcg ttgtttctac catccttgga gatccaaact tgaaaaagct   3780

atggcttggg gaagtgaagg taatgtgatt agaacgagat aaagatttat gattgtataa   3840

ctatcattgg tattttgacg acagatagga actaggaacc ttgctattaa agatattttc   3900

ttgccttaat tttgaaaaaa gggaattttc tcgctttttt ggaatgtatg agatttggat   3960

agaactatca catggaaatg ctgtaccatt ttctgctact cacatggaaa agatcctttt   4020

cttttgctga tctgtttaag caccaatttg ccatagcttt gttgtcctat attttcagcc   4080

acagaaataa gtctaaacca gtcccaagct ttaataagct ttcattgcgt ggtagtgtca   4140

gccgcataaa ttggtcagtg cagccattaa ctgttttctt catggggcct gttaaccttg   4200

tatttctcca aggtcaagtt gttggtgttg tggctgcttt ttagctttgt actcattatc   4260

agagcatcat atgttaaacg taaaggttca atgactaaga gttttttttc cagggcatgg   4320

ctgatcgcat catcgggatg agaactgctt taagagaaaa ccttgagaag aagggctcac   4380

ctctatcgtg ggagcacata accaatcagg tattgaaatc aatgacttct gttgcgttct   4440

atactagtat ataactatta gaacactatg gctcacctat tgccccatta atactcgata   4500

ctgcctacag attggcatgt tctgctatag tgggatgaca cccgaacaag ttgaccgttt   4560

gacaaaagag tatcacatct acatgactcg taatggtcgt atcaggtata atcactcatt   4620

cacgaatttc tgcttaatgc tccggtgttc ttgtacgagt taatatctca ttaatttttc   4680

cactatgtta tactgtgtgt tttgtatgtt gtgcagtatg gcaggagtta ctactggaaa   4740

tgttggttac ttggcaaacg ctattcatga ggttaccaaa tcagcttaa               4789
```

<210> SEQ ID NO 8
<211> LENGTH: 425
<212> TYPE: PRT
<213> ORGANISM: Nicotiana tabacum

<400> SEQUENCE: 8

```
Met Ala Ile Arg Ala Ala Ile Ser Gly Arg Ser Leu Lys His Ile Ser
1               5                   10                  15

Ser Ser Val Gly Ala Arg Ser Leu Ser Ser Leu Trp Arg Asn Val Glu
            20                  25                  30

Pro Ala Pro Lys Asp Pro Ile Leu Gly Val Thr Glu Ala Phe Leu Ala
        35                  40                  45

Asp Pro Thr Pro His Lys Val Asn Val Gly Val Gly Ala Tyr Arg Asp
    50                  55                  60

Asp Asn Gly Lys Pro Val Val Leu Glu Cys Val Arg Glu Ala Glu Arg
65                  70                  75                  80

Arg Ile Ala Gly Ser Phe Asn Met Glu Tyr Leu Pro Met Gly Gly Ser
                85                  90                  95

Val Asn Met Ile Glu Glu Ser Leu Lys Leu Ala Tyr Gly Glu Asn Ser
            100                 105                 110

Asp Leu Ile Lys Asp Lys Arg Ile Ala Ala Ile Gln Ala Leu Ser Gly
        115                 120                 125

Thr Gly Ala Cys Arg Ile Phe Ala Asp Phe Gln Arg Arg Phe Cys Pro
    130                 135                 140

Asp Ser Gln Ile Tyr Ile Pro Val Pro Thr Trp Ser Asn His His Asn
145                 150                 155                 160
```

```
Ile Trp Arg Asp Ala His Val Pro Gln Lys Thr Tyr His Tyr Tyr His
                165                 170                 175

Pro Glu Thr Lys Gly Leu Asp Phe Thr Ala Leu Met Asp Asp Ile Lys
            180                 185                 190

Asn Ala Pro Asn Gly Ser Phe Phe Leu Leu His Ala Cys Ala His Asn
        195                 200                 205

Pro Thr Gly Val Asp Pro Thr Glu Glu Gln Trp Arg Glu Ile Ser His
    210                 215                 220

His Phe Lys Val Lys Gly His Phe Ala Phe Phe Asp Met Ala Tyr Gln
225                 230                 235                 240

Gly Phe Ala Ser Gly Asn Pro Glu Lys Asp Ala Lys Ala Ile Arg Ile
                245                 250                 255

Phe Leu Glu Asp Gly His Pro Ile Gly Cys Ala Gln Ser Tyr Ala Lys
            260                 265                 270

Asn Met Gly Leu Tyr Gly Gln Arg Val Gly Cys Leu Ser Val Val Cys
        275                 280                 285

Glu Asp Glu Lys Gln Ala Val Ala Val Lys Ser Gln Leu Gln Gln Leu
    290                 295                 300

Ala Arg Pro Met Tyr Ser Asn Pro Pro Val His Gly Ala Leu Val Val
305                 310                 315                 320

Ser Thr Ile Leu Gly Asp Pro Asn Leu Lys Lys Leu Trp Leu Gly Glu
                325                 330                 335

Val Lys Gly Met Ala Asp Arg Ile Ile Gly Met Arg Thr Ala Leu Arg
            340                 345                 350

Glu Asn Leu Glu Lys Lys Gly Ser Pro Leu Ser Trp Glu His Ile Thr
        355                 360                 365

Asn Gln Ile Gly Met Phe Cys Tyr Ser Gly Met Thr Pro Glu Gln Val
    370                 375                 380

Asp Arg Leu Thr Lys Glu Tyr His Ile Tyr Met Thr Arg Asn Gly Arg
385                 390                 395                 400

Ile Ser Met Ala Gly Val Thr Thr Gly Asn Val Gly Tyr Leu Ala Asn
                405                 410                 415

Ala Ile His Glu Val Thr Lys Ser Ala
            420                 425
```

<210> SEQ ID NO 9
<211> LENGTH: 4551
<212> TYPE: DNA
<213> ORGANISM: Nicotiana tabacum

<400> SEQUENCE: 9

```
atggcaaatt cctccaattc tgtttttgcg catgttgttc gtgctcctga agatcccatc      60

ttaggagtac gtccctttcc actctttcta ttttacattt ccactgaata tgtttcttct     120

gtggctcctt taataatctt ccgtaaatat actattagtg gatttgataa gctacttctc     180

tctccctctc tcttttattt tcttattttg ggttagatta aaatgaacat taattaatga     240

tcagatgatt tggttaaaga tgatatctag gagatcggca taaataagtt gattggaatg     300

atcgctatag ggtttcctat tgtatgcatt ggatcatgga tgtgtgcgct aattatttaa     360

tagtacttct ttctttttac tgtgatctgg caattcctta ttttattcct ggtgtagttg     420

atgaaaggtg tagatttgat tctttaactt gctctattga gaaggtaatt tgtgcttctc     480

aagtgtttat taatgttgtt ttcttctgtt gtgttacttc attaaaacag gtcacagttg     540

cttataacaa agataccagc ccagtgaagt tgaatttggg tgttggcgca tatcgcactg     600
```

```
aggtctgcca cttctacttt gtctcgttgt tctttattat tattattttt ttattatagc    660
caaaaaaagt tgccccttga atggatttgg tcctgctatg tgttgaatcc ttggttaagt    720
ttttctttaa taggctcctt cacaaggata gaaaattgta gacactgatg cttacacatt    780
agtaatattt tttcccctga tgcataatga agtgaaacca cttgtgcttc taaaaaatca    840
tactttgggg caaggtgaag tacacatttt tataagtggt tgtttttttc ttcaatcttg    900
agttgaatgt tagtgttaag taggagccgc aaacgggcgg gtcgggtcgg atttggttca    960
gatcgaaaat gggtaatgaa aaaacaggta aattatctga ctcgacccat atttaatacg   1020
gataaaaaca ggttaaccgg cggataatat gggtaaccat attattcatg tcttcttgca   1080
tatgatcaat tatgggagaa ttcttagcct caaatgggaa cccccaattt gaggctttac   1140
aaatttaaaa gttagaccca ttggttaacc attttctaaa tggataatat ggttcttatc   1200
catatttgac ccatttttaa aaagttcatt atccaaccca ttttttagtg gataatatgg   1260
gtgtttaact gatttctttt aaccattttg acacccctag tgttaagctt gaaaacgact   1320
aatgcatagt ctgatgacaa cttgcaggaa ggaaagcccc ttgttcttaa tgtggtgaga   1380
cgggctgaac aaatgctcgt caatgacacg taacttgcca aattagaaac tagcttacag   1440
attttctttt gagatatgat cacctgatac caagattgga atctaaggct gctatgatgc   1500
aggtctcggg tgaaggagta tctctcaatt actggactag cggattttaa caaactgagt   1560
gcaaagctta tatttggtgc tgacaggttt ggagattttt tggtgcagtt gctcttgata   1620
aatgcttgag tcaatttttt ttaaaaaaaa tgctcactat ccatgtcgct ctatttaaac   1680
ctatcttgcc aaaccacttg tataaatgaa aatgagccgt cgatattctt ccttccatct   1740
agtttgatat ttgaattaga gattgttgct aaaagggaat gctttatctc tacagcgtag   1800
agtaactgaa tacctgttaa acatgttcct ccgtatttca tcttattatg atgccttgca   1860
tctgaagaaa attgttctag agttaacttt ctctcctctt tgttgtactg attatctgtg   1920
tgtggtgaac gcgatatcag gaaatatgtg tcttctgtca ctattactcc ttgttaagtc   1980
atatgtaatt gacttgttat gatatcaaca gatttactta tgtttagatg tagtttaaat   2040
gctttttgtg ctgttttgtt gcttatacag ccctgccatt caagagaaca gggtgactac   2100
tgttcagtgc ttgtcgggca caggttcttt gagggttggg gctgaatttc tggctaagca   2160
ttatcatgaa gttagtattc cttgctctct ttccctttat atgtctaaat caaatggaca   2220
cttgtataag cttctactgt ttgttttgtt gccagcatac catatatata ccacagccaa   2280
catggggaaa ccatccgaag gttttcactt tagccgggct ttcagtaaaa tattaccgtt   2340
actacgaccc agcaacacga ggcctggatt tccaaggtac tactgtaatc actgttctta   2400
aagttctaca gttgtaagta agagccgatt tctctttttt atggacaagt gaactttctc   2460
ctggtcgtgt ctagaaagat ctatatttta tgtgtagcta gcacaggatc tttatttatt   2520
taattttgta ttctcttggt aaagatataa gcatagttta tctgtggctt ttcctgtatt   2580
tgggtgttgc atatcaaatt taatcatgaa ccctgtagga cttttggatg atcttgctgc   2640
tgcacccgct ggagcaatag ttcttctcca tgcatgtgct cataacccaa ctggcgttga   2700
tccaacaaat gaccagtggg agaaaatcag gcagttgatg aggtccaagg gcctgttgcc   2760
tttctttgac agtgcttacc aggtaaagct tatgatggga ttttgaattc aagtgatact   2820
tcgttaagaa tgattaccaa ataatttgaa gcgccaaact atgtattaat gggctgccca   2880
acggaccctt actataatga atatttttga tattgcaggg ttttgccagt ggcaacctag   2940
```

```
atgcagatgc acaatctgtt cgcatgtttg tggctgatgg tggtgaatgt cttgcagctc   3000

agagttatgc caaaaacatg ggactgtatg gggagcgtgt tggtgccctt agcattgtaa   3060

gtccttttgt cggttgtaat tgctttccct ttttagtaag cgataaaatt ggtggctgaa   3120

gaactatcca tggctatatc atgctatcta tgtctaaaga tgattttcct tgaaagcata   3180

attcaggtta tattccctag aaggctaaaa agaagttgtt ctgatggtac aatgaacaca   3240

gtctctagag atattgaaag ccaaattttt gaatatggct tcccctttga ttgtaattgg   3300

aaaacaaaga gaaggacaga gtggaattag taccggattg tatgtttagg aaaaagtgtc   3360

attttgtttg agttttatca gacagacact aaaagctgac taacagtaca ataaaatttt   3420

gtgttgtgtt ataggtttgc aaagacgcag atgttgcaag cagagtcgaa agccagctaa   3480

agctggttat caggccaatg tactctaatc caccaattca tggtgcgtct attgttgcta   3540

ctatactcaa ggacaggttt gtgcaactat ttacaagatt ctgttttgct gttagtagat   3600

gctatacctt ctacattttg atgtggtttc tcatctaatg gtgatagaca aatgtacgat   3660

gaatggacaa ttgagctgaa agcaatggcc gacaggatta ttagcatgcg ccaacaactc   3720

tttgatgcct tgcaagctcg aggtatttga tcttcatatt tgttctttct ggggaagcat   3780

actgtattct gtatgatggg tttgactgct actgcaatag gagcttttcc ctgaaaagta   3840

ccatggtgaa acaaccacgg caactaaatc ttttgacttc attgttcagt ttagtgctaa   3900

tgtaagtttt attctgttat gcaggtacga caggtgattg gagtcatatc atcaagcaaa   3960

ttggaatgtt tactttcaca ggattaaata ctgagcaagt ttcattcatg actagagagc   4020

atcacattta catgacatct gatgggtaag gacatctgac tattgatatt tttttattt   4080

gtttagtttg ttactttggg ttgctttttt ctcagtagaa acttaaataa ttggaactta   4140

gaagtccttc gttgattatt tcggcttgaa ttctttaata aggagaattt cagatttata   4200

gcttcagttt ggagaggaag cataaacaag tctgtcatcc atacttaaaa tttacagaaa   4260

aaagtgcagt tctgttttcc cccctcccag attagactaa ttcccaaaag aacttacctt   4320

caatctatgg aacatttagt attctggtat cagttgaaac atctctttgt tgaagttaag   4380

attttggtta aaaagatctt catctctagt aacattttct acattccatt tttagaagga   4440

atgattttct cctttctcat ttgcaggaga attagcatgg caggccttag ttctcgcaca   4500

attcctcatc ttgccgatgc catacatgct gctgttacca aagcggccta a            4551
```

<210> SEQ ID NO 10
<211> LENGTH: 446
<212> TYPE: PRT
<213> ORGANISM: Nicotiana tabacum

<400> SEQUENCE: 10

```
Met Ala Asn Ser Ser Asn Ser Val Phe Ala His Val Val Arg Ala Pro
1               5                   10                  15

Glu Asp Pro Ile Leu Gly Val Thr Val Ala Tyr Asn Lys Asp Thr Ser
            20                  25                  30

Pro Val Lys Leu Asn Leu Gly Val Gly Ala Tyr Arg Thr Glu Glu Gly
        35                  40                  45

Lys Pro Leu Val Leu Asn Val Val Arg Arg Ala Glu Gln Met Leu Val
    50                  55                  60

Asn Asp Thr Ser Arg Val Lys Glu Tyr Leu Ser Ile Thr Gly Leu Ala
65                  70                  75                  80

Asp Phe Asn Lys Leu Ser Ala Lys Leu Ile Phe Gly Ala Asp Ser Pro
                85                  90                  95
```

```
Ala Ile Gln Glu Asn Arg Val Thr Thr Val Gln Cys Leu Ser Gly Thr
            100                 105                 110

Gly Ser Leu Arg Val Gly Ala Glu Phe Leu Ala Lys His Tyr His Glu
        115                 120                 125

His Thr Ile Tyr Ile Pro Gln Pro Thr Trp Gly Asn His Pro Lys Val
    130                 135                 140

Phe Thr Leu Ala Gly Leu Ser Val Lys Tyr Tyr Arg Tyr Tyr Asp Pro
145                 150                 155                 160

Ala Thr Arg Gly Leu Asp Phe Gln Gly Thr Thr Val Ile Thr Val Leu
                165                 170                 175

Lys Val Leu Gln Leu Tyr Lys His Ser Leu Ser Val Ala Phe Pro Val
            180                 185                 190

Phe Gly Cys Cys Ile Ser Asn Leu Ile Met Asn Pro Val Gly Leu Leu
        195                 200                 205

Asp Asp Leu Ala Ala Ala Pro Ala Gly Ala Ile Val Leu Leu His Ala
    210                 215                 220

Cys Ala His Asn Pro Thr Gly Val Asp Pro Thr Asn Asp Gln Trp Glu
225                 230                 235                 240

Lys Ile Arg Gln Leu Met Arg Ser Lys Gly Leu Leu Pro Phe Phe Asp
                245                 250                 255

Ser Ala Tyr Gln Gly Phe Ala Ser Gly Asn Leu Asp Ala Asp Ala Gln
            260                 265                 270

Ser Val Arg Met Phe Val Ala Asp Gly Gly Glu Cys Leu Ala Ala Gln
        275                 280                 285

Ser Tyr Ala Lys Asn Met Gly Leu Tyr Gly Glu Arg Val Gly Ala Leu
    290                 295                 300

Ser Ile Val Cys Lys Asp Ala Asp Val Ala Ser Arg Val Glu Ser Gln
305                 310                 315                 320

Leu Lys Leu Val Ile Arg Pro Met Tyr Ser Asn Pro Pro Ile His Gly
                325                 330                 335

Ala Ser Ile Val Ala Thr Ile Leu Lys Asp Arg Gln Met Tyr Asp Glu
            340                 345                 350

Trp Thr Ile Glu Leu Lys Ala Met Ala Asp Arg Ile Ile Ser Met Arg
        355                 360                 365

Gln Gln Leu Phe Asp Ala Leu Gln Ala Arg Gly Thr Thr Gly Asp Trp
    370                 375                 380

Ser His Ile Ile Lys Gln Ile Gly Met Phe Thr Phe Thr Gly Leu Asn
385                 390                 395                 400

Thr Glu Gln Val Ser Phe Met Thr Arg Glu His His Ile Tyr Met Thr
                405                 410                 415

Ser Asp Gly Arg Ile Ser Met Ala Gly Leu Ser Ser Arg Thr Ile Pro
            420                 425                 430

His Leu Ala Asp Ala Ile His Ala Ala Val Thr Lys Ala Ala
        435                 440                 445


<210> SEQ ID NO 11
<211> LENGTH: 4176
<212> TYPE: DNA
<213> ORGANISM: Nicotiana tabacum

<400> SEQUENCE: 11

atggcaaatt cctccaattc tgtttttgcc catgttgttc gtgctcctga agatcccatc      60

ttaggagtac ctccctttcc actctttcta ttttacattt ccactgaata tgtttcttct     120
```

```
gtggctcctt taataatctt ccgtaaatat attattagtg gatttgataa gctacttctc    180
tctctctctc tctctctctc tctctctctc tctctctctc tctctctctt ttattttctt    240
attttgggtt agattagaat gaacattaat taatgatcag atgattaggt taaaaatgat    300
atcttggaga tcggcataaa taagttgatt ggaatgatcg ctatagggtt acctattgta    360
tgcattggat catggatgtg tttactaatt atttaatacc tctttctttt tactgtgatc    420
tggcaattcc ttattttatt cctggtgtgg ttgatggaag ggtgtagatt tgattcttta    480
acttgctcta ttgagaagat aatttgttct tctcaagtgt ttagtaatgg tttttttcct    540
gttgtgctac ttcattaaaa caggtcacag ttgcttataa caaagatacc agcccggtga    600
agttgaattt gggtgttggc gcatatcgca ctgaggtctg ccacttctac tttgtctcgt    660
tattctttat tttttatttt ttattataac caaaataagt tgccccttga atggatttgg    720
tcctgctatg ttttgttgaa tccttggtta agtttttctt taataggctc cttcacaagg    780
atacaaaatt gtagacactg atgcatacac attaatattt tttttccctg atgcataatg    840
aagtgaaacc acttgatttt ataagtggtt gtttttttct tcaatcttga gttggatgtt    900
agtgttaagc ttgaaaatta tgttctacta atgcatagtc cgatgacaac ttgcaggaag    960
gaaagcccct tgttcttaat gtggtgagac gagctgaaca aatgctcgtc aatgacacgt   1020
aacttgccaa attagaaact agcttacaga ttttcttttg agatatgatc acctgatgcc   1080
atgattggaa tctaaggctg atatgatgca ggtctcgggt gaaggagtat ctctcaatta   1140
ctggactagc ggattttaac aaactgagtg caaagcttat atttggatct gacaggtttg   1200
gagaattttt ggtgcagttg ctcttgataa atgcttgaat caaaaatata aaaaaatgct   1260
cactatccat gtcgctccag ttaaacctat cttgccaaac cacttgtata aaagaaaatg   1320
agccttcaat attcttcctt ccatctagtt tgatatttga atgagagatt gttgctaaaa   1380
gggaatgctt tatctctaca aagtagagta actgaatacc tgttaaaaca tattcctccg   1440
tatttcatct tattatgatg ccttgcatca gaagaaaatt gttctagagt taactttctc   1500
tcctctttgt tgtactgact ttctgtgtaa ggtgaacgtg atatcaggaa atatgtgtct   1560
tctatcacta ttactccttg ttaagtcata tgtaagatat cagcagattt acttatcttt   1620
agatgtagtt taaatgcttt ttgtgctgtt ttgttgctga tacagccctg ccattcaaga   1680
gaacagggtg actactgttc agtgcttgtc gggcacaggt tctttgaggg ttggggctga   1740
gtttctggct aagcattatc atgaagttag tattccttgc tctctttccc tttatatgtc   1800
taaatcaaat ggacacttct ataagcttct actgtttgtt ttgttgccag catactatat   1860
atataccaca gccaacatgg ggaaaccatc cgaaggtttt cactttagct gggctttcag   1920
taaaatatta tcgttactac gacccagcaa cacgaggcct ggatttccaa ggtactactg   1980
taatcaatgt tcttaaagtt ctacagttgt aagtaagaac cgatttctct ttttcatgga   2040
caagtgaact tgctcctggt cgtgtctaga aagatctata tattatgtgt agctagcaca   2100
ggatctttat ttatttaatt ttgtattctg ttggtaaaga tataagcata gtttatctgt   2160
ggcttctcct gtatttgggt gttgcgtatc aaatttaatc atgaaccctg taggactttt   2220
ggatgatctt gctgctgcac ccgctggagt aatagttctt ctccatgcat gtgctcataa   2280
cccaactggc gttgatccaa caaatgacca gtgggagaaa atcaggcagt tgatgaggtc   2340
caaggggctg ttacctttct ttgacagtgc ttaccaggta aagcttatga tgggattttg   2400
aattcaagtg atacttcgtt aagaatgatt accaaataat ttgaagcccc aaactatgta   2460
ttaatgggct gctcaatgga cccctactat aatgaatatt tttgatattg caggttttg    2520
```

```
ccactggcaa cctagatgca gatgcacaat ctgttcgcat gtttgtggct gatggtggtg   2580
aatgtcttgc agctcagagt tatgccaaaa acatgggact gtatggggag cgtgttggtg   2640
cccttagcat tgtaagtcct tttgtcggtt gtaattgctt tcccttttta ataagcaata   2700
aaattgcttt cccttttaa taagcaatat agcatgatat ccatggctat atcatgctat    2760
ttatgtctaa agatgatttt ttctttggaa gcataattca ggttatattc cctaaaaggc   2820
taaaaagagg ttgttctgtt ggtacaatga acacagtctc tagagatatt gaaagccaat   2880
tttttgaaga tggcttccac ttagattgta attggaaaag aaagagaagg acaaagtgga   2940
attagtaccg gattgtatgt ttaggaaaaa gtgtcgtttt ttttgagttt tatcagacag   3000
gtactaaaag ctgactaaca ctacaataaa attttgtgtt gtgttatagg tttgcaaaga   3060
tgcagatgtt gcaagcagag tcgaaagcca gctaaagctg gttatcaggc caatgtactc   3120
taatccacca attcatggtg cgtctattgt tgctactata ctcaaggaca ggtttgtaca   3180
actatataca agattctgtt ttgttgttag tagatgctat accttctaca ttttgatgtg   3240
gttgctcatc taatggtgat agacaaatgt acgatgaatg gacaattgag ctgaaagcaa   3300
tggccgacag gattattagc atgcgccaac aactctttga tgccttgcaa gctcgaggta   3360
tctgatcttc atatttgttc tttctaggga agcatactgt attctgtatg atgggtttga   3420
ctgctactgc aataggaact ttttctggaa aagtgccagg gtgaaagaac cacggcaact   3480
aaatcttctg acttcattgt tcagtttagt gctaatgtaa gttttattct gttatgcagg   3540
tacagcaggt gattggagtc atatcatcaa acaaattggc atgtttactt tcacaggatt   3600
gaatactgag caagtttcat tcatgactag agagcatcac atttacatga catctgatgg   3660
gtaaggacat ctgactgttg atattttttt ttatttgttt agtttgttac tttgggttgc   3720
tttttctca gtagaaactt aaataattgg aacttagaag cccttatcat tgattatttc    3780
ggcttgaatt ctttaataag gagaatttca gacttatagc ttcagttttg agaggaagca   3840
taaacaagtc cagctctgtc attcatactt aaaatttaca gaagaaagtg cagttctgtt   3900
tttcccccct cccaaattat attgattctc aaaagaactt accttcaatc tatggcacat   3960
ttagtaatct ggtatcagtt gaaacatctc tttgttgaag ttaagatttt ggttaaaaag   4020
atcatcatct ctagtgacat tttctacttt ccatttttag aaggaatgat tttctccttt   4080
ctcatttgca ggagaattag catggcaggc cttagttctc gcacaattcc tcatcttgcc   4140
gatgccatac atgctgctgt taccaaagcg gcctaa                             4176
```

<210> SEQ ID NO 12
<211> LENGTH: 446
<212> TYPE: PRT
<213> ORGANISM: Nicotiana tabacum

<400> SEQUENCE: 12

```
Met Ala Asn Ser Ser Asn Ser Val Phe Ala His Val Val Arg Ala Pro
1               5                   10                  15

Glu Asp Pro Ile Leu Gly Val Thr Val Ala Tyr Asn Lys Asp Thr Ser
            20                  25                  30

Pro Val Lys Leu Asn Leu Gly Val Gly Ala Tyr Arg Thr Glu Glu Gly
        35                  40                  45

Lys Pro Leu Val Leu Asn Val Val Arg Arg Ala Glu Gln Met Leu Val
    50                  55                  60

Asn Asp Thr Ser Arg Val Lys Glu Tyr Leu Ser Ile Thr Gly Leu Ala
65                  70                  75                  80
```

```
Asp Phe Asn Lys Leu Ser Ala Lys Leu Ile Phe Gly Ser Asp Ser Pro
                85                  90                  95

Ala Ile Gln Glu Asn Arg Val Thr Thr Val Gln Cys Leu Ser Gly Thr
            100                 105                 110

Gly Ser Leu Arg Val Gly Ala Glu Phe Leu Ala Lys His Tyr His Glu
        115                 120                 125

His Thr Ile Tyr Ile Pro Gln Pro Thr Trp Gly Asn His Pro Lys Val
    130                 135                 140

Phe Thr Leu Ala Gly Leu Ser Val Lys Tyr Tyr Arg Tyr Tyr Asp Pro
145                 150                 155                 160

Ala Thr Arg Gly Leu Asp Phe Gln Gly Thr Thr Val Ile Asn Val Leu
                165                 170                 175

Lys Val Leu Gln Leu Tyr Lys His Ser Leu Ser Val Ala Ser Pro Val
            180                 185                 190

Phe Gly Cys Cys Val Ser Asn Leu Ile Met Asn Pro Val Gly Leu Leu
        195                 200                 205

Asp Asp Leu Ala Ala Ala Pro Ala Gly Val Ile Val Leu Leu His Ala
    210                 215                 220

Cys Ala His Asn Pro Thr Gly Val Asp Pro Thr Asn Asp Gln Trp Glu
225                 230                 235                 240

Lys Ile Arg Gln Leu Met Arg Ser Lys Gly Leu Leu Pro Phe Phe Asp
                245                 250                 255

Ser Ala Tyr Gln Gly Phe Ala Thr Gly Asn Leu Asp Ala Asp Ala Gln
            260                 265                 270

Ser Val Arg Met Phe Val Ala Asp Gly Gly Glu Cys Leu Ala Ala Gln
        275                 280                 285

Ser Tyr Ala Lys Asn Met Gly Leu Tyr Gly Glu Arg Val Gly Ala Leu
    290                 295                 300

Ser Ile Val Cys Lys Asp Ala Asp Val Ala Ser Arg Val Glu Ser Gln
305                 310                 315                 320

Leu Lys Leu Val Ile Arg Pro Met Tyr Ser Asn Pro Pro Ile His Gly
                325                 330                 335

Ala Ser Ile Val Ala Thr Ile Leu Lys Asp Arg Gln Met Tyr Asp Glu
            340                 345                 350

Trp Thr Ile Glu Leu Lys Ala Met Ala Asp Arg Ile Ile Ser Met Arg
        355                 360                 365

Gln Gln Leu Phe Asp Ala Leu Gln Ala Arg Gly Thr Ala Gly Asp Trp
    370                 375                 380

Ser His Ile Ile Lys Gln Ile Gly Met Phe Thr Phe Thr Gly Leu Asn
385                 390                 395                 400

Thr Glu Gln Val Ser Phe Met Thr Arg Glu His His Ile Tyr Met Thr
                405                 410                 415

Ser Asp Gly Arg Ile Ser Met Ala Gly Leu Ser Ser Arg Thr Ile Pro
            420                 425                 430

His Leu Ala Asp Ala Ile His Ala Ala Val Thr Lys Ala Ala
        435                 440                 445
```

<210> SEQ ID NO 13
<211> LENGTH: 4857
<212> TYPE: DNA
<213> ORGANISM: Nicotiana tabacum

<400> SEQUENCE: 13

```
atggtttcca caatgttctc tctagcttct gccactccgt cagcttcatt ttccttgcaa      60
```

```
gataatctca aggtaatttc atcgtcaatt acattatttg gaaatttgcc ttatcttaga    120
ctattcctaa tgaggtggat tcatgctgtt gtttgtgttt gaacagtcaa agctaaagct    180
ggggactact agccaaagtg ccttttttcgg gaaagacttc gtgaaggcaa aggtaggatt    240
tttgtgttgt ttgtgtacat ttggtgagag gtaatagctc tactgctata gagaaactcc    300
ctgtaggttc tgtcctttag agtatagaag agaaggaaag agtttaattg ggaataatgg    360
tggggatggg atgatttgca tacaattgaa catgtgtttc ttgctttggt atattatgat    420
ataggatgat ccaatcatgc tccgtaaatc aactccagaa cttattattc tttcggcact    480
tactaattat aaaaatcggg ttggagtcct gaaaataagt gattgcctaa ccaacttaca    540
gaactaattt tattatccgt atactcaaat caaaacgaca ttatgccagt actggtttct    600
tgagagggat gatattagtg tagaattatt tataaagttg cagtttaacg tagggtgttt    660
tactaaccag aaaggtgtag atgattccat tcagtttatt agatgctaag aagtataaca    720
gtgaggcctg tgaaacttct ggtagtacca acgattgggg ttttatggcg tttaggaatt    780
tagacattaa ttggcacatt ttagaacgaa aaatatgaca tttaacttac aacagttctt    840
ttctgaataa aatattacta gtaactaatt tgtttgaact ttgccattgc taaaatgtgg    900
ctcaagatct tcttggtact tctatttgta atatcagagt tataggggtc taattctagc    960
tcttgagtcg aaattgttat tagtaaagat aattctttct tgtccccctt cagtgctaac   1020
attctcatct tcacttatgg tattggttta taaaaaattg tgattcagat tataaagtaa   1080
aaaattatgc ctcagtttgt acagcatttt gggttatctg acgttcaatt caacagggtt   1140
ctttaatatc tatttttcta tcttttgtaa tcattgcaac accgagctgt ttaatgtgct   1200
caaaggctat tattagtcct cccactcacc agatccttag aaaaaagccc agaagagaaa   1260
ggcaaagaat acaagcccag accgattgct cgttttataa attttgggaa ttgggatctc   1320
ttttctcata ttcttacttt tttctctttc tttttttcca gtcaaatggc cgtactacta   1380
tgactgttgc tgtgaacgtc tctcgatttg agggaataac tatggctcct cctgacccca   1440
ttcttggagt ttctgaagca ttcaaggctg atacaaatga actgaagctt aaccttggtg   1500
ttggagctta ccgcacggag gagcttcaac catatgtcct caatgttgtt aagaaagtaa   1560
gttcttggtc tcttgtttat gctcaagtag tttgtaaact tttagtcact tggccttgtt   1620
cccatgggtg gataccccttg tccaagggga gtcaatttat tacactctgt aaataggtta   1680
attctttttt aaaatgtatg tatgtatgta tgtatgtatg tatgtataca cacacactat   1740
gttgaatcgc ccctggcttc ttctgtttac ttctatatat tttgtatcca atgggtgaaa   1800
attctggagt gactgcttgt tcctaagcgt tcatcattca ttaactgttt taataacctt   1860
ctataatttt gcatctgaat gatgaggaaa ttgcttttct gtaggcagaa aaccttatgc   1920
tagaaagagg agataacaaa gaggtacttg atttactaaa ttcatctttt ggccttgact   1980
agtgtcactt ggtgccaatt cttacttatt ttttaatcta tggatatata gtatcttcca   2040
atagaaggtt tggctgcatt caacaaagtc acagcagagt tattgtttgg agcagataac   2100
ccagtgattc agcaacaaag ggtaagtatt tttgtttttta actcttagga aaatatatcc   2160
tggaacaaac atgtaaattt ggtctctatg gcctttgttg tgaacgacgt tgtacctttc   2220
gtgatcaggt ggctactatt caaggtctgt caggaactgg gtcattgcgt attgctgcag   2280
cactgataga gcgttacttc cctggctcta aggttttaat atcatctcca acctggggta   2340
cgtagatagt gcttttggat taatttggtt gaatctcatg atactgattt ttacagttat   2400
```

gttttgcagg aaatcataag aacattttca atgatgccag ggtgccttgg tctgaatatc 2460
gatattatga tcccaaaaca gttggcctgg attttgctgg gatgatagaa gatattaagg 2520
ttattatcgt cctcgcattt gtaatctttg tggttgaaat tgtaaagcag cagtgagcac 2580
tgtctttttc ctttctccac aagtcaattg atggtgcctt tgtttgtggc acgtgttttg 2640
actttcagta attgaaggag agatgcgttg ttcattctag aatagcactg tatctcccaa 2700
ttgcattttc tgtttcctgt tcttcctccc tatgtttgca ttgatccatg tctctgctaa 2760
acatggacaa tttgcgccct tggcaatgac atgtgtgttg cttgcttttc ttctctttct 2820
atttcttggt aggagtgact tggttctttc aatgtgagca gtcatatttc tgaaaatgaa 2880
aatcagagga acttgggatg tggaagggat tggcagaaca agtttgataa tgtaattttt 2940
cttgtgagga tggaatatgc aaaaataggc tgcacgcttg ccttttagat ctttggttcc 3000
tatgtcggtt gtgaatgtag atttctattt ttcaacattg tctcgcaagg aaaataggat 3060
tatccagtat tggatgtctt tcctatgttt gatatgtgta tgtgcagtct tgtttgaccg 3120
tcttgctctc ttcccacgtc taaaaagaga gtctgatggg aaagtttttt tccttccagt 3180
tcttgtgcaa gtcattgaca tagtttatgg cattacttgt ttataggctg ctcctgaagg 3240
atcatttatc ttgctccatg gctgtgcgca caacccaact ggtattgatc ccacaattga 3300
acaatgggaa aagattgctg atgtaattca ggagaagaac cacattccat tttttgatgt 3360
cgcctaccag gtaatctgtg ctaaacccaa ttatttcatt tggtgaagct gtaaaatttc 3420
aagtttctta gaagttttga tggttgtgtg tgcgtgtgaa gagaatgaat gatataggaa 3480
ttggttttga aatagtgaaa gatctctcgt atttcatttg ttcttttggt gtgaggagag 3540
tatacattgt tgttttgata gatgggcaaa ttcgatagat gaaggtggtt aagccacgtg 3600
ttactttgta attttttttt gacaccgtca tggtgtttat caataaaatt tactgatttt 3660
tcagtaaagt tattagaaca agataatctg aagtcatttc tattcagaga attgcattga 3720
atagctgtat actataataa tcgagatgcc tcatctgtct acacgctgcc ctacagggat 3780
ttgcaagcgg cagccttgac gaagatgcct catctgtgag attgtttgct gcacgtggca 3840
tggagctttt ggttgctcaa tcatatagta aaaatctggg tctgtatgga gaaaggattg 3900
gagctattaa tgttctttgc tcatccgctg atgcagcgac aaggtacagt cacccgcact 3960
agcaactaca taattgtcct ctgtatagga aaaatgatgc actggaaaac aatggttcca 4020
tatgaaatgc caattacgag atgctgtccc tttgctttga tattgtttac tacaattggt 4080
atctcccatc acctgagcct atggcttgat tggattttat gtgggcgaac caatagaatt 4140
atttgcttaa ttttctcaac taatggatgc atctctgcta actcacaggg tgaaaagcca 4200
gctaaaaagg cttgctcgac caatgtactc aaatccccca attcacggtg ctagaattgt 4260
tgccaatgtc gttggaattc ctgagttctt tgatgaatgg aaacaagaga tggaaatgat 4320
ggcaggaagg ataaagagtg tgagacagaa gctatacgat agcctctcca ccaaggataa 4380
gagtggaaag gactggtcat acattttgaa gcagattgga atgttctcct tcacaggcct 4440
caacaaagct caggtaaatc cccgtgattt aagctattgc ttcatcacaa tatgcttaaa 4500
ttcaatttga tcattcatcg caaagcacat tctgaactca gcacatattt tcattaacac 4560
attctttccg tcctttctga tcaattccat aagtccgata tgcaaaagat agtgcagtga 4620
gagtctctta ctggagtata actagattat cgacaatgca tacatttctt tccctgtacc 4680
tgcacttctg gtgctcatat ttgatctctc ttcttggcca cgcagagcga gaacatgacc 4740
aacaagtggc atgtgtacat gacaaaagac gggaggatat cgttggctgg attatcagct 4800

```
gctaaatgcg aatatcttgc agatgccata attgactcgt actacaatgt cagctaa      4857


<210> SEQ ID NO 14
<211> LENGTH: 462
<212> TYPE: PRT
<213> ORGANISM: Nicotiana tabacum

<400> SEQUENCE: 14

Met Val Ser Thr Met Phe Ser Leu Ala Ser Ala Thr Pro Ser Ala Ser
1               5                   10                  15

Phe Ser Leu Gln Asp Asn Leu Lys Ser Lys Leu Lys Leu Gly Thr Thr
            20                  25                  30

Ser Gln Ser Ala Phe Phe Gly Lys Asp Phe Val Lys Ala Lys Ser Asn
        35                  40                  45

Gly Arg Thr Thr Met Thr Val Ala Val Asn Val Ser Arg Phe Glu Gly
    50                  55                  60

Ile Thr Met Ala Pro Pro Asp Pro Ile Leu Gly Val Ser Glu Ala Phe
65                  70                  75                  80

Lys Ala Asp Thr Asn Glu Leu Lys Leu Asn Leu Gly Val Gly Ala Tyr
                85                  90                  95

Arg Thr Glu Glu Leu Gln Pro Tyr Val Leu Asn Val Val Lys Lys Ala
            100                 105                 110

Glu Asn Leu Met Leu Glu Arg Gly Asp Asn Lys Glu Tyr Leu Pro Ile
        115                 120                 125

Glu Gly Leu Ala Ala Phe Asn Lys Val Thr Ala Glu Leu Leu Phe Gly
    130                 135                 140

Ala Asp Asn Pro Val Ile Gln Gln Gln Arg Val Ala Thr Ile Gln Gly
145                 150                 155                 160

Leu Ser Gly Thr Gly Ser Leu Arg Ile Ala Ala Ala Leu Ile Glu Arg
                165                 170                 175

Tyr Phe Pro Gly Ser Lys Val Leu Ile Ser Ser Pro Thr Trp Gly Asn
            180                 185                 190

His Lys Asn Ile Phe Asn Asp Ala Arg Val Pro Trp Ser Glu Tyr Arg
        195                 200                 205

Tyr Tyr Asp Pro Lys Thr Val Gly Leu Asp Phe Ala Gly Met Ile Glu
    210                 215                 220

Asp Ile Lys Ala Ala Pro Glu Gly Ser Phe Ile Leu Leu His Gly Cys
225                 230                 235                 240

Ala His Asn Pro Thr Gly Ile Asp Pro Thr Ile Glu Gln Trp Glu Lys
                245                 250                 255

Ile Ala Asp Val Ile Gln Glu Lys Asn His Ile Pro Phe Phe Asp Val
            260                 265                 270

Ala Tyr Gln Gly Phe Ala Ser Gly Ser Leu Asp Glu Asp Ala Ser Ser
        275                 280                 285

Val Arg Leu Phe Ala Ala Arg Gly Met Glu Leu Leu Val Ala Gln Ser
    290                 295                 300

Tyr Ser Lys Asn Leu Gly Leu Tyr Gly Glu Arg Ile Gly Ala Ile Asn
305                 310                 315                 320

Val Leu Cys Ser Ser Ala Asp Ala Ala Thr Arg Val Lys Ser Gln Leu
                325                 330                 335

Lys Arg Leu Ala Arg Pro Met Tyr Ser Asn Pro Pro Ile His Gly Ala
            340                 345                 350

Arg Ile Val Ala Asn Val Val Gly Ile Pro Glu Phe Phe Asp Glu Trp
        355                 360                 365
```

```
Lys Gln Glu Met Glu Met Met Ala Gly Arg Ile Lys Ser Val Arg Gln
    370                 375                 380

Lys Leu Tyr Asp Ser Leu Ser Thr Lys Asp Lys Ser Gly Lys Asp Trp
385                 390                 395                 400

Ser Tyr Ile Leu Lys Gln Ile Gly Met Phe Ser Phe Thr Gly Leu Asn
                405                 410                 415

Lys Ala Gln Ser Glu Asn Met Thr Asn Lys Trp His Val Tyr Met Thr
            420                 425                 430

Lys Asp Gly Arg Ile Ser Leu Ala Gly Leu Ser Ala Ala Lys Cys Glu
        435                 440                 445

Tyr Leu Ala Asp Ala Ile Ile Asp Ser Tyr Tyr Asn Val Ser
    450                 455                 460
```

<210> SEQ ID NO 15
<211> LENGTH: 5206
<212> TYPE: DNA
<213> ORGANISM: Nicotiana tabacum
<220> FEATURE:
<221> NAME/KEY: misc_feature
<222> LOCATION: (4436)..(4436)
<223> OTHER INFORMATION: n is a, c, g, or t

<400> SEQUENCE: 15

```
atggcttcca caatgttctc tctagcttct gccgctccat cagcttcatt ttccttgcaa     60

gataatctca aggtaatttc attgtgaatt acattatttg gaaatttgcc ctatcttaga    120

ctgttcctaa tgaggtggat tcatgctgtt gtttgtgttt gaacagtcaa agctaaagct    180

ggggactact agccaaagtg ccttttttcgg gaaagacttc gcgaaggcaa aggtaggatt    240

tttgtgttgt ttgtgtacat ttggtgagag gtaatagctc tactgatata gagcaactcc    300

ctgtaggttc tgtcctttag agtatagaag agaagagaag agtttaattg ggaataatgg    360

tggggatgga atgatttgca tacaaatgaa catgtgtttc ttgcttttgg tgtatgatat    420

aggatgatcc aatcatgctc cgtaaatcaa ctccagaact tattattctt tcggcacttc    480

taattataaa aatctggttg gagtaatgaa tataagtgat tacctaacca acttacagaa    540

ttgattttat tatccatata ctgaaattca aaaacggcgt tttgccagta ctggtttctt    600

gagagggatg atattaatat agaattattt tataaagttg cagtttaacg tagggtattt    660

tactaactag aaaggtgata gatggttccg ttcagtttat tagaagtata acagtgaggc    720

ctgttaaact tttgctagta tcaatgattg gggttttatg gcgtttagga atttagacat    780

caattggcac attttagaac gaaaaacatg acatttaagt tacatcagtt cttttctgaa    840

taaaatagta ctagtaaata acttgtttga actttgccat ttgctaaaat gtggctcaag    900

atcttcttgg tacttctatt tgtaatatca gagttatagg ggtctaattc taccactgtt    960

ttgagtcaaa atgttattag taaagataat tctttcttgt ccccccttcag tgctaacatt   1020

ctcatcttca attatggtat tggtttataa aaaaattgtg cttcagatca ctttataaag   1080

caaaaattat gcctcagttt gtacagcatt ttgggtttta taacattcaa ttcaacaggg   1140

ctctttaata tctatgtttc tactttttgt aatctacatc gagctgttta atgtgctcaa   1200

aggctttaat tagtcctcct actcaccaga tccttagaaa aaagcccaga agagaaaggc   1260

aaagacaacg agctcggaca gattgctcaa tttatattgc aaaaagatcc aaaccctcgg   1320

ggagggagga gcatgaacca aagatgatac attgatatta ttttctaaat ttgggaattg   1380

tgatcttatc ttaaattttt actttttctt ctttttcttt ttttatagtc aaatggtcgg   1440
```

-continued

```
actactatgg ctgtttctgt gaacgtctct cgatttgagg gaataacaat ggctcctcct   1500
gaccccattc ttggagtttc tgaagcattc aaggctgata caaatgaact gaagcttaac   1560
cttggagttg gagcttaccg cacagaagat cttcaaccct atgtcctcaa tgttgttaaa   1620
aaagtaagtc ctcggtctct tgtttatgct caacgtagtt tgtaaactaa gagtcactta   1680
accttgttcc catgtgttcg tcattaaaca tagtaataac tttctatagt tttgcatctg   1740
aatgatgagg aaattacttt tctgtaggca gaaaacctta tgctagagag aggtgacaac   1800
aaagaggtac ttgatatact aaattcatct tttggcctat tagtgtctct tggtgccatt   1860
tcttacttat tttttgtcca tgaatatata gtatcttcca atagaaggtt tggctgcatt   1920
caacaaagtc acagcagagt tattgtttgg agcagataat ccagtgattc agcaacaaag   1980
ggtaagtatt ttggttttta actcttagca aaaaagtatc ctggaacaaa cttgtagatt   2040
cagtttccac ggattgaatg gcattgtatg tttcttgatc aggtggctac tattcaaggt   2100
ctatcaggaa ctgggtcatt gcgtattgct gcagcactga tagagcgtta cttccctggc   2160
tctaaggttt tgatatcatc tccaacctgg ggtacgtata tagtgctttg gattaatttg   2220
gttgaatctc ataatactga tttttgcagt tatgttttgc aggaaatcat aagaacattt   2280
tcaatgatgc cagggtgcct tggtctgaat atcgatatta tgatcccaaa acagttggtc   2340
tagattttgc tgggatgata gaagatataa aggttattat cttcctcact tttgtaatct   2400
ttgtggttga aattgtaaag cagcagtgag cagtgtcttt ttcctttctc cacaagtcca   2460
ttgatggtgc ctttgcatgt gggacatgct ttgactttca gtcgttgaag gagagatgcg   2520
ttattcattc taggatagca ttgtatctcc caaatgcttt ttctgtttcc tgctcttcct   2580
tcccattttt gcatcgatcc tgtctctgct aaacatggac aatttgcgcc cttggcaaat   2640
ggcaatgact tgtgtgttgc ttttcttctc tttctatttt ttggtaggag tgacttggtt   2700
ctttcagtgt gagcagtcat atttctgaaa atgaaaatca gaggaacttg gtgctcacac   2760
ttagagaaag tttgttatgt tttgggatgt gaaaggaatt gacagaacaa gtttgataat   2820
atattttttc ttgtgaggat ggaatatgct aaaaataggc tgcactcttt ccttttagat   2880
ctttagttcc tatgtcggtt gtgaatgtcg atttctattt tcaacatttt ctcacgaaga   2940
aaataggatt atccagtact ggatgtctct cctatgtctg atatatgtgt atgtgcagtc   3000
ttgtttgccc gccttgctct ctccccacgt ctaaaaacag agtctgatgg aaaaggcttt   3060
ttccttccag cttttgtgta agtcattgac atagtttaat gaaactactt gtttataggc   3120
tgctcctgaa ggatcattca tcttgctcca tggctgtgca cacaacccaa ctggtattga   3180
tcccacaatt gaacaatggg aaaagattgc tgatgtaatt caggagaaga accacattcc   3240
atttttttgat gttgcctacc aggtaatctg tgctaaaccc aattattttc atttggtgaa   3300
gttgtagaat tccaagtttc ttagaagttt tgatggctgt gtgtgcgtgt gtgaaaagaa   3360
tgaaagatat aggagatggt ttcaaaatag tgaaagatct ctcgtatttc atttgtcttt   3420
tggtgtgtgg agactataca ttgttgtatt gatagatgag cgaatttgat tgatgttggt   3480
ggttaagcca catgtgttac tttgtccata tttttttaca ccgtcttggt ttttatcaat   3540
gaaatttact gatttttcag tgaaattatt agaacaagat catctgaagt catttctgtt   3600
cagagaattg gattgaatag ctgtatacta taataatcga gatgcctcat ctgtctacac   3660
gctgcactgc agggattcgc aagcggcagc cttgatgaag atgcctcatc tgtgagattg   3720
tttgctgcac gtggcatgga gcttttggtt gctcaatcat atagtaaaaa tctgggtctg   3780
tatggagaaa ggattggagc tattaatgtt ctttgctcat ctgctgatgc agcgacaagg   3840
```

tacaacggcc agcactaata atctacatat ttctcctctg tattggtaaa atgatgttgc 3900
actgaagatt ttggttaatg tatgatgcca tttatttatg ttatgcatgt gcagttcttt 3960
ccgtgtatga tttgttatac aatatagcaa gatgagatgc tttaatctcc tttggatttt 4020
atgtggttga accaatataa cttttcttct gttaatggat gcatatctac taacttacag 4080
ggtgaaaagc cagctaaaaa ggcttgctcg accaatgtac tcaaatcccc ccattcacgg 4140
tgctagaatt gttgccaatg tcgttggaat tcctgagttc tttgatgaat ggaaacaaga 4200
gatggaaatg atggcaggaa ggataaagag tgtgagacag aagctatatg atagcctctc 4260
cgccaaggat aaaagtggaa aggactggtc atacattctg aagcagattg gaatgttctc 4320
cttcacaggc ctcaacaaag ctcaggtaaa accccgtgaa ttaagttatt gctgttgcgg 4380
aagccaaata tatagagagt gattaaatca caactactat atctaaaggt agctangtaa 4440
atgagacaat aataaaatga acaccagaaa ttaatgaggt tcggcaaaat ttgatttttt 4500
gcctagttct cggacacaat caactcaaat ttatttcact ccaaaaatac aaatgaaata 4560
ctacaagaga gaaagaagat tcaaatgcct taggaaataa gaaggcaagt gagagatgtt 4620
tacaaatgaa caaaatcctt gctatttata gaagagaaat ggccttaata atgtcatgca 4680
tgacatcata ttaagtgtga acatgtaatg taaatgcacg aaaaatgcat ctaccaattt 4740
cttaaggctt caaatgttca cactagttca cattaatctt gtcaaaattc aacaattgct 4800
gcatcacaat atgcttaaat tcaatttgat ttggttgaca actttctagc tttgatcatt 4860
catcacaaag cgcattcttc actcagcacg tatttttatt aagacattct ttccttccat 4920
tctgaccgat ttcataagtt aaatatgcaa aagatagtgc agtgagagtc tccttactgg 4980
attataacta tggactaaag ttaaatgcat acatttcttt ccctgtactt gcacttctcg 5040
tgctcatatt tgatatctct tcttggctac acagagcgag aacatgacca acaagtggca 5100
tgtgtacatg acaaaagacg ggaggatatc gttggctgga ttatctgctg ccaaatgtga 5160
atatcttgca gatgccataa ttgactcata ctacaatgtc agctaa 5206

<210> SEQ ID NO 16
<211> LENGTH: 462
<212> TYPE: PRT
<213> ORGANISM: Nicotiana tabacum

<400> SEQUENCE: 16

Met Ala Ser Thr Met Phe Ser Leu Ala Ser Ala Ala Pro Ser Ala Ser
1 5 10 15

Phe Ser Leu Gln Asp Asn Leu Lys Ser Lys Leu Lys Leu Gly Thr Thr
20 25 30

Ser Gln Ser Ala Phe Phe Gly Lys Asp Phe Ala Lys Ala Lys Ser Asn
35 40 45

Gly Arg Thr Thr Met Ala Val Ser Val Asn Val Ser Arg Phe Glu Gly
50 55 60

Ile Thr Met Ala Pro Pro Asp Pro Ile Leu Gly Val Ser Glu Ala Phe
65 70 75 80

Lys Ala Asp Thr Asn Glu Leu Lys Leu Asn Leu Gly Val Gly Ala Tyr
85 90 95

Arg Thr Glu Asp Leu Gln Pro Tyr Val Leu Asn Val Val Lys Lys Ala
100 105 110

Glu Asn Leu Met Leu Glu Arg Gly Asp Asn Lys Glu Tyr Leu Pro Ile
115 120 125

```
Glu Gly Leu Ala Ala Phe Asn Lys Val Thr Ala Glu Leu Leu Phe Gly
    130                 135                 140

Ala Asp Asn Pro Val Ile Gln Gln Gln Arg Val Ala Thr Ile Gln Gly
145                 150                 155                 160

Leu Ser Gly Thr Gly Ser Leu Arg Ile Ala Ala Ala Leu Ile Glu Arg
                165                 170                 175

Tyr Phe Pro Gly Ser Lys Val Leu Ile Ser Ser Pro Thr Trp Gly Asn
            180                 185                 190

His Lys Asn Ile Phe Asn Asp Ala Arg Val Pro Trp Ser Glu Tyr Arg
        195                 200                 205

Tyr Tyr Asp Pro Lys Thr Val Gly Leu Asp Phe Ala Gly Met Ile Glu
    210                 215                 220

Asp Ile Lys Ala Ala Pro Glu Gly Ser Phe Ile Leu Leu His Gly Cys
225                 230                 235                 240

Ala His Asn Pro Thr Gly Ile Asp Pro Thr Ile Glu Gln Trp Glu Lys
                245                 250                 255

Ile Ala Asp Val Ile Gln Glu Lys Asn His Ile Pro Phe Phe Asp Val
            260                 265                 270

Ala Tyr Gln Gly Phe Ala Ser Gly Ser Leu Asp Glu Asp Ala Ser Ser
        275                 280                 285

Val Arg Leu Phe Ala Ala Arg Gly Met Glu Leu Leu Val Ala Gln Ser
    290                 295                 300

Tyr Ser Lys Asn Leu Gly Leu Tyr Gly Glu Arg Ile Gly Ala Ile Asn
305                 310                 315                 320

Val Leu Cys Ser Ser Ala Asp Ala Ala Thr Arg Val Lys Ser Gln Leu
                325                 330                 335

Lys Arg Leu Ala Arg Pro Met Tyr Ser Asn Pro Pro Ile His Gly Ala
            340                 345                 350

Arg Ile Val Ala Asn Val Val Gly Ile Pro Glu Phe Phe Asp Glu Trp
        355                 360                 365

Lys Gln Glu Met Glu Met Met Ala Gly Arg Ile Lys Ser Val Arg Gln
    370                 375                 380

Lys Leu Tyr Asp Ser Leu Ser Ala Lys Asp Lys Ser Gly Lys Asp Trp
385                 390                 395                 400

Ser Tyr Ile Leu Lys Gln Ile Gly Met Phe Ser Phe Thr Gly Leu Asn
                405                 410                 415

Lys Ala Gln Ser Glu Asn Met Thr Asn Lys Trp His Val Tyr Met Thr
            420                 425                 430

Lys Asp Gly Arg Ile Ser Leu Ala Gly Leu Ser Ala Ala Lys Cys Glu
        435                 440                 445

Tyr Leu Ala Asp Ala Ile Ile Asp Ser Tyr Tyr Asn Val Ser
    450                 455                 460
```

```
<210> SEQ ID NO 17
<211> LENGTH: 101
<212> TYPE: DNA
<213> ORGANISM: Artificial Sequence
<220> FEATURE:
<223> OTHER INFORMATION: Nucleotide sequence used to generate AAT2S/T
      RNAi plants

<400> SEQUENCE: 17

gctattcaag agaacagagt aacaactgtg cagtgcttgt ctggcacagg ctcattgagg     60

gttggagctg aatttttggc tcgacattat catcaacgca c                        101
```

MODULATING AMINO ACID CONTENT IN A PLANT

This application is a U.S. National Stage Application of International Application No. PCT/EP2019/057707 filed Mar. 27, 2019, which was published in English on Oct. 3, 2019, as International Publication No. WO 2019/185703 A1. International Application No. PCT/EP2019/057707 claims priority to European Application No. 18164766.0 filed Mar. 28, 2018.

FIELD OF THE INVENTION

The present invention discloses the polynucleotide sequences of genes encoding aspartate transaminase (AAT) from *Nicotiana tabacum* and variants, homologues and fragments thereof. The polypeptide sequences encoded thereby and variants, homologues and fragments thereof are also disclosed. The modulation of the expression of the one or more NtAAT genes or the function or activity of the NtAAT polypeptide(s) encoded thereby to modulate the levels of one or more free amino acids—such as aspartate—and metabolites or by-products derived therefrom—such as ammonia—in a plant or part thereof is also disclosed.

BACKGROUND

Acrylamide is a chemical compound of formula $C_3H_5NO$ (IUPAC name is prop-2-enamide) and concerns have been raised regarding its potential toxicity. The origin of acrylamide in the aerosol of smoking articles comprising tobacco may be, at least in part, from amino acids which are present in tobacco material used for the production of smoking articles. Cultivated tobacco types exhibit an increase in total free amino acids during curing, particularly air-cured tobacco types and sun-cured tobacco types. Variation in amino acid content in cured tobacco material is related to the time of curing at ambient temperature (air-curing) as compared to flue-curing (which is a fast drying process) allowing enzymatic reactions to be still active 10-15 days after harvest. In addition, air-cured tobacco material exhibits higher water content than other cured tobaccos, slowing down the drying process at ambient temperature, thereby being considered to be a second factor allowing some enzymatic reaction to be still active later in the curing phase. It is desirable to decrease the levels of amino acids and metabolites and by-products derived therefrom in plants, especially in cured plant material and smoke and aerosol derived therefrom. As ammonia is likely to be a by-product of amino acids produced during curing, the level of ammonia in cured leaves, smoke and aerosol may also be decreased. It is also desirable to decrease the formation of undesirable odours in aerosol or smoke when the tobacco is heated or burned.

The present invention seeks to address this need in the art.

SUMMARY OF THE INVENTION

A number of polynucleotide sequences encoding AAT from *Nicotiana tabacum* are described herein that are involved in amino acid biosynthesis during early curing. Changes in NtATT genes that are not over-expressed during curing will not contribute to modulating levels of amino acid levels and metabolites derived therefrom. However, these genes are likely to be involved in other metabolic pathways and changes in their expression could result in a phenotype that is detrimental agronomically (for example, slow growth). Knowing which NtAAT genes are over-expressed during curing advantageously allows for the selection of plants with changes in only the relevant genes and reduces potential negative effects on other metabolic processes.

AAT catalyses the reversible transfer of the α-amino group between aspartate and glutamate, being therefore a key enzyme in amino acid metabolism by channeling nitrogen from glutamate and aspartate. The synthesis of aspartate is essential for the synthesis of other amino acids like asparagine, threonine, isoleucine, cysteine and methionine. During the curing process, aspartate is converted to asparagine via asparagine synthetase. Asparagine and glutamine are key compounds for N-remobilization in senescent leaves, asparagine being the major amino acid produced in Burley cured leaves. Asparagine is known to result in acrylamide upon heating of tobacco leaf. Aspartate is also key in the biosynthesis of other amino acids—such as threonine, methionine and cysteine—some of which result in a sulphur-odor upon heating. By modulating the expression and/or activity of the disclosed AAT it is now possible to alter the chemistry of plant parts—such as leaves—and the smoke or aerosols derived therefrom. Interestingly, some AAT tobacco genes may still be expressed at least 8 days from the onset of the air-curing process, as described herein. For example, the amount of one or more amino acids—such as aspartate and metabolites derived therefrom—such as ammonia—during and after curing can be modulated and hence the formation of acrylamide formed during heating of tobacco can be modulated, suitably, reduced. By way of further example, the formation of other amino acids which can result in a sulphur-odour upon heating of tobacco can also be modulated, suitably, reduced. Several AAT genomic polynucleotide sequences from *Nicotiania tabacum* are described herein, including NtAAT1-S(SEQ ID NO: 5), NtAAT1-T (SEQ ID NO: 7), NtAAT2-S(SEQ ID NO: 1), NtAAT2-T (SEQ ID NO: 3), NtAAT3-S(SEQ ID NO: 9), NtAAT3-T (SEQ ID NO: 11), NtAAT4-S(SEQ ID NO: 13) and NtAAT4-T (SEQ ID NO: 15). The corresponding deduced polypeptide sequences for NtAAT1-S(SEQ ID NO: 6), NtAAT1-T (SEQ ID NO: 8), NtAAT2-S(SEQ ID NO: 2), NtAAT2-T (SEQ ID NO: 4), NtAAT3-S(SEQ ID NO: 10), NtAAT3-T (SEQ ID NO: 12), NtAAT4-S(SEQ ID NO: 14) and NtAAT4-T (SEQ ID NO: 16) are also disclosed. NtAAT2-S and NtAAT2-T, and to a lesser extent NtAAT1-S, NtAAT1-T, are shown to play a particular role in aspartate biosynthesis during curing. In contrast, NtAAT4-S and NtAAT4-T transcripts are down-regulated mainly during the first two days of leaf curing, although NtAAT4-T remains expressed after eight days of air-curing, so the involvement of the NtAAT4-T protein in curing cannot be excluded. The expression of NtAAT3-S remains low during leaf curing and is not modulated during the yellowing phase. NtAAT3-T is sometimes slightly induced during curing, however the expression level remains comparatively low.

SOME ADVANTAGES

Advantageously, NtAAT polynucleotide sequences can be highly expressed during curing, particularly from the onset of curing. Modulating the expression of one or more NtAAT polynucleotide sequences can result in modulated levels of acrylamide in aerosol since the level of aspartate can be modulated throughout the curing process. In particular, decreasing the expression of one or more NtAAT polynucleotide sequences can result in decreased levels of acrylamide in aerosol.

Since aspartate is key in the biosynthesis of other amino acids—such as threonine, methionine and cysteine—some of which result in a sulphur-odor upon heating—modulating the expression of NtAAT polynucleotide sequences can modulate this undesirable odor. In addition, knowing that ammonia is likely to be a by-product of amino acids produced during curing, decreasing the expression of NtAAT polynucleotide sequences and/or the activity of the protein encoded thereby may decrease the level of ammonia in cured plant material and smoke and aerosol derived therefrom. The increase in amino acids occurs particularly in air-cured tobacco and sun-cured tobacco as these curing methods result in elevated amino acid content in cured tobacco material as compared to flue-cured tobacco material. The present disclosure is therefore particularly applicable to air-cured and flue-cured tobacco material.

Advantageously, there is limited impact on levels of nicotine in the modified plants described herein, which is desirable when the modified plants are intended to be used for the production of tobacco plants and consumed tobacco products.

Advantageously, non-genetically modified plants can be created which may be more acceptable to consumers.

Advantageously, the present disclosure is not restricted to the use of EMS mutant plants. An EMS mutant plant can have less potential to bring improved properties to a crop after breeding. Once breeding is started, the desirable characteristic(s) of the EMS mutant plant can be lost for different reasons. For example, several mutations may be required, the mutation can be dominant or recessive, and the identification of a point mutation in a gene target can be difficult to reach. In contrast, the present disclosure exploits the use of NtAAT polynucleotides that can be specifically manipulated to produce plants with a desirable phenotype. The disclosure may be applied to various plant varieties or crops.

In one aspect, there is described a plant cell comprising: (i) a polynucleotide comprising, consisting or consisting essentially of a sequence having at least 80% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15; (ii) a polypeptide encoded by the polynucleotide set forth in (i); (iii) a polypeptide comprising, consisting or consisting essentially of a sequence having at least 95% sequence identity to SEQ ID NO: 6 or SEQ ID No: 8, at least 93% sequence identity to SEQ ID NO: 2 or SEQ ID No: 4 or SEQ ID NO: 10 or SEQ ID No: 12, or at least 94% sequence identity to SEQ ID NO: 14 or SEQ ID NO: 16; or (iv) a construct, vector or expression vector comprising the isolated polynucleotide set forth in (i), wherein said plant cell comprises at least one modification which modulates the expression or activity of the polynucleotide or the polypeptide as compared to a control plant cell in which the expression or activity of the polynucleotide or polypeptide has not been modified.

In another aspect, there is disclosed a plant cell comprising: (i) a polynucleotide comprising, consisting or consisting essentially of a sequence having at least 80% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15; (ii) a polypeptide encoded by the polynucleotide set forth in (i); (iii) a polypeptide comprising, consisting or consisting essentially of a sequence having at least 95% sequence identity to SEQ ID NO: 6 or SEQ ID No: 8, at least 93% sequence identity to SEQ ID NO: 2 or SEQ ID NO: 10 or SEQ ID No: 12, or at least 94% sequence identity to SEQ ID NO: 4 or SEQ ID NO: 14 or SEQ ID NO: 16; or (iv) a construct, vector or expression vector comprising the isolated polynucleotide set forth in (i), wherein said plant cell comprises at least one modification which modulates the expression or activity of the polynucleotide or the polypeptide as compared to a control plant cell in which the expression or activity of the polynucleotide or polypeptide has not been modified. Suitably, said plant cell comprises a polynucleotide comprising, consisting or consisting essentially of a sequence having at least 80% sequence identity to SEQ ID NO: 5, SEQ ID NO: 7, SEQ ID NO: 1 or SEQ ID NO: 3, suitably, wherein the plant cell comprises a polynucleotide comprising, consisting or consisting essentially of a sequence having at least 80% sequence identity to SEQ ID NO: 1 or SEQ ID NO: 3.

Suitably, said plant cell comprises a polypeptide comprising, consisting or consisting essentially of a sequence having at least 95% sequence identity to SEQ ID NO: 6 or SEQ ID No: 8 or at least 93% sequence identity to SEQ ID NO: 2 or SEQ ID No: 4, suitably, wherein the plant cell comprises a polypeptide comprising, consisting or consisting essentially of a sequence having at least 93% sequence identity to SEQ ID NO: 2 or SEQ ID No: 4.

Suitably, said plant cell comprises a polypeptide comprising, consisting or consisting essentially of a sequence having at least 95% sequence identity to SEQ ID NO: 6 or SEQ ID No: 8 or at least 93% sequence identity to SEQ ID NO: 2, or at least 94% sequence identity to or SEQ ID No: 4, suitably, wherein the plant cell comprises a polypeptide comprising, consisting or consisting essentially of a sequence having at least 93% sequence identity to SEQ ID NO: 2 or at least 94% sequence identity to SEQ ID No: 4. Suitably, the expression and/or activity of one or more of NtAAT1-S(SEQ ID NO: 5 or SEQ ID NO: 6), NtAAT1-T (SEQ ID NO: 7 or SEQ ID NO: 8), NtAAT2-S(SEQ ID NO: 1 or SEQ ID NO: 2) and NtAAT2-T (SEQ ID NO: 3 or SEQ ID NO: 4) is modulated whereas the expression and/or activity of one or more of NtAAT3-S(SEQ ID NO: 9 or SEQ ID NO: 10), NtAAT3-T (SEQ ID NO: 11 or SEQ ID NO: 12), NtAAT4-S(SEQ ID NO: 13 or SEQ ID NO: 14) and NtAAT4-T (SEQ ID NO: 15 or SEQ ID NO: 16) is not modulated.

Suitably, the at least one modification is a modification of the plant cell's genome, or a modification of the construct, vector or expression vector, or a transgenic modification.

Suitably, the modification of the plant cell's genome, or the modification of the construct, vector, or expression vector is a mutation or edit.

Suitably, the modification decreases the expression or activity of the polynucleotide or the polypeptide as compared to the control plant cell.

Suitably, the plant cell comprises an interference polynucleotide comprising a sequence that is at least 80% complementary to at least 19 nucleotides of an RNA transcribed from the polynucleotide of claim 1(i).

Suitably, the modulated expression or activity of the polynucleotide or the polypeptide modulates the level of amino acids in cured or dried leaf derived from the plant cell as compared to the level of amino acids in cured or dried leaf derived from a control plant, suitably wherein the amino acid is aspartate or a metabolite derived therefrom.

Suitably, the level of nicotine in cured or dried leaf from the plant cell is substantially the same as the level of nicotine in cured or dried leaf of a control plant cell; and/or wherein the level of acrylamide in cured or dried leaf derived from the plant cell is decreased as compared to the level of acrylamide in cured or dried leaf derived from a control plant and/or wherein the level of ammonia in cured or dried leaf derived from the plant cell is decreased as compared to the level of amino acids in cured or dried leaf derived from a control plant.

In a further aspect, there is described a plant or part thereof comprising the plant cell described herein. In a further aspect, there is described a plant or part thereof as described herein, wherein the amount of aspartate or metabolite derived therefrom is modified in at least a part of the plant as compared to a control plant or part thereof.

In a further aspect, there is described plant material, cured plant material, or homogenized plant material, derived from the plant or part thereof as described herein, suitably, wherein the cured plant material is air-cured or sun-cured or flue-cured plant material.

In a further aspect, there is described plant material as described herein, comprising biomass, seed, stem, flowers, or leaves from the plant or part thereof as described herein.

In a further aspect, there is described a tobacco product comprising the plant cell as described herein, a part of the plant as described herein or the plant material as described herein.

In a further aspect, there is described a method for producing the plant as described herein, comprising the steps of: (a) providing a plant cell comprising a polynucleotide comprising, consisting or consisting essentially of a polynucleotide comprising, consisting or consisting essentially of a sequence having at least 80% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15; (b) modifying the plant cell to modulate the expression of said polynucleotide as compared to a control plant cell; and (c) propagating the plant cell into a plant.

Suitably, step (c) comprises cultivating the plant from a cutting or seedling comprising the plant cell.

Suitably, the step of modifying the plant cell comprises modifying the genome of the cell by genome editing or genome engineering.

Suitably, the genome editing or genome engineering is selected from CRISPR/Cas technology, zinc finger nuclease-mediated mutagenesis, chemical or radiation mutagenesis, homologous recombination, oligonucleotide-directed mutagenesis and meganuclease-mediated mutagenesis.

Suitably, the step of modifying the plant cell comprises transfecting the cell with a construct comprising a polynucleotide comprising, consisting, or consisting essentially of a sequence having at least 80% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15 operably linked to a constitutive promoter.

Suitably, the step of modifying the plant cell comprises introducing an interference polynucleotide comprising a sequence that is at least 80% complementary to an RNA transcribed from the polynucleotide of claim 1(i) into the cell.

Suitably, the plant cell is transfected with a construct expressing an interference polynucleotide comprising a sequence that is at least 80% complementary to at least 19 nucleotides of an RNA transcribed from the polynucleotide of claim 1(i).

In a further aspect, there is described a method for producing cured plant material with an altered amount of aspartate or metabolite derived therefrom as compared to control plant material, comprising the steps of: (a) providing a plant or part thereof or the plant material as described herein; (b) optionally harvesting the plant material therefrom; and (c) curing the plant material.

Suitably, the plant material comprises cured leaves, cured stems or cured flowers, or a mixture thereof.

Suitably, the curing method is selected from the group consisting of air curing, fire curing, smoke curing, and flue curing.

DETAILED DESCRIPTION

Figure 1:
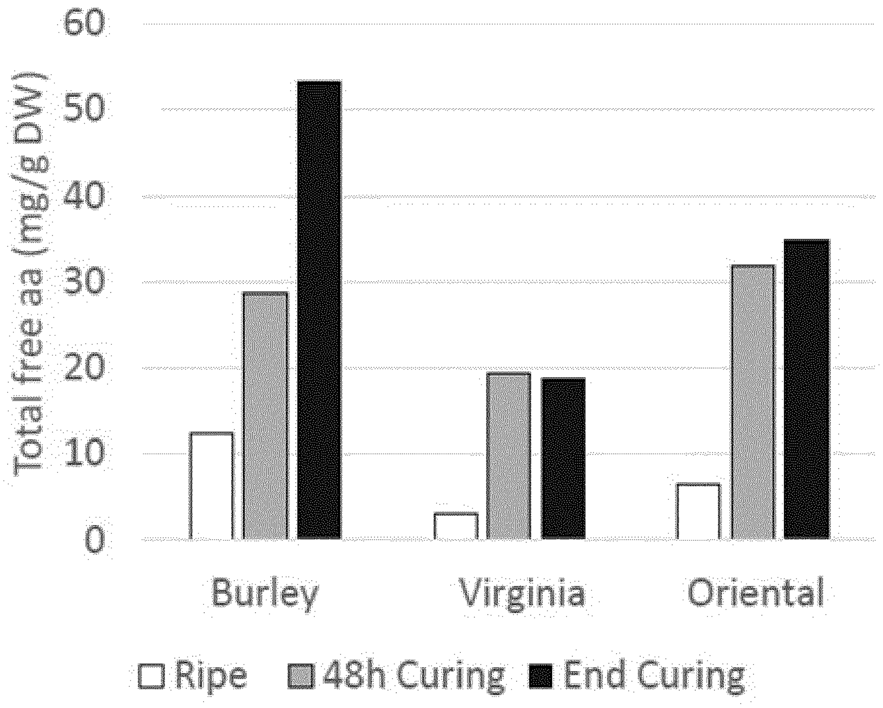
FIG. 1 is a graph showing the content of total free amino acids after harvest (ripe), after two days of curing (48 h) and at the end of curing in Virginia, Burley and Oriental cultivated tobacco.

Section headings as used in this disclosure are for organisation purposes and are not intended to be limiting.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. The materials, methods, and examples disclosed herein are illustrative only and not intended to be limiting.

The terms “comprise(s),” “include(s),” “having,” “has,” “can,” “contain(s),” and variants thereof, as used herein, are intended to be open-ended transitional phrases, terms, or words that do not preclude the possibility of additional acts or structures.

The singular forms “a,” “and” and “the” include plural references unless the context clearly dictates otherwise.

The term “and/or” means (a) or (b) or both (a) and (b).

The present disclosure contemplates other embodiments “comprising,” “consisting of” and “consisting essentially of” the embodiments or elements presented herein, whether explicitly set forth or not.

For the recitation of numerical ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated. As used throughout the specification and the claims, the following terms have the following meanings:

“Coding sequence” or “polynucleotide encoding” means the nucleotides (RNA or DNA molecule) that comprise a polynucleotide which encodes a polypeptide. The coding sequence can further include initiation and termination signals operably linked to regulatory elements including a promoter and polyadenylation signal capable of directing expression in the cells of an individual or mammal to which the polynucleotide is administered. The coding sequence may be codon optimized.

"Complement" or "complementary" can mean Watson-Crick (for example, A-T/U and C-G) or Hoogsteen base pairing between nucleotides or nucleotide analogs. "Complementarity" refers to a property shared between two polynucleotides, such that when they are aligned antiparallel to each other, the nucleotide bases at each position will be complementary.

"Construct" refers to a double-stranded, recombinant polynucleotide fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

The term "control" in the context of a control plant or control plant cells means a plant or plant cells in which the expression, function or activity of one or more genes or polypeptides has not been modified (for example, increased or decreased) and so it can provide a comparison with a plant in which the expression, function or activity of the same one or more genes or polypeptides has been modified. As used herein, a "control plant" is a plant that is substantially equivalent to a test plant or modified plant in all parameters with the exception of the test parameters. For example, when referring to a plant into which a polynucleotide has been introduced, a control plant is an equivalent plant into which no such polynucleotide has been introduced. A control plant can be an equivalent plant into which a control polynucleotide has been introduced. In such instances, the control polynucleotide is one that is expected to result in little or no phenotypic effect on the plant. The control plant may comprise an empty vector.

The control plant may correspond to a wild-type plant. The control plant may be a null segregant wherein the T1 segregant no longer possesses the transgene.

"Donor DNA" or "donor template" refers to a double-stranded DNA fragment or molecule that includes at least a portion of the gene of interest. The donor DNA may encode a fully-functional polypeptide or a partially-functional polypeptide.

"Endogenous gene or polypeptide" refers to a gene or polypeptide that originates from the genome of an organism and has not undergone a change, such as a loss, gain, or exchange of genetic material. An endogenous gene undergoes normal gene transmission and gene expression. An endogenous polypeptide undergoes normal expression.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms including increasing transcriptional efficiency, stabilization of mature mRNA and translational enhancement.

"Expression" refers to the production of a functional product. For example, expression of a polynucleotide fragment may refer to transcription of the polynucleotide fragment (for example, transcription resulting in mRNA or functional RNA) and/or translation of mRNA into a precursor or mature polypeptide. "Overexpression" refers to the production of a gene product in transgenic organisms that exceeds levels of production in a null segregating (or non-transgenic) organism from the same experiment.

"Functional" and "full-functional" describes a polypeptide that has biological function or activity. A "functional gene" refers to a gene transcribed to mRNA, which is translated to a functional or active polypeptide.

"Genetic construct" refers to DNA or RNA molecules that comprise a polynucleotide that encodes a polypeptide. The coding sequence can include initiation and termination signals operably linked to regulatory elements including a promoter and polyadenylation signal capable of directing expression.

"Genome editing" refers to changing an endogenous gene that encodes an endogenous polypeptide, such that polypeptide expression of a truncated endogenous polypeptide or an endogenous polypeptide having an amino acid substitution is obtained. Genome editing can include replacing the region of the endogenous gene to be targeted or replacing the entire endogenous gene with a copy of the gene that has a truncation or an amino acid substitution with a repair mechanism—such as HDR. Genome editing may also include generating an amino acid substitution in the endogenous gene by generating a double stranded break in the endogenous gene that is then repaired using NHEJ. NHEJ may add or delete at least one base pair during repair which may generate an amino acid substitution. Genome editing may also include deleting a gene segment by the simultaneous action of two nucleases on the same DNA strand in order to create a truncation between the two nuclease target sites and repairing the DNA break by NHEJ.

"Heterologous" with respect to a sequence means a sequence that originates from a foreign species, or, if from the same species, is substantially modified from its native form in composition and/or genomic locus by deliberate human intervention.

"Homology-directed repair" or "HDR" refers to a mechanism in cells to repair double strand DNA lesions when a homologous piece of DNA is present in the nucleus, mostly in G2 and S phase of the cell cycle. HDR uses a donor DNA or donor template to guide repair and may be used to create specific sequence changes to the genome, including the targeted addition of whole genes. If a donor template is provided along with the site specific nuclease, then the cellular machinery will repair the break by homologous recombination, which is enhanced several orders of magnitude in the presence of DNA cleavage. When the homologous DNA piece is absent, NHEJ may take place instead.

The terms "homology" or "similarity" refer to the degree of sequence similarity between two polypeptides or between two polynucleotide molecules compared by sequence alignment. The degree of homology between two discrete polynucleotides being compared is a function of the number of identical, or matching, nucleotides at comparable positions.

"Identical" or "identity" in the context of two or more polynucleotides or polypeptides means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be determined manually or by using a computer sequence algorithm such as ClustalW, ClustalX, BLAST, FASTA or Smith-Waterman. The popular multiple alignment program ClustalW (*Nucleic Acids Research* (1994) 22, 4673-4680; *Nucleic Acids Research* (1997), 24, 4876-4882) is a suitable way for generating multiple alignments of polypeptides or polynucleotides. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10. o, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

The term "increase" or "increased" refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, at least 100%, at least 150%, or at least 200% or more or more of a quantity or a function or an activity, such as but not limited to polypeptide function or activity, transcriptional function or activity, and/or polypeptide expression. The term "increased," or the phrase "an increased amount" can refer to a quantity or a function or an activity in a modified plant or a product generated from the modified plant that is more than what would be found in a plant or a product from the same variety of plant processed in the same manner, which has not been modified. Thus, in some contexts, a wild-type plant of the same variety that has been processed in the same manner is used as a control by which to measure whether an increase in quantity is obtained.

The term "decrease" or "decreased" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or, or at least 150%, or at least 200% more of a quantity or a function—such as polypeptide function, transcriptional function, or polypeptide expression. The term "increased," or the phrase "an increased amount" can refer to a quantity or a function in a modified plant or a product generated from the modified plant that is less than what would be found in a plant or a product from the same variety of plant processed in the same manner, which has not been modified. Thus, in some contexts, a wild-type plant of the same variety that has been processed in the same manner is used as a control by which to measure whether a reduction in quantity is obtained.

The term "inhibit" or "inhibited" refers to a reduction of from about 98% to about 100%, or a reduction of at least 98%, at least 99%, but particularly of 100%, of a quantity or a function or an activity, such as but not limited to polypeptide function or activity, transcriptional function or activity, and/or polypeptide expression.

The term "introduced" means providing a polynucleotide (for example, a construct) or polypeptide into a cell. Introduced includes reference to the incorporation of a polynucleotide into a eukaryotic cell where the polynucleotide may be incorporated into the genome of the cell, and includes reference to the transient provision of a polynucleotide or polypeptide to the cell. Introduced includes reference to stable or transient transformation methods, as well as sexually crossing. Thus, "introduced" in the context of inserting a polynucleotide (for example, a recombinant construct/expression construct) into a cell, means "transfection" or "transformation" or "transduction" and includes reference to the incorporation of a polynucleotide into a eukaryotic cell where the polynucleotide may be incorporated into the genome of the cell (for example, chromosome, plasmid, plastid or mitochondrial DNA), converted into an autonomous replicon, or transiently expressed (for example, transfected mRNA).

The terms "isolated" or "purified" refer to material that is substantially or essentially free from components that normally accompany it as found in its native state. Purity and homogeneity are typically determined using analytical chemistry techniques such as polyacrylamide gel electrophoresis or high performance liquid chromatography. A polypeptide that is the predominant species present in a preparation is substantially purified. In particular, an isolated polynucleotide is separated from open reading frames that flank the desired gene and encode polypeptides other than the desired polypeptide. The term "purified" as used herein denotes that a polynucleotide or polypeptide gives rise to essentially one band in an electrophoretic gel. Particularly, it means that the polynucleotide or polypeptide is at least 85% pure, more preferably at least 95% pure, and most preferably at least 99% pure. Isolated polynucleotides may be purified from a host cell in which they naturally occur. Conventional polynucleotide purification methods known to skilled artisans may be used to obtain isolated polynucleotides. The term also embraces recombinant polynucleotides and chemically synthesized polynucleotides.

"Modulate" or "modulating" refers to causing or facilitating a qualitative or quantitative change, alteration, or modification in a process, pathway, function or activity of interest. Without limitation, such a change, alteration, or modification may be an increase or decrease in the relative process, pathway, function or activity of interest. For example, gene expression or polypeptide expression or polypeptide function or activity can be modulated. Typically, the relative change, alteration, or modification will be determined by comparison to a control.

"Non-homologous end joining (NHEJ) pathway" as used herein refers to a pathway that repairs double-strand breaks in DNA by directly ligating the break ends without the need for a homologous template. The template-independent religation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

The term 'non-naturally occurring' describes an entity—such as a polynucleotide, a genetic mutation, a polypeptide, a plant, a plant cell and plant material—that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using traditional plant breeding techniques—such as back-crossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. In certain embodiments, a mutation is not a naturally occurring mutation that exists naturally in a polynucleotide or a polypeptide—such as a gene or a polypeptide. Differences in genetic background can be detected by phenotypic differences or by molecular biology techniques known in the art—such as polynucleotide sequencing, presence or absence of genetic markers (for example, microsatellite RNA markers).

"Oligonucleotide" or "polynucleotide" means at least two nucleotides covalently linked together. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a given sequence under stringent hybridization conditions. Thus, a polynucleotide also encompasses a probe that hybridizes under stringent hybridization conditions. Polynucleotides may be single stranded or double stranded, or may contain portions of both double stranded and single stranded sequence. The polynucleotide may be DNA, both genomic and cDNA, RNA, or a hybrid, where the polynucleotide may contain combinations of deoxyribo- and ribo-nucleotides, and combinations of bases including uracil, adenine, thymine, cytosine, guanine, inosine, xanthine hypoxanthine, isocytosine and isoguanine. Polynucleotides may be obtained by chemical synthesis methods or by recombinant methods.

The specificity of single-stranded DNA to hybridize complementary fragments is determined by the "stringency" of the reaction conditions (Sambrook et al., Molecular Cloning and Laboratory Manual, Second Ed., Cold Spring Harbor (1989)). Hybridization stringency increases as the propensity to form DNA duplexes decreases. In polynucleotide hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments. DNA duplexes are stabilised by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions. To hybridize under "stringent conditions" describes hybridization protocols in which polynucleotides at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the given sequence hybridize to the given sequence at equilibrium. Since the given sequences are generally present at excess, at Tm, 50% of the probes are occupied at equilibrium.

"Stringent hybridization conditions" are conditions that enable a probe, primer, or oligonucleotide to hybridize only to its specific sequence. Stringent conditions are sequence-dependent and will differ. Stringent conditions typically comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, for example, 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Suitably, the conditions are such that sequences at least about 65%, 70%, 75%, 85%, 90%, 95%, 98%, or 99% homologous to each other typically remain hybridized to each other.

"Moderately stringent conditions" use washing solutions and hybridization conditions that are less stringent, such that a polynucleotide will hybridize to the entire, fragments, derivatives, or analogs of the polynucleotide. One example comprises hybridization in 6×SSC, 5×Denhardt's solution, 0.5% SDS and 100 μg/mL denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (see Ausubel et al., Current Protocols in Molecular Biology, Volumes 1-3, John Wiley & Sons, Inc., Hoboken, N.J. (1993); Kriegler, Gene Transfer and Expression: A Laboratory Manual, Stockton Press, New York, N.Y. (1990); Perbal, A Practical Guide to Molecular Cloning, 2nd edition, John Wiley & Sons, New York, N.Y. (1988)).

"Low stringent conditions" use washing solutions and hybridization conditions that are less stringent than those for moderate stringency, such that a polynucleotide will hybridize to the entire, fragments, derivatives, or analogs of the polynucleotide. A non-limiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 μg/mL denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (see Ausubel et al., 1993; Kriegler, 1990).

"Operably linked" means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. "Operably linked" refers to the association of polynucleotide fragments in a single fragment so that the function of one is regulated by the other. For example, a promoter is operably linked with a polynucleotide fragment when it is capable of regulating the transcription of that polynucleotide fragment.

The term "plant" refers to any plant at any stage of its life cycle or development, and its progenies. In one embodiment, the plant is a tobacco plant, which refers to a plant belonging to the genus *Nicotiana*. The term includes reference to whole plants, plant organs, plant tissues, plant propagules, plant seeds, plant cells and progeny of same. Plant cells include, without limitation, cells from seeds, suspension cultures, embryos, meristematic regions, callus tissue, leaves, roots, shoots, gametophytes, sporophytes, pollen, and microspores. Suitable species, cultivars, hybrids and varieties of tobacco plant are described herein.

"Polynucleotide", "polynucleotide sequence" or "polynucleotide fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. A polynucleotide can be, without limitation, a genomic DNA, complementary DNA (cDNA), mRNA, or antisense RNA or a fragment(s) thereof. Moreover, a polynucleotide can be single-stranded or double-stranded, a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid (PNA). Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, the polynucleotides include their corresponding RNA sequences, and their complementary (for example, completely complementary) DNA or RNA sequences, including the reverse complements thereof. The polynucleotides of the present disclosure are set forth in the accompanying sequence listing.

"Polypeptide" or "polypeptide sequence" refer to a polymer of amino acids in which one or more amino acid residues is an artificial chemical analogue of a corresponding naturally occurring amino acid, as well as to naturally occurring polymers of amino acids. The terms are also inclusive of modifications including, but not limited to, glycosylation, lipid attachment, sulfation, gamma-carboxylation of glutamic acid residues, hydroxylation and ADP-ribosylation. The polypeptides of the present disclosure are set forth in the accompanying sequence listing.

"Promoter" means a synthetic or naturally-derived molecule which is capable of conferring, activating or enhancing expression of a polynucleotide in a cell. The term refers to a polynucleotide element/sequence, typically positioned upstream and operably-linked to a double-stranded polynucleotide fragment. Promoters can be derived entirely from regions proximate to a native gene of interest, or can be composed of different elements derived from different native promoters or synthetic polynucleotide segments. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents.

"Tissue-specific promoter" and "tissue-preferred promoter" as used interchangeably herein refer to a promoter that is expressed predominantly but not necessarily exclusively in one tissue or organ, but that may also be expressed in one specific cell. A "developmentally regulated promoter" refers to a promoter whose function is determined by developmental events. A "constitutive promoter" refers to a promoter that causes a gene to be expressed in most cell types at most times. An "inducible promoter" selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include promoters regulated by light, heat, stress, flooding or drought, pathogens, phytohormones, wounding, or chemicals such as ethanol, jasmonate, salicylic acid, or safeners.

"Recombinant" as used herein refers to an artificial combination of two otherwise separated segments of sequence—such as by chemical synthesis or by the manipulation of isolated segments of polynucleotides by genetic engineering techniques. The term also includes reference to a cell or vector, that has been modified by the introduction of a heterologous polynucleotide or a cell derived from a cell so modified, but does not encompass the alteration of the cell or vector by naturally occurring events (for example, spontaneous mutation, natural transformation or transduction or transposition) such as those occurring without deliberate human intervention.

"Recombinant construct" refers to a combination of polynucleotides that are not normally found together in nature. Accordingly, a recombinant construct may comprise regulatory sequences and coding sequences that are derived from different sources, or regulatory sequences and coding sequences derived from the same source, but arranged in a manner different than that normally found in nature. The recombinant construct can be a recombinant DNA construct.

"Regulatory sequences" and "regulatory elements" as used interchangeably herein refer to polynucleotide sequences located upstream (5' non-coding sequences), within, or downstream (3' non-coding sequences) of a coding sequence, and which influence the transcription, RNA processing or stability, or translation of the associated coding sequence. Regulatory sequences include promoters, translation leader sequences, introns, and polyadenylation recognition sequences. The terms "regulatory sequence" and "regulatory element" are used interchangeably herein.

"Site-specific nuclease" refers to an enzyme capable of specifically recognizing and cleaving DNA sequences. The site-specific nuclease may be engineered. Examples of engineered site-specific nucleases include zinc finger nucleases (ZFNs), TAL effector nucleases (TALENs), CRISPR/Cas9-based systems, and meganucleases.

The term "tobacco" is used in a collective sense to refer to tobacco crops (for example, a plurality of tobacco plants grown in the field and not hydroponically grown tobacco), tobacco plants and parts thereof, including but not limited to, roots, stems, leaves, flowers, and seeds prepared and/or obtained, as described herein. It is understood that "tobacco" refers to *Nicotiana tabacum* plants and products thereof.

The term "tobacco products" refers to consumer tobacco products, including but not limited to, smoking materials (for example, cigarettes, cigars, and pipe tobacco), snuff, chewing tobacco, gum, and lozenges, as well as components, materials and ingredients for manufacture of consumer tobacco products. Suitably, these tobacco products are manufactured from tobacco leaves and stems harvested from tobacco and cut, dried, cured, and/or fermented according to conventional techniques in tobacco preparation.

"Transcription terminator", "termination sequences", or "terminator" refers to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Transgenic" refers to any cell, cell line, callus, tissue, plant part or plant, the genome of which has been altered by the presence of a heterologous polynucleotide, such as a recombinant construct, including those initial transgenic events as well as those created by sexual crosses or asexual propagation from the initial transgenic event. The term does not encompass the alteration of the genome (chromosomal or extra-chromosomal) by conventional plant breeding methods or by naturally occurring events—such as random cross-fertilization, non-recombinant viral infection, non-recombinant bacterial transformation, non-recombinant transposition, or spontaneous mutation.

"Transgenic plant" refers to a plant which comprises within its genome one or more heterologous polynucleotides, that is, a plant that contains recombinant genetic material not normally found therein and which has been introduced into the plant in question (or into progenitors of the plant) by human manipulation. For example, the heterologous polynucleotide can be stably integrated within the genome such that the polynucleotide is passed on to successive generations. The heterologous polynucleotide can be integrated into the genome alone or as part of a recombinant construct. The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems and the like. Each heterologous polynucleotide may confer a different trait to the transgenic plant.

"Transcription activator-like effector" or "TALE" refers to a polypeptide structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence. A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors, methyltransferases, integrases, nucleases, and recombinases.

"Transcription activator-like effector nucleases" or "TALENs" as used interchangeably herein refers to engineered fusion polypeptides of the catalytic domain of a nuclease, such as endonuclease FokI, and a designed TALE DNA-binding domain that may be targeted to a custom DNA sequence.

A "TALEN monomer" refers to an engineered fusion polypeptide with a catalytic nuclease domain and a designed TALE DNA-binding domain. Two TALEN monomers may be designed to target and cleave a TALEN target region.

"Transgene" refers to a gene or genetic material containing a gene sequence that has been isolated from one organism and is introduced into a different organism. This non-native segment of DNA may retain the ability to produce RNA or polypeptide in the transgenic organism, or it may alter the normal function of the transgenic organism's genetic code. The introduction of a transgene has the potential to change the phenotype of an organism.

"Variant" with respect to a polynucleotide means: (i) a portion or fragment of a polynucleotide; (ii) the complement of a polynucleotide or portion thereof; (iii) a polynucleotide that is substantially identical to a polynucleotide of interest or the complement thereof; or (iv) a polynucleotide that hybridizes under stringent conditions to the polynucleotide of interest, complement thereof, or a polynucleotide substantially identical thereto.

"Variant" with respect to a peptide or polypeptide means a peptide or polypeptide that differs in sequence by the insertion, deletion, or conservative substitution of amino acids, but retain at least one biological function or activity. Variant may also mean a polypeptide that retains at least one biological function or activity. A conservative substitution of an amino acid, that is, replacing an amino acid with a different amino acid of similar properties (for example, hydrophilicity, degree and distribution of charged regions) is recognized in the art as typically involving a minor change.

The term "variety" refers to a population of plants that share constant characteristics which separate them from other plants of the same species. While possessing one or more distinctive traits, a variety is further characterized by a very small overall variation between individuals within that variety. A variety is often sold commercially.

"Vector" refers to a polynucleotide vehicle that comprises a combination of polynucleotide components for enabling the transport of polynucleotides, polynucleotide constructs and polynucleotide conjugates and the like. A vector may be a viral vector, bacteriophage, bacterial artificial chromosome or yeast artificial chromosome. A vector may be a DNA or RNA vector. Suitable vectors include episomes capable of extra-chromosomal replication such as circular, double-stranded nucleotide plasmids; linearized double-stranded nucleotide plasmids; and other vectors of any origin. An "expression vector" as used herein is a polynucleotide vehicle that comprises a combination of polynucleotide components for enabling the expression of polynucleotide(s), polynucleotide constructs and polynucleotide conjugates and the like. Suitable expression vectors include episomes capable of extra-chromosomal replication such as circular, double-stranded nucleotide plasmids; linearized double-stranded nucleotide plasmids; and other functionally equivalent expression vectors of any origin. An expression vector comprises at least a promoter positioned upstream and operably-linked to a polynucleotide, polynucleotide constructs or polynucleotide conjugate, as defined below.

"Zinc finger" refers to a polypeptide structure that recognizes and binds to DNA sequences. The zinc finger domain is the most common DNA-binding motif in the human proteome. A single zinc finger contains approximately 30 amino acids and the domain typically functions by binding 3 consecutive base pairs of DNA via interactions of a single amino acid side chain per base pair.

"Zinc finger nuclease" or "ZFN" refers to a chimeric polypeptide molecule comprising at least one zinc finger DNA binding domain effectively linked to at least one nuclease or part of a nuclease capable of cleaving DNA when fully assembled.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and polypeptide and polynucleotide chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Polynucleotides

In one embodiment, there is provided an isolated polynucleotide comprising, consisting or consisting essentially of a sequence having at least 60% sequence identity to any of the sequences described herein, including any of polynucleotides shown in the sequence listing. Suitably, the isolated polynucleotide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto. Suitably, the polynucleotide(s) described herein encode an active AAT polypeptide that has at least about 50%, 60%, 70%, 80%, 90% 95%, 96%, 97%, 98%, 99%, 100% or more of the function or activity of the polypeptide(s) shown in the sequence listing.

In another embodiment, there is provided an isolated polynucleotide comprising, consisting or consisting essentially of a polynucleotide having at least 80% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15.

In another embodiment, there is provided an isolated polynucleotide comprising, consisting or consisting essentially of a sequence having at least 80% sequence identity to SEQ ID NO: 5 or SEQ ID NO: 7.

In certain embodiments, there is provided an isolated polynucleotide comprising, consisting or consisting essentially of a sequence having at least 80% sequence identity to SEQ ID NO: 1 or SEQ ID NO: 3.

Suitably, the isolated polynucleotide(s) comprises, consists or consist essentially of a sequence having at least about 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15.

Suitably, the isolated polynucleotide(s) comprises, consists or consist essentially of a sequence having at least about 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 5 or SEQ ID NO: 7.

Suitably, the isolated polynucleotide(s) comprises, consists or consist essentially of a sequence having at least about 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 1 or SEQ ID NO: 3.

In another embodiment, there is provided polynucleotides comprising, consisting or consisting essentially of polynucleotides with substantial homology (that is, sequence similarity) or substantial identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15.

In another embodiment, there is provided polynucleotides comprising, consisting or consisting essentially of polynucleotides with substantial homology (that is, sequence similarity) or substantial identity to SEQ ID NO: 5 or SEQ ID NO: 7.

In another embodiment, there is provided polynucleotides comprising, consisting or consisting essentially of polynucleotides with substantial homology (that is, sequence similarity) or substantial identity to SEQ ID NO: 1 or SEQ ID NO: 3.

In another embodiment, there is provided fragments of SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15 with substantial homology (that is, sequence similarity) or substantial identity thereto that have at least about 80%, 85%, 86% 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15.

In another embodiment, there is provided fragments of SEQ ID NO: 5 or SEQ ID NO: 7 with substantial homology (that is, sequence similarity) or substantial identity thereto that have at least about 80%, 85%, 86% 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 5 or SEQ ID NO: 7.

In another embodiment, there is provided fragments of SEQ ID NO: 1 or SEQ ID NO: 3 with substantial homology (that is, sequence similarity) or substantial identity thereto that have at least about 80%, 85%, 86% 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 1 or SEQ ID NO: 3.

In another embodiment, there is provided polynucleotides comprising a sufficient or substantial degree of identity or similarity to SEQ ID NO: 5 or SEQ ID NO: 7 that encode a polypeptide that functions as an AAT.

In another embodiment, there is provided polynucleotides comprising a sufficient or substantial degree of identity or similarity to SEQ ID NO: 1 or SEQ ID NO: 3 that encode a polypeptide that functions as an AAT.

In another embodiment, there is provided polynucleotides comprising a sufficient or substantial degree of identity or similarity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15 that encode a polypeptide that functions as an AAT.

In another embodiment, there is provided polynucleotides comprising a sufficient or substantial degree of identity or similarity to SEQ ID NO: 5 or SEQ ID NO: 7 that encode a polypeptide that functions as an AAT.

In another embodiment, there is provided polynucleotides comprising a sufficient or substantial degree of identity or similarity to SEQ ID NO: 1 or SEQ ID NO: 3 that encode a polypeptide that functions as an AAT.

In another embodiment, there is provided a polymer of polynucleotides which comprises, consists or consists essentially of a polynucleotide designated herein as SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15.

In another embodiment, there is provided a polymer of polynucleotides which comprises, consists or consists essentially of a polynucleotide designated herein as SEQ ID NO: 5 or SEQ ID NO: 7.

In another embodiment, there is provided a polymer of polynucleotides which comprises, consists or consists essentially of a polynucleotide designated herein as SEQ ID NO: 1 or SEQ ID NO: 3.

Suitably, the polynucleotides described herein encode an AAT polypeptide.

As described herein, NtAAT2-S(SEQ ID NO: 1) and NtAAT2-T (SEQ ID NO: 3) are the most expressed genes after 48 hours curing as compared to green tobacco. The level of expression can be 2, 3, 4, 5, 6, 7, 8, 9, 10 or 11 times greater than green tobacco. The use of NtAAT2-S (SEQ ID NO: 1) and NtAAT2-T (SEQ ID NO: 3) is preferred in certain embodiments of the present disclosure. A polynucleotide can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, they include their corresponding RNA sequences, and their complementary (for example, completely complementary) DNA or RNA sequences, including the reverse complements thereof.

A polynucleotide will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

Other analogues include peptide polynucleotides which are peptide polynucleotide analogues. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide polynucleotides have larger changes in the melting temperature for mismatched versus perfectly matched base pairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide polynucleotides may not be degraded or degraded to a lesser extent by cellular enzymes, and thus may be more stable.

Among the uses of the disclosed polynucleotides, and fragments thereof, is the use of fragments as probes in hybridisation assays or primers for use in amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting a polynucleotide comprising the use of the probes or primers or both. Exemplary primers are described herein.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the polypeptide sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries include cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under decreased stringency conditions, typically moderately stringent conditions, and commonly highly stringent conditions to the polynucleotide(s), as described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y. and can be readily determined by those having ordinary skill in the art based on, for example, the length or base composition of the polynucleotide.

One way of achieving moderately and high stringent conditions are defined herein. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N.Y). When hybridizing a polynucleotide to a polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2 (number of A+T bases)+4 (number of G+C bases). For hybrids above 18 base pairs in length, melting temperature (° C.)=81.5+16.6 (log 10 [Na+])+0.41 (% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a first sequence is positioned in the 5'-to-3' direction, and if a second sequence is positioned in the 5'-to-3' direction within the same polynucleotide molecule/strand, then the first sequence and the second sequence are orientated in the same direction, or have the same orientation. Typically, a promoter sequence and a gene of interest under the regulation of the given promoter are positioned in the same orientation. However, with respect to the first sequence positioned in the 5'-to-3' direction, if a second sequence is positioned in the 3'-to-5' direction within the same polynucleotide molecule/strand, then the first sequence and the second sequence are orientated in anti-sense direction, or have anti-sense orientation. Two sequences having anti-sense orientations with respect to each other can be alternatively described as having the same orientation, if the first sequence (5'-to-3' direction) and the reverse complementary sequence of the first sequence (first sequence positioned in the 5'-to-3') are positioned within the same polynucleotide molecule/strand. The sequences set forth herein are shown in the 5'-to-3' direction.

At least one modification (for example, mutation) can be included in one or more of NtAAT1-S (SEQ ID NO: 5), NtAAT1-T (SEQ ID NO: 7), NtAAT2-S(SEQ ID NO: 1), NtAAT2-T (SEQ ID NO: 3), NtAAT3-S(SEQ ID NO: 9), NtAAT3-T (SEQ ID NO: 11), NtAAT4-S(SEQ ID NO: 13) and NtAAT4-T (SEQ ID NO: 15).

In certain embodiments, at least one modification (for example, mutation) can be included in one or more of NtAAT1-S(SEQ ID NO: 5) and NtAAT1-T (SEQ ID NO: 7).

In certain embodiments, at least one modification (for example, mutation) can be included in one or more of NtAAT2-S(SEQ ID NO: 1) and NtAAT2-T (SEQ ID NO: 3).

In certain embodiments, at least one modification (for example, mutation) can be included in one or more of NtAAT1-S(SEQ ID NO: 5), NtAAT1-T (SEQ ID NO: 7), NtAAT2-S(SEQ ID NO: 1) and NtAAT2-T (SEQ ID NO: 3).

In certain embodiments, at least one modification (for example, mutation) can be included in one or more of NtAAT1-S(SEQ ID NO: 5), NtAAT1-T (SEQ ID NO: 7), NtAAT2-S(SEQ ID NO: 1) and NtAAT2-T (SEQ ID NO: 3) whereas one or more of NtAAT3-S(SEQ ID NO: 9), NtAAT3-T (SEQ ID NO: 11), NtAAT4-S(SEQ ID NO: 13) and NtAAT4-T (SEQ ID NO: 15) include no modification(s) (for example, mutation(s)).

In certain embodiments, at least one modification (for example, mutation) can be included in one or more of NtAAT1-S(SEQ ID NO: 5), NtAAT1-T (SEQ ID NO: 7), NtAAT2-S(SEQ ID NO: 1) and NtAAT2-T (SEQ ID NO: 3) whereas NtAAT3-S(SEQ ID NO: 9), NtAAT3-T (SEQ ID NO: 11), NtAAT4-S(SEQ ID NO: 13) and NtAAT4-T (SEQ ID NO: 15)) include no modification(s) (for example, mutation(s)).

Polypeptides

In another aspect, there is provided an isolated polypeptide comprising, consisting or consisting essentially of a polypeptide having at least 60% sequence identity to any of the polypeptides described herein, including any of the polypeptides shown in the sequence listing. Suitably, the isolated polypeptide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto.

In one embodiment, there is provided a polypeptide encoded by any of the polynucleotides described herein, including a polynucleotide having at least 80% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15.

In another embodiment, there is provided an isolated polypeptide comprising, consisting or consisting essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 6, SEQ ID No: 8, SEQ ID NO: 2, SEQ ID No: 4, SEQ ID NO: 10 or SEQ ID No: 12.

In another embodiment, there is provided an isolated polypeptide comprising, consisting or consisting essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2 or SEQ ID No: 4.

In another embodiment, there is provided an isolated polypeptide comprising, consisting or consisting essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 6 or SEQ ID No: 8.

In another embodiment, there is provided an isolated polypeptide comprising, consisting or consisting essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 6 or SEQ ID No: 8; at least 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2 or SEQ ID No: 4; or at least 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 14 or SEQ ID NO: 16.

The polypeptide can include sequences comprising a sufficient or substantial degree of identity or similarity to SEQ ID NO: SEQ ID NO: 6, SEQ ID No: 8, SEQ ID NO: 2, SEQ ID No: 4, SEQ ID NO: 10 or SEQ ID No: 12 to function as an AAT. The polypeptide can include sequences comprising a sufficient or substantial degree of identity or similarity to SEQ ID NO: 6 or SEQ ID No: 8 to function as an AAT. The polypeptide can include sequences comprising a sufficient or substantial degree of identity or similarity to SEQ ID NO: 2 or SEQ ID No: 4 to function as an AAT. The fragments of the polypeptide(s) typically retain some or all of the AAT function or activity of the full length sequence.

As described herein, NtAAT2-S(SEQ ID NO: 1) and NtAAT2-T (SEQ ID NO: 3) are the most expressed genes after 48 hours curing as compared to green tobacco. The level of expression can be 2, 3, 4, 5, 6, 7, 8, 9, 10 or 11 times greater than green tobacco. The use of NtAAT2-S (SEQ ID NO: 1) and NtAAT2-T (SEQ ID NO: 3) is preferred in certain embodiments of the present disclosure. As discussed herein, the polypeptides also include mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still have some or all of their function or activity. Suitably, this function or activity is modulated.

A deletion refers to removal of one or more amino acids from a polypeptide. An insertion refers to one or more amino acid residues being introduced into a predetermined site in a polypeptide. Insertions may comprise intra-sequence insertions of single or multiple amino acids. A substitution refers to the replacement of amino acids of the polypeptide with other amino acids having similar properties (such as similar hydrophobicity, hydrophilicity, antigenicity, propensity to form or break a-helical structures or β-sheet structures). Amino acid substitutions are typically of single residues, but may be clustered depending upon functional constraints placed upon the polypeptide and may range from about 1 to about 10 amino acids. The amino acid substitutions are preferably conservative amino acid substitutions as described below. Amino acid substitutions, deletions and/or insertions can be made using peptide synthetic techniques—such as solid phase peptide synthesis or by recombinant DNA manipulation. Methods for the manipulation of DNA sequences to produce substitution, insertion or deletion variants of a polypeptide are well known in the art. The variant may have alterations which produce a silent change and result in a functionally equivalent polypeptide. Deliberate amino acid substitutions may be made on the basis of similarity in polarity, charge, solubility, hydrophobicity, hydrophilicity and the amphipathic nature of the residues as long as the secondary binding of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, *Glycine*, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| | | |
|---|---|---|
| ALIPHATIC | Non-polar | Gly Ala Pro |
| | | Ile Leu Val |
| | Polar-uncharged | Cys Ser Thr Met |
| | | Asn Gly |
| | Polar-charged | Asp Glu |
| | | Lys Arg |
| AROMATIC | | His Phe Trp Tyr |

The polypeptide may be a mature polypeptide or an immature polypeptide or a polypeptide derived from an immature polypeptide. Polypeptides may be in linear form or cyclized using known methods. Polypeptides typically comprise at least 10, at least 20, at least 30, or at least 40 contiguous amino acids.

At least one modification (for example, mutation) can be included in one or more of NtAAT1-S (SEQ ID NO: 6), NtAAT1-T (SEQ ID NO: 8), NtAAT2-S(SEQ ID NO: 2), NtAAT2-T (SEQ ID NO: 4), NtAAT3-S(SEQ ID NO: 10), NtAAT3-T (SEQ ID NO: 12), NtAAT4-S(SEQ ID NO: 14) and NtAAT4-T (SEQ ID NO: 16).

In certain embodiments, at least one modification (for example, mutation) can be included in one or more of NtAAT1-S(SEQ ID NO: 6), NtAAT1-T (SEQ ID NO: 8), NtAAT2-S(SEQ ID NO: 2) and NtAAT2-T (SEQ ID NO: 4), In certain embodiments, at least one modification (for example, mutation) can be included in one or more of NtAAT1-S(SEQ ID NO: 6) and NtAAT1-T T (SEQ ID NO: 8), In certain embodiments, at least one modification (for example, mutation) can be included in one or more of NtAAT2-S(SEQ ID NO: 2) and NtAAT2-T (SEQ ID NO: 4), In certain embodiments, at least one modification (for example, mutation) can be included in one or more of NtAAT1-S(SEQ ID NO: 6), NtAAT1-T (SEQ ID NO: 8), NtAAT2-S(SEQ ID NO: 2) and NtAAT2-T (SEQ ID NO: 4) whereas one or more of NtAAT3-S(SEQ ID NO: 10), NtAAT3-T (SEQ ID NO: 12), NtAAT4-S(SEQ ID NO: 14) and NtAAT4-T (SEQ ID NO: 16) include no modifications (for example, mutation(s).

In certain embodiments, at least one modification (for example, mutation) can be included in one or more of NtAAT1-S(SEQ ID NO: 6), NtAAT1-T (SEQ ID NO: 8), NtAAT2-S(SEQ ID NO: 2) and NtAAT2-T (SEQ ID NO: 4) whereas NtAAT3-S(SEQ ID NO: 10), NtAAT3-T (SEQ ID NO: 12), NtAAT4-S(SEQ ID NO: 14) and NtAAT4-T (SEQ ID NO: 16) include no modifications (for example, mutation (s).

Modifying Plants a. Transformation

Recombinant constructs can be used to transform plants or plant cells in order to modulate polypeptide expression, function or activity. A recombinant polynucleotide construct can comprise a polynucleotide encoding one or more polynucleotides as described herein, operably linked to a regulatory region suitable for expressing the polypeptide. Thus, a polynucleotide can comprise a coding sequence that encodes the polypeptide as described herein. Plants or plant cells in which polypeptide expression, function or activity are modulated can include mutant, non-naturally occurring, transgenic, man-made or genetically engineered plants or plant cells. Suitably, the transgenic plant or plant cell comprises a genome that has been altered by the stable integration of recombinant DNA. Recombinant DNA includes DNA which has been genetically engineered and constructed outside of a cell and includes DNA containing naturally occurring DNA or cDNA or synthetic DNA. A transgenic plant can include a plant regenerated from an originally-transformed plant cell and progeny transgenic plants from later generations or crosses of a transformed plant. Suitably, the transgenic modification alters the expression or function or activity of the polynucleotide or the polypeptide described herein as compared to a control plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available.

The vectors can include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent polypeptide, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell can be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions.

A number of methods are available in the art for transforming a plant cell including biolistics, gene gun techniques, *Agrobacterium*-mediated transformation, viral vector-mediated transformation, freeze-thaw method, microparticle bombardment, direct DNA uptake, sonication, microinjection, plant virus-mediated transfer, and electroporation. The *Agrobacterium* system for integration of foreign DNA into plant chromosomes has been extensively studied, modified, and exploited for plant genetic engineering. Naked recombinant DNA molecules comprising DNA sequences corresponding to the subject purified polypeptide operably linked, in the sense or antisense orientation, to regulatory sequences are joined to appropriate T-DNA sequences by conventional methods. These are introduced into protoplasts by polyethylene glycol techniques or by electroporation techniques, both of which are standard. Alternatively, such vectors comprising recombinant DNA molecules encoding the subject purified polypeptide are introduced into live *Agrobacterium* cells, which then transfer the DNA into the plant cells.

Transformation by naked DNA without accompanying T-DNA vector sequences can be accomplished via fusion of protoplasts with DNA-containing liposomes or via electroporation. Naked DNA unaccompanied by T-DNA vector sequences can also be used to transform cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Suitable promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease, the promoter of 82E4 and the promoter of SAG genes. Suitable anther-specific promoters can be used. Suitable root-preferred promoters known to persons skilled in the art may be selected. Suitable seed-preferred promoters include both seed-specific promoters (those promoters active during seed development such as promoters of seed storage polypeptides) and seed-germinating promoters (those promoters active during seed germination). Such seed-preferred promoters include Cim1 (cytokinin-induced message); cZ19B1 (maize 19 kDa zein); milps (myo-inositol-1-phosphate synthase); mZE40-2, also known as Zm-40; nucic; and celA (cellulose synthase). Gama-zein is an endosperm-specific promoter. Glob-1 is an embryo-specific promoter. For dicots, seed-specific promoters include bean beta-phaseolin, napin, β-conglycinin, soybean lectin, cruciferin, and the like. For monocots, seed-specific promoters include a maize 15 kDa zein promoter, a 22 kDa zein promoter, a 27 kDa zein promoter, a g-zein promoter, a 27 kDa gamma-zein promoter (such as gzw64A promoter, see Genbank Accession number S78780), a waxy promoter, a shrunken 1 promoter, a shrunken 2 promoter, a globulin 1 promoter (see Genbank Accession number L22344), an Itp2 promoter, cim1 promoter, maize end1 and end2 promoters, nuc1 promoter, Zm40 promoter, eep1 and eep2; led, thioredoxin H promoter; mlip15 promoter, PCNA2 promoter; and the shrunken-2 promoter. Examples of inducible promoters include promoters responsive to pathogen attack, anaerobic conditions, elevated temperature, light, drought, cold temperature, or high salt concentration. Pathogen-inducible promoters include those from pathogenesis-related polypeptides (PR polypeptides), which are induced following infection by a pathogen (for example, PR polypeptides, SAR polypeptides, beta-1,3-glucanase, chitinase).

In addition to plant promoters, other suitable promoters may be derived from bacterial origin for example, the octopine synthase promoter, the nopaline synthase promoter and other promoters derived from Ti plasmids, or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

Suitable methods of introducing polynucleotides into plant cells and subsequent insertion into the plant genome include microinjection (Crossway et al., Biotechniques 4:320-334 (1986)), electroporation (Riggs et al., Proc. Natl. Acad. Sci. USA 83:5602-5606 (1986)), *Agrobacterium*-mediated transformation (U.S. Pat. Nos. 5,981,840 and 5,563,055), direct gene transfer (Paszkowski et al., EMBO J. 3:2717-2722 (1984)), and ballistic particle acceleration (see, for example, U.S. Pat. Nos. 4,945,050; 5,879,918; 5,886,244; 5,932,782; Tomes et al., in Plant Cell, Tissue, and Organ Culture: Fundamental Methods, ed. Gamborg and Phillips (Springer-Verlag, Berlin) (1995); and McCabe et al., Biotechnology 6:923-926 (1988)).

b. Mutation

A plant or plant cell comprising a mutation in one or more of the polynucleotides or polypeptides described herein is disclosed, wherein said mutation results in modulated AAT function or activity. Aside from the mutations described, the mutant plants or plant cells can have one or more further mutations either in the same polynucleotides or polypeptides as described herein or in one or more other polynucleotides or polypeptides within the genome.

There is also provided a method for modulating the level of an AAT polypeptide as described herein in a (cured) plant or in (cured) plant material said method comprising introducing into the genome of said plant one or more mutations that modulate expression of at least one gene, wherein said at least one gene is selected from the sequences according to the present disclosure.

There is also provided a method for identifying a plant with modulated levels of AAT, said method comprising screening a polynucleotide sample from a plant of interest for the presence of one or more mutations in the sequences according to the present disclosure, and optionally correlating the identified mutation(s) with mutation(s) that are known to modulate levels of one or AAT.

There is also disclosed a plant or plant cell that is heterozygous or homozygous for one or more mutations in a gene according to the present disclosure, wherein said mutation results in modulated expression of the gene or function or activity of the polypeptide encoded thereby.

A number of approaches can be used to combine mutations in one plant including sexual crossing. A plant having one or more favourable heterozygous or homozygous mutations in a gene according to the present disclosure that modulates expression of the gene or the function or activity of the polypeptide encoded thereby can be crossed with a plant having one or more favourable heterozygous or homozygous mutations in one or more other genes that modulate expression thereof or the function or activity of the polypeptide encoded thereby. In one embodiment, crosses are made in order to introduce one or more favourable heterozygous or homozygous mutations within gene according to the present disclosure within the same plant.

The function or activity of one or more polypeptides of the present disclosure in a plant is increased or decreased if the function or activity is lower or higher than the function or activity of the same polypeptide(s) in a plant that has not been modified to inhibit the function or activity of that polypeptide and which has been cultured, harvested and cured using the same protocols.

In some embodiments, the mutation(s) is introduced into a plant or plant cell using a mutagenesis approach, and the introduced mutation is identified or selected using methods known to those of skill in the art—such as Southern blot analysis, DNA sequencing, PCR analysis, or phenotypic analysis. Mutations that impact gene expression or that interfere with the function of the encoded polypeptide can be determined using methods that are well known in the art. Insertional mutations in gene exons usually result in null-mutants. Mutations in conserved residues can be particularly effective in inhibiting the metabolic function of the encoded polypeptide. It will be appreciated, for example, that a mutation in one or more of the highly conserved regions would likely alter polypeptide function, while a mutation outside of those highly conserved regions would likely have little to no effect on polypeptide function. In addition, a mutation in a single nucleotide can create a stop codon, which would result in a truncated polypeptide and, depending on the extent of truncation, loss of function.

Methods for obtaining mutant polynucleotides and polypeptides are also disclosed. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Fragments of polynucleotides and polypeptides are also disclosed. Fragments of a polynucleotide may encode polypeptide fragments that retain the biological function of the native polypeptide and hence are involved in the metabolite transport network in a plant. Alternatively, fragments of a polynucleotide that are useful as hybridization probes or PCR primers generally do not encode fragment polypeptides retaining biological function. Furthermore, fragments of the disclosed polynucleotides include those that can be assembled within recombinant constructs as discussed herein. Fragments of a polynucleotide may range from at least about 25 nucleotides, about 50 nucleotides, about 75 nucleotides, about 100 nucleotides about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides or about 1400 nucleotides and up to the full-length polynucleotide encoding the polypeptides described herein. Fragments of a polypeptide may range from at least about 25 amino acids, about 50 amino acids, about 75 amino acids, about 100 amino acids about 150 amino acids, about 200 amino acids, about 250 amino acids, about 300 amino acids, about 400 amino acids, about 500 amino acids, and up to the full-length polypeptide described herein. Mutant polypeptide variants can be used to create mutant, non-naturally occurring or transgenic plants (for example, mutant, non-naturally occurring, transgenic, man-made or genetically engineered plants) or plant cells comprising one or more mutant polypeptide variants. Suitably, mutant polypeptide variants retain the function of the unmutated polypeptide. The function of the mutant polypeptide variant may be higher, lower or about the same as the unmutated polypeptide.

Mutations in the polynucleotides and polypeptides described herein can include man-made mutations or synthetic mutations or genetically engineered mutations. Mutations in the polynucleotides and polypeptides described herein can be mutations that are obtained or obtainable via a process which includes an in vitro or an in vivo manipulation step. Mutations in the polynucleotides and polypeptides described herein can be mutations that are obtained or obtainable via a process which includes intervention by man.

Methods that introduce a mutation randomly in a polynucleotide can include chemical mutagenesis and radiation mutagenesis. Chemical mutagenesis involves the use of exogenously added chemicals—such as mutagenic, teratogenic, or carcinogenic organic compounds—to induce mutations. Mutagens that create primarily point mutations and short deletions, insertions, missense mutations, simple sequence repeats, transversions, and/or transitions, including chemical mutagens or radiation, may be used to create the mutations. Mutagens include ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. The dosage of the mutagenic chemical or radiation is determined experimentally for each type of plant tissue such that a mutation frequency is obtained that is below a threshold level characterized by lethality or reproductive sterility. Any method of plant polynucleotide preparation known to those of skill in the art may be used to prepare the plant polynucleotide for mutation screening.

The mutation process may include one or more plant crossing steps.

After mutation, screening can be performed to identify mutations that create premature stop codons or otherwise non-functional genes. After mutation, screening can be performed to identify mutations that create functional genes that are capable of being expressed at increased or decreased levels. Screening of mutants can be carried out by sequencing, or by the use of one or more probes or primers specific to the gene or polypeptide. Specific mutations in polynucleotides can also be created that can result in modulated gene expression, modulated stability of mRNA, or modulated stability of polypeptide. Such plants are referred to herein as "non-naturally occurring" or "mutant" plants. Typically, the mutant or non-naturally occurring plants will include at least a portion of foreign or synthetic or man-made nucleotide (for example, DNA or RNA) that was not present in the plant before it was manipulated. The foreign nucleotide may be a single nucleotide, two or more nucleotides, two or more contiguous nucleotides or two or more non-contiguous nucleotides—such as at least 10, 20, 30, 40, 50, 100, 200, 300, 400, 500, 600, 700, 800, 900, 1000, 1100, 1200, 1300, 1400 or 1500 or more contiguous or non-contiguous nucleotides.

c. Transgenics and Editing

Other than mutagenesis, compositions that can modulate the expression or function or activity of one or more of the polynucleotides or polypeptides described herein include sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more polypeptides; sequence-specific polynucleotides that can interfere with the enzymatic function of one or more polypeptides or the binding function of one or more polypeptides with respect to substrates or regulatory polypeptides; antibodies that exhibit specificity for one or more polypeptides; small molecule compounds that can interfere with the stability of one or more polypeptides or the enzymatic function of one or more polypeptides or the binding function of one or more polypeptides; zinc finger polypeptides that bind one or more polynucleotides; and meganucleases that have function towards one or more polynucleotides. Gene editing technologies, genetic editing technologies and genome editing technologies are well known in the art.

d. Zinc Finger Nucleases

Zinc finger polypeptides can be used to modulate the expression or function or activity of one or more of the polynucleotides described herein. In various embodiments, a genomic DNA sequence comprising a part of or all of the coding sequence of the polynucleotide is modified by zinc finger nuclease-mediated mutagenesis. The genomic DNA sequence is searched for a unique site for zinc finger polypeptide binding. Alternatively, the genomic DNA sequence is searched for two unique sites for zinc finger polypeptide binding wherein both sites are on opposite strands and close together, for example, 1, 2, 3, 4, 5, 6 or more base pairs apart. Accordingly, zinc finger polypeptides that bind to polynucleotides are provided.

A zinc finger polypeptide may be engineered to recognize a selected target site in a gene. A zinc finger polypeptide can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-base pair sequence within the polynucleotide target and that does not occur in the cell or organism comprising the polynucleotide which is to be modified. Methods for the design of zinc finger polypeptide which binds specific polynucleotides which are unique to a target gene are known in the art.

In other embodiments, a zinc finger polypeptide may be selected to bind to a regulatory sequence of a polynucleotide. More specifically, the regulatory sequence may comprise a transcription initiation site, a start codon, a region of an exon, a boundary of an exon-intron, a terminator, or a stop codon. Accordingly, the disclosure provides a mutant, non-naturally occurring or transgenic plant or plant cells, produced by zinc finger nuclease-mediated mutagenesis in the vicinity of or within one or more polynucleotides described herein, and methods for making such a plant or plant cell by zinc finger nuclease-mediated mutagenesis. Methods for delivering zinc finger polypeptide and zinc finger nuclease to a plant are similar to those described below for delivery of meganuclease.

e. Meganucleases

In another aspect, methods for producing mutant, non-naturally occurring or transgenic or otherwise genetically-modified plants using meganucleases, such as I-CreI, are described. Naturally occurring meganucleases as well as recombinant meganucleases can be used to specifically cause a double-stranded break at a single site or at relatively few sites in the genomic DNA of a plant to allow for the disruption of one or more polynucleotides described herein. The meganuclease may be an engineered meganuclease with altered DNA-recognition properties. Meganuclease polypeptides can be delivered into plant cells by a variety of different mechanisms known in the art.

The disclosure encompass the use of meganucleases to inactivate a polynucleotide(s) described herein (or any combination thereof as described herein) in a plant cell or plant. Particularly, the disclosure provides a method for inactivating a polynucleotide in a plant using a meganuclease comprising: a) providing a plant cell comprising a polynucleotide as described herein; (b) introducing a meganuclease or a construct encoding a meganuclease into said plant cell; and (c) allowing the meganuclease to substantially inactivate the polynucleotide(s)

Meganucleases can be used to cleave meganuclease recognition sites within the coding regions of a polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques.

Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the function of the engineered meganuclease to cleave and mutate the meganuclease recognition site.

f. TALENs

One method of gene editing involves the use of transcription activator-like effector nucleases (TALENs) which induce double-strand breaks which cells can respond to with repair mechanisms. NHEJ reconnects DNA from either side of a double-strand break where there is very little or no sequence overlap for annealing. This repair mechanism induces errors in the genome via insertion or deletion, or chromosomal rearrangement. Any such errors may render the gene products coded at that location non-functional. For certain applications, it may be desirable to precisely remove the polynucleotide from the genome of the plant. Such applications are possible using a pair of engineered meganucleases, each of which cleaves a meganuclease recognition site on either side of the intended deletion. TALENs that are able to recognize and bind to a gene and introduce a double-strand break into the genome can also be used. Thus, in another aspect, methods for producing mutant, non-naturally occurring or transgenic or otherwise genetically-modified plants as described herein using TAL Effector Nucleases are contemplated.

g. CRISPR/Cas

Another method of gene editing involves the use of the bacterial CRISPR/Cas system. Bacteria and archaea exhibit chromosomal elements called clustered regularly interspaced short palindromic repeats (CRISPR) that are part of an adaptive immune system that protects against invading viral and plasmid DNA. In Type II CRISPR systems, CRISPR RNAs (crRNAs) function with trans-activating crRNA (tracrRNA) and CRISPR-associated (Cas) polypeptides to introduce double-stranded breaks in target DNA. Target cleavage by Cas9 requires base-pairing between the crRNA and tracrRNA as well as base pairing between the crRNA and the target DNA. Target recognition is facilitated by the presence of a short motif called a protospacer-adjacent motif (PAM) that conforms to the sequence NGG. This system can be harnessed for genome editing. Cas9 is normally programmed by a dual RNA consisting of the crRNA and tracrRNA. However, the core components of these RNAs can be combined into a single hybrid ‘guide RNA’ for Cas9 targeting. The use of a noncoding RNA guide to target DNA for site-specific cleavage promises to be significantly more straightforward than existing technologies—such as TALENs. Using the CRISPR/Cas strategy, retargeting the nuclease complex only requires introduction of a new RNA sequence and there is no need to reengineer the specificity of polypeptide transcription factors. CRISPR/Cas technology was implemented in plants in the method of international application WO 2015/189693, which discloses a viral-mediated genome editing platform that is broadly applicable across plant species. The RNA2 genome of the tobacco rattle virus (TRV) was engineered to carry and deliver guide RNA into *Nicotiana benthamiana* plants overexpressing Cas9 endonuclease. In the context of the present disclosure, a guide RNA may be derived from any of the sequences disclosed herein and the teaching of WO2015/189693 applied to edit the genome of a plant cell and obtain a desired mutant plant. The fast pace of the development of the technology has generated a great variety of protocols with broad applicability in plantae, which have been well catalogued in a number of recent scientific review articles (for example, *Plant Methods* (2016) 12:8; and *Front Plant Sci*. (2016) 7:506). A review of CRISPR/Cas systems with a particular focus on its application is described in *Biotechnology Advances* (2015) 33, 1, 41-52). More recent developments in the use of CRISPR/Cas for manipulating plant genomes are discussed in *Acta Pharmaceutica Sinica B* (2017) 7, 3, 292-302 and *Curr. Op. in Plant Biol*. (2017) 36, 1-8. CRISPR/Cas9 plasmids for use in plants are listed in “addgene”, the non-profit plasmid repository (addgene.org), and CRISPR/Cas plasmids are commercially available.

h. Antisense Modification

Antisense technology is another well-known method that can be used to modulate the expression of a polypeptide. A polynucleotide of the gene to be repressed is cloned and operably linked to a regulatory region and a transcription termination sequence so that the antisense strand of RNA is transcribed. The recombinant construct is then transformed into a plant cell and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' polynucleotide. The construction and production of hammerhead ribozymes is known in the art. Hammerhead ribozyme sequences can be embedded in a stable RNA such as a transfer RNA (tRNA) to increase cleavage efficiency in vivo.

In one embodiment, the sequence-specific polynucleotide that can interfere with the translation of RNA transcript(s) is interfering RNA. RNA interference or RNA silencing is an evolutionarily conserved process by which specific mRNAs can be targeted for enzymatic degradation. A double-stranded RNA (double-stranded RNA) is introduced or produced by a cell (for example, double-stranded RNA virus, or interfering RNA polynucleotides) to initiate the interfering RNA pathway. The double-stranded RNA can be converted into multiple small interfering RNA (siRNA) duplexes of 21-24 bp length by RNases III, which are double-stranded RNA-specific endonucleases. The siRNAs can be subsequently recognized by RNA-induced silencing complexes that promote the unwinding of siRNA through an ATP-dependent process. The unwound antisense strand of the siRNA guides the activated RNA-induced silencing complexes to the targeted mRNA comprising a sequence complementary to the siRNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the siRNA strand. The activated RNA-induced silencing complexes can be recycled to catalyze another cleavage event.

Interfering RNA expression vectors may comprise interfering RNA constructs encoding interfering RNA polynucleotides that exhibit RNA interference by reducing the expression level of mRNAs, pre-mRNAs, or related RNA variants. The expression vectors may comprise a promoter positioned upstream and operably-linked to an Interfering RNA construct, as further described herein. Interfering RNA expression vectors may comprise a suitable minimal core promoter, a Interfering RNA construct of interest, an upstream (5') regulatory region, a downstream (3') regulatory region, including transcription termination and polyadenylation signals, and other sequences known to persons skilled in the art, such as various selection markers.

The double-stranded RNA molecules may include siRNA molecules assembled from a single oligonucleotide in a stem-loop structure, wherein self-complementary sense and antisense regions of the siRNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating interfering RNA.

The use of small hairpin RNA molecules is also contemplated. They comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated polynucleotide that is situated between two complementary polynucleotides regions which, when annealed into a double-stranded polynucleotide, comprise a small hairpin RNA. The spacer sequence generally comprises between about 3 and about 100 nucleotides.

Any RNA polynucleotide of interest can be produced by selecting a suitable sequence composition, loop size, and stem length for producing the hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA or ssRNA molecule is between about 15 and about 40 nucleotides in length. In another embodiment, the siRNA molecule is a double-stranded RNA or ssRNA molecule between about 15 and about 35 nucleotides in length. In another embodiment, the siRNA molecule is a double-stranded RNA or ssRNA molecule between about 17 and about 30 nucleotides in length. In another embodiment, the siRNA molecule is a double-stranded RNA or ssRNA molecule between about 19 and about 25 nucleotides in length. In another embodiment, the siRNA molecule is a double-stranded RNA or ssRNA molecule between about 21 to about 23 nucleotides in length. In certain embodiments, hairpin structures with duplexed regions longer than 21 nucleotides may promote effective siRNA-directed silencing, regardless of loop sequence and length. Exemplary sequences for RNA interference are described herein.

The target mRNA sequence is typically between about 14 to about 50 nucleotides in length. The target mRNA can, therefore, be scanned for regions between about 14 and about 50 nucleotides in length that preferably meet one or more of the following criteria: an A+T/G+C ratio of between about 2:1 and about 1:2; an AA dinucleotide or a CA dinucleotide at the 5' end; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected sequence is unique to the target mRNA. Alternatively, a sequence can be selected (and a siRNA sequence designed) using computer software available commercially (for example, OligoEngine, Target Finder and the siRNA Design Tool which are commercially available).

In one embodiment, target mRNA sequences are selected that are between about 14 and about 30 nucleotides in length that meet one or more of the above criteria. In another embodiment, sequences are selected that are between about 16 and about 30 nucleotides in length that meet one or more of the above criteria. In a further embodiment, sequences are selected that are between about 19 and about 30 nucleotides in length that meet one or more of the above criteria. In another embodiment, sequences are selected that are between about 19 and about 25 nucleotides in length that meet one or more of the above criteria.

In an exemplary embodiment, the siRNA molecules comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the polynucleotides described herein.

The specific antisense sequence comprised by the siRNA molecule can be identical or substantially identical to the complement. In one embodiment, the specific antisense sequence comprised by the siRNA molecule is at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

One method for inducing double stranded RNA-silencing in plants is transformation with a gene construct producing hairpin RNA (see *Nature* (2000) 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (*Plant J.* (2001), 27, 581-590). Suitably, the stem length is about 50 nucleotides to about 1 kilobases in length. Methods for producing intron spliced hairpin RNA are well described in the art (see for example, *Bioscience, Biotechnology, and Biochemistry* (2008) 72, 2, 615-617).

Interfering RNA molecules having a duplex or double-stranded structure, for example double-stranded RNA or small hairpin RNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the interfering RNA molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the interfering RNA molecule comprises a 3' overhang at one end of the molecule, the other end can be blunt-ended or have also an overhang (5' or 3'). When the interfering RNA molecule comprises an overhang at both ends of the molecule, the length of the overhangs may be the same or different. In one embodiment, the interfering RNA molecule comprises 3' overhangs of about 1 to about 3 nucleotides on both ends of the molecule. In a further embodiment, the interfering RNA molecule is a double-stranded RNA having a 3' overhang of 2 nucleotides at both ends of the molecule. In yet another embodiment, the nucleotides comprising the overhang of the interfering RNA are TT dinucleotides or UU dinucleotides.

The interfering RNA molecules can comprise one or more 5' or 3'-cap structures. The term "cap structure" refers to a chemical modification incorporated at either terminus of an oligonucleotide, which protects the molecule from exonuclease degradation, and may also facilitate delivery or localisation within a cell.

Another modification applicable to interfering RNA molecules is the chemical linkage to the interfering RNA molecule of one or more moieties or conjugates which enhance the function, cellular distribution, cellular uptake, bioavailability or stability of the interfering RNA molecule. The polynucleotides may be synthesized or modified by methods well established in the art. Chemical modifications include 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages.

The nucleotides at one or both of the two single strands may be modified to modulate the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate.

Ligands may be conjugated to an interfering RNA molecule, for example, to enhance its cellular absorption. In certain embodiments, a hydrophobic ligand is conjugated to the molecule to facilitate direct permeation of the cellular membrane. In certain instances, conjugation of a cationic ligand to oligonucleotides often results in improved resistance to nucleases.

"Targeted Induced Local Lesions In Genomes" (TILLING) is another mutagenesis technology that can be used to generate and/or identify polynucleotides encoding polypeptides with modified expression, function or activity. TILLING also allows selection of plants carrying such mutants. TILLING combines high-density mutagenesis with high-throughput screening methods. Methods for TILLING are well known in the art (see McCallum et al., (2000) *Nat Biotechnol* 18: 455-457 and Stemple (2004) *Nat Rev Genet* 5(2): 145-50).

Various embodiments are directed to expression vectors comprising one or more of the polynucleotides or interfering RNA constructs that comprise one or more polynucleotides described herein.

Various embodiments are directed to expression vectors comprising one or more of the polynucleotides or one or more interfering RNA constructs described herein.

Various embodiments are directed to expression vectors comprising one or more polynucleotides or one or more interfering RNA constructs encoding one or more interfering RNA polynucleotides described herein that are capable of self-annealing to form a hairpin structure, in which the construct comprises (a) one or more of the polynucleotides described herein; (b) a second sequence encoding a spacer element that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed sequences can be utilised for constructing various polynucleotides that do not form hairpin structures. For example, a double-stranded RNA can be formed by (1) transcribing a first strand of the DNA by operably-linking to a first promoter, and (2) transcribing the reverse complementary sequence of the first strand of the DNA fragment by operably-linking to a second promoter. Each strand of the polynucleotide can be transcribed from the same expression vector, or from different expression vectors. The RNA duplex having RNA interference can be enzymatically converted to siRNAs to modulate RNA levels.

Thus, various embodiments are directed to expression vectors comprising one or more polynucleotides or interfering RNA constructs described herein encoding interfering RNA polynucleotides capable of self-annealing, in which the construct comprises (a) one or more of the polynucleotides described herein; and (b) a second sequence comprising a complementary (for example, reverse complementary) sequence of the first sequence, positioned in the same orientation as the first sequence.

Various compositions and methods are provided for modulating the endogenous expression levels of one or more of the polypeptides described herein (or any combination thereof as described herein) by promoting co-suppression of gene expression.

Various compositions and methods are provided for modulating the endogenous gene expression level by modulating the translation of mRNA. A host (tobacco) plant cell can be transformed with an expression vector comprising: a promoter operably-linked to a polynucleotide, positioned in anti-sense orientation with respect to the promoter to enable the expression of RNA polynucleotides having a sequence complementary to a portion of mRNA.

Various expression vectors for modulating the translation of mRNA may comprise: a promoter operably-linked to a polynucleotide in which the sequence is positioned in anti-sense orientation with respect to the promoter. The lengths of anti-sense RNA polynucleotides can vary, and may be from about 15-20 nucleotides, about 20-30 nucleotides, about 30-50 nucleotides, about 50-75 nucleotides, about 75-100 nucleotides, about 100-150 nucleotides, about 150-200 nucleotides, and about 200-300 nucleotides.

i. Mobile Genetic Elements

Alternatively, genes can be targeted for inactivation by introducing transposons (for example, IS elements) into the genomes of plants of interest. These mobile genetic elements can be introduced by sexual cross-fertilization and insertion mutants can be screened for loss in polypeptide function. The disrupted gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more genes can be inactivated by the insertion of one or more transposons. Mutations can result in homozygous disruption of one or more genes, in heterozygous disruption of one or more genes, or a combination of both homozygous and heterozygous disruptions if more than one gene is disrupted. Suitable transposable elements include retrotransposons, retroposons, and SINE-like elements. Such methods are known to persons skilled in the art.

j. Ribozymes

Alternatively, genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, *Solanum nodiflorum* mottle virus, and subterranean clover mottle virus. Various target RNA-specific ribozymes are known to persons skilled in the art.

The mutant or non-naturally occurring plants or plant cells can have any combination of one or more mutations in one or more genes which results in modulated expression or function or activity of those genes or their products. For example, the mutant or non-naturally occurring plants or plant cells may have a single mutation in a single gene; multiple mutations in a single gene; a single mutation in two or more or three or more or four or more genes; or multiple mutations in two or more or three or more or four or more genes. Examples of such mutations are described herein. By way of further example, the mutant or non-naturally occurring plants or plant cells may have one or more mutations in a specific portion of the gene(s)—such as in a region of the gene that encodes an active site of the polypeptide or a portion thereof. By way of further example, the mutant or non-naturally occurring plants or plant cells may have one or more mutations in a region outside of one or more gene(s)—such as in a region upstream or downstream of the gene it regulates provided that they modulate the function or expression of the gene(s). Upstream elements can include promoters, enhancers or transcription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants or plant cells may have one or more mutations located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants or plant cells may have one or more mutations located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants or plant cells (for example, mutant, non-naturally occurring or transgenic plants or plant cells and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant polynucleotide is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

Preparation of Modified Plants, Screening, and Crossing

Prepared polynucleotide from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the samples are optionally pooled, they can be subjected to polynucleotide-specific amplification techniques, such as PCR. Any one or more primers or probes specific to the gene or the sequences immediately adjacent to the gene may be utilized to amplify the sequences within the optionally pooled sample. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art.

Polymorphisms may be identified by means known in the art and some have been described in the literature.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. See, for example, *Plant Cell Reports* (1986) 5:81-84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Thus as used herein, "transformed seeds" refers to seeds that contain the nucleotide construct stably integrated into the plant genome.

Accordingly, in a further aspect there is provided a method of preparing a mutant plant. The method involves providing at least one cell of a plant comprising a gene encoding a functional polynucleotide described herein (or any combination thereof as described herein). Next, the at least one cell of the plant is treated under conditions effective to modulate the function of the polynucleotide(s) described herein. The at least one mutant plant cell is then propagated into a mutant plant, where the mutant plant has a modulated level of polypeptide(s) described (or any combination thereof as described herein) as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutant plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. The same technique can also be applied to the introgression of one or more non-naturally occurring mutation(s) from a first plant into a second plant. Plants showing a desired trait may be screened out of a pool of mutant plants. Suitably, the selection is carried out utilising the knowledge of the polynucleotide as described herein. Consequently, it is possible to screen for a genetic trait as compared to a control. Such a screening approach may involve the application of conventional amplification and/or hybridization techniques as discussed herein. Thus, a further aspect of the present disclosure relates to a method for identifying a mutant plant comprising the steps of: (a) providing a sample comprising polynucleotide from a plant; and (b) determining the sequence of the polynucleotide, wherein a difference in the sequence of the polynucleotide as compared to the polynucleotide of a control plant is indicative that said plant is a mutant plant. In another aspect there is provided a method for identifying a mutant plant which accumulates increased or decreased levels of one or more amino acids as compared to a control plant comprising the steps of: (a) providing a sample from a plant to be screened; (b) determining if said sample comprises one or more mutations in one or more of the polynucleotides described herein; and (c) determining the level of at least one amino acid of said plant. In another aspect there is provided a method for preparing a mutant plant which has increased or decreased levels of at least one amino acid as compared to a control plant comprising the steps of: (a) providing a sample from a first plant; (b) determining if said sample comprises one or more mutations in one or more the polynucleotides described herein that result in modulated levels of at least one amino acid; and (c) transferring the one or more mutations into a second plant. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which has increased or decreased levels of at least one amino acid as compared to a control plant comprising the steps of: (a) providing a sample from a first plant; (b) determining if said sample comprises one or more mutations in one or more of the polynucleotides described herein that results in modulated levels of at least one amino acid; and (c) introgressing the one or more mutations from the first plant into a second plant. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein. In certain embodiments, the "mutant plants" may have one or more mutations localised only to a specific region of the plant—such as within the sequence of the one or more polynucleotide(s) described herein. According to this embodiment, the remaining genomic sequence of the mutant plant will be the same or substantially the same as the plant prior to the mutagenesis.

In certain embodiments, the mutant plants may have one or more mutations localised in more than one genomic region of the plant—such as within the sequence of one or more of the polynucleotides described herein and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the polynucleotide(s) described herein; or may not have one or more mutations in one or more, two or more, three or more, four or more or five or more introns of the polynucleotide(s) described herein; or may not have one or more mutations in a promoter of the polynucleotide(s) described herein; or may not have one or more mutations in the 3' untranslated region of the polynucleotide(s) described herein; or may not have one or more mutations in the 5' untranslated region of the polynucleotide(s) described herein; or may not have one or more mutations in the coding region of the polynucleotide(s) described herein; or may not have one or more mutations in the non-coding region of the polynucleotide(s) described herein; or any combination of two or more, three or more, four or more, five or more; or six or more thereof parts thereof.

In a further aspect there is provided a method of identifying a plant, a plant cell or plant material comprising a mutation in a gene encoding a polynucleotide described herein comprising: (a) subjecting a plant, a plant cell or plant material to mutagenesis; (b) obtaining a sample from said plant, plant cell or plant material or descendants thereof; and (c) determining the polynucleotide sequence of the gene or a variant or a fragment thereof, wherein a difference in said sequence is indicative of one or more mutations therein. This method also allows the selection of plants having mutation(s) that occur(s) in genomic regions that affect the expression of the gene in a plant cell, such as a transcription initiation site, a start codon, a region of an intron, a boundary of an exon-intron, a terminator, or a stop codon.

Plant Families, Species, Varieties, Seeds, and Tissue Culture

Plants suitable for use in genetic modification include monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), *Triticosecale* (tritic wheat times rye), bamboo, *Helianthus annuus* (sunflower), *Carthamus tinctorius* (safflower), *Jatropha curcas* (*Jatropha*), *Ricinus communis* (castor), *Elaeis guineensis* (palm), *Linum usitatissimum* (flax), *Brassica juncea, Beta vulgaris* (sugarbeet), *Manihot esculenta* (cassaya), *Lycopersicon esculentum* (tomato), *Lactuca sativa* (lettuce), *Musyclise alca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffeycliseca* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (*petunia*), *Poinsettia pulcherrima* (*Poinsettia*), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), *Sorghuycliseor* (*Sorghum*, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant tobacco, non-naturally occurring tobacco or transgenic tobacco plants or plant cells modified to modulate gene expression levels thereby producing a plant or plant cell—such as a tobacco plant or plant cell—in which the expression level of a polypeptide is modulated within tissues of interest as compared to a control. The disclosed compositions and methods can be applied to any species of the genus *Nicotiana*, including *N. rustica* and *N. tabacum* (for example, LA B21, LN KY171, TI 1406, Basma, *Galpao*, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N.*

*miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N.* x *sanderae*. Suitably, the tobacco plant is *N. tabacum.*

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation (s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC *Galpao* tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, P01, P02, P03, RG11, RG 8, VA509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpão Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to modulate the expression or function of a polynucleotide(s) described herein (or any combination thereof as described herein). Advantageously, the mutant plants, non-naturally occurring plants, hybrid plants, or transgenic plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a polynucleotide conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include cells from leaves, pollen, embryos, cotyledons, hypocotyls, roots, root tips, anthers, flowers and a part thereof, ovules, shoots, stems, stalks, pith and capsules or callus or protoplasts derived therefrom. The plant material that is described herein can be cured tobacco material—such as air cured or sun-cured tobacco material. Examples of air and sun cured tobacco varieties are the Burley type and Dark type. The plant material that is described herein can be flue cured tobacco material—such as Virginia type.

The CORESTA recommendation for tobacco curing is described in: CORESTA Guide No. 17, April 2016, Sustainability in Leaf Tobacco Production.

One object is to provide mutant, transgenic or non-naturally occurring plants or parts thereof that exhibit modulated levels of NtAAT which results in modulated levels at least one amino acid—such as aspartate—in the plant material, for example, in cured leaves. Since aspartate is known to result in acrylamide upon heating of tobacco leaf modulating the levels of aspartate may also lead to the modulation of acrylamide levels. The synthesis of aspartate is also essential for the synthesis of other amino acids—such as asparagine, threonine, isoleucine, cysteine and methionine. Accordingly, the levels of one or more of these other amino acids may be modulated when the levels of aspartate are modulated. Certain amino acids—such as threonine, methionine and cysteine—can result in a sulphur-odor in smoke or aerosols that are produced heating. Modulating these amino acid levels therefore also allows for the modulation of this sulphur-odor.

In certain embodiments the activity and/or expression of or more of NtAAT1-S, NtAAT1-T, NtAAT2-S, NtAAT2-T, NtAAT3-S, NtAAT3-T, NtAAT4-S and NtAAT4-T is modulated.

In certain embodiments, the activity and/or expression of or more of NtAAT1-S and NtAAT1-T, is modulated.

In certain embodiments, the activity and/or expression of or more of NtAAT2-S and NtAAT2-T, is modulated.

In certain embodiments, the activity and/or expression of or more of NtAAT1-S, NtAAT1-T, NtAAT2-S and NtAAT2-T is modulated.

In certain embodiments, the expression and/or activity of one or more of NtAAT1-S, NtAAT1-T, NtAAT2-S and NtAAT2-T is modulated whereas the expression and/or activity of one or more of NtAAT3-S, NtAAT3-T, NtAAT4-S and NtAAT4-T is not modulated.

In certain embodiments, the expression and/or activity of one or more of NtAAT1-S, NtAAT1-T, NtAAT2-S and NtAAT2-T is modulated whereas the expression and/or activity of NtAAT3-S NtAAT3-T, NtAAT4-S and NtAAT4-T is not modulated.

Suitably, the mutant, transgenic or non-naturally occurring plants or parts thereof have substantially the same visual appearance as the control plant.

Accordingly, there is described herein mutant, transgenic or non-naturally occurring plants or parts thereof or plant cells that have modulated levels of at least one amino acid compared to control cells or control plants. The mutant, transgenic or non-naturally occurring plants or plant cells have been modified to modulate the synthesis or function of one or more of the polypeptides described herein by modulating the expression of one or more of the corresponding polynucleotides described herein. Suitably, the modulated levels of at least one amino acid are observed in at least the green leaves, suitably cured leaves.

A further aspect, relates to a mutant, non-naturally occurring or transgenic plant or cell, wherein the expression or the function of one or more of the AAT polypeptides described herein is modulated (for example, decreased) and a part of the plant (for example, the green leaves, suitably cured leaves or cured tobacco) has modulated (for example, decreased) levels of at least one amino acid of at least 5% therein as compared to a control plant in which the expression or the function of said polypeptide(s) has not been modulated (for example, decreased). In certain embodiments, the level of at least one amino acid in the plant—such as the green leaves, suitably cured leaves or cured tobacco—may be modulated (for example, decreased), for example, by at least 5%, at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or, or at least 150%, or at least 200% more of a quantity or a function. The level of at least one amino acid may be decreased to undetectable amounts.

A still further aspect, relates to a cured plant material—such as cured leaf or cured tobacco—derived or derivable from a mutant, non-naturally occurring or transgenic plant or cell, wherein expression of one or more of the polynucleotides described herein or the function of the polypeptide encoded thereby is modulated (for example, decreased) and wherein the level of at least one amino acid is modulated (for example, decreased) by at least 5%, at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or, or at least 150%, or at least 200% as compared to a control plant.

Suitably the visual appearance of said plant or part thereof (for example, leaf) is substantially the same as the control plant. Suitably, the plant is a tobacco plant or a coffee plant.

Embodiments are also directed to compositions and methods for producing mutant, non-naturally occurring or transgenic plants or plant cells that have been modified to modulate the expression or function of the one or more of the polynucleotides or polypeptides described herein which can result in plants or plant components (for example, leaves—such as green leaves or cured leaves—or tobacco) or plant cells with modulated content of at least one amino acid.

The mutant, non-naturally occurring or transgenic plants can be similar or substantially the same in visual appearance to the corresponding control plants. In one embodiment, the leaf weight of the mutant, non-naturally occurring or transgenic plant is substantially the same as the control plant. In one embodiment, the leaf number of the mutant, non-naturally occurring or transgenic plant is substantially the same as the control plant. In one embodiment, the leaf weight and the leaf number of the mutant, non-naturally occurring or transgenic plant is substantially the same as the control plant. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or colouration of the leaves of the mutant, non-naturally occurring or transgenic plants is substantially the same as the control plants. Suitably, the plant is a tobacco plant or a coffee plant.

In another aspect, there is provided a method for modulating the amount of at least one amino acid in at least a part of a plant (for example, the leaves—such as cured leaves—or in tobacco), comprising the steps of: (i) modulating the expression or function of an one or more of the polypeptides described herein (or any combination thereof as described herein), suitably, wherein the polypeptide(s) is encoded by the corresponding polynucleotides described herein; (ii) measuring the level of the at least one amino acid in at least a part (for example, the leaves—such as cured leaves—or tobacco or in smoke) of the mutant, non-naturally occurring or transgenic plant obtained in step (i); and (iii) identifying a mutant, non-naturally occurring or transgenic plant in which the level of the at least one amino acid therein has been modulated in comparison to a control plant. Suitably, the visual appearance of said mutant, non-naturally occurring or transgenic plant is substantially the same as the control plant. Suitably, the plant is a tobacco plant.

In another aspect, there is provided a method for modulating the amount of at least one amino acid in at least a part of cured plant material—such as cured leaf—comprising the steps of: (i) modulating the expression or function of an one or more of the polypeptides (or any combination thereof as described herein), suitably, wherein the polypeptide(s) is encoded by the corresponding polynucleotides described herein; (ii) harvesting plant material—such as one or more of the leaves—and curing for a period of time; (iii) measuring the level of the at least one amino acid in at least a part of the cured plant material obtained in step (ii) or during step (ii); and (iv) identifying cured plant material in which the level of the at least one amino acid therein has been modulated in comparison to a control plant.

An increase in expression as compared to the control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more, which includes an increase in transcriptional function or polynucleotide expression or polypeptide expression or a combination thereof.

An increase in function or activity as compared to a control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more.

A reduction in expression as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional function or polynucleotide expression or polypeptide expression or a combination thereof. Suitably, expression is decreased.

A reduction in function or activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%. Suitably, function or activity is decreased.

Polynucleotides and recombinant constructs described herein can be used to modulate the expression or function or activity of the polynucleotides or polypeptides described herein in a plant species of interest, suitably tobacco.

A number of polynucleotide based methods can be used to increase gene expression in plants and plant cells. By way of example, a construct, vector or expression vector that is compatible with the plant to be transformed can be prepared which comprises the gene of interest together with an upstream promoter that is capable of overexpressing the gene in the plant or plant cell. Exemplary promoters are described herein. Following transformation and when grown under suitable conditions, the promoter can drive expression in order to modulate the levels of this enzyme in the plant, or in a specific tissue thereof. In one exemplary embodiment, a vector carrying one or more polynucleotides described herein (or any combination thereof as described herein) is generated to overexpress the gene in a plant or plant cell. The vector carries a suitable promoter—such as the cauliflower mosaic virus CaMV 35S promoter—upstream of the transgene driving its constitutive expression in all tissues of the plant. The vector also carries an antibiotic resistance gene in order to confer selection of the transformed calli and cell lines.

The expression of sequences from promoters can be enhanced by including expression control sequences, including enhancers, chromatin activating elements, transcription factor responsive elements and the like. Such control sequences may be constitutive, and upregulate transcription in a universal manner; or they may be facultative, and upregulate transcription in response to specific signals. Signals associated with senescence and signals which are active during the curing procedure are specifically indicated.

Various embodiments are therefore directed to methods for modulating the expression level of one or more polynucleotides described herein (or any combination thereof as described herein) by integrating multiple copies of the polynucleotide into a plant genome, comprising: transforming a plant cell host with an expression vector that comprises a promoter operably-linked to one or more polynucleotides described herein. The polypeptide encoded by a recombinant polynucleotide can be a native polypeptide, or can be heterologous to the cell.

In one embodiment, the plant of use in the present disclosure is a plant that is air-cured as such plants have a high amino acid content (greater than about 27.4 mg/g dry weight free amino acid content when field grown) and a high ammonia content (greater than about 0.18% dry weight when field grown) at the end of curing. Mutant, transgenic or non-naturally occurring plants or parts thereof that are air-cured can have an amino acid content that is less than about 27.4 mg/g dry weight free amino acid content when field grown at the end of curing—such as less than about 20 mg/g dry weight free amino acid content when field grown at the end of curing, or less than about 15 mg/g dry weight free amino acid content when field grown at the end of curing, or less than about 10 mg/g dry weight free amino acid content when field grown at the end of curing, or less than about 5 mg/g dry weight free amino acid content when field grown at the end of curing. Mutant, transgenic or non-naturally occurring plants or parts thereof that are air-cured can have an ammonia content that is less than about 0.18% dry weight when field grown at the end of curing, or less than about 0.15% dry weight when field grown at the end of curing, or less than about 0.10% dry weight when field grown at the end of curing, or less than about 0.05% dry weight when field grown at the end of curing.

In another embodiment, the plant of use in the present disclosure is a plant that is sun-cured as such plants have a high amino acid content (greater than about 26.5 mg/g dry weight free amino acid content when field grown at the end of curing) and a high ammonia content (greater than about 0.14% dry weight when field grown at the end of curing). Mutant, transgenic or non-naturally occurring plants or parts thereof that are sun-cured can have an amino acid content that is less than about 26.5 mg/g dry weight free amino acid content when field grown at the end of curing—such as less than about 20 mg/g dry weight free amino acid content when field grown at the end of curing, or less than about 20 mg/g dry weight free amino acid content when field grown at the end of curing, or less than about 15 mg/g dry weight free amino acid content when field grown at the end of curing, or less than about 10 mg/g dry weight free amino acid content when field grown at the end of curing, or less than about 5 mg/g dry weight free amino acid content when field grown at the end of curing. Mutant, transgenic or non-naturally occurring plants or parts thereof that are sun-cured can have an ammonia content that is less than about 0.14% dry weight when field grown at the end of curing, or less than about 0.10% dry weight when field grown at the end of curing, or less than about 0.05% dry weight when field grown at the end of curing.

In another embodiment, the plant of use in the present disclosure is a plant that is flue-cured. Such plants have an amino acid content that is greater than about 3 mg/g dry weight free amino acid content when field grown at the end of curing) and an ammonia content that is greater than about 0.02% dry weight when field grown at the end of curing). Mutant, transgenic or non-naturally occurring plants or parts thereof that are flue-cured can have an amino acid content that is less than about 3 mg/g dry weight free amino acid content when field grown at the end of curing—such as less than about 2.5 mg/g dry weight free amino acid content when field grown at the end of curing, or less than about 2.0 mg/g dry weight free amino acid content when field grown at the end of curing, or less than about 1.5 mg/g dry weight free amino acid content when field grown at the end of curing, or less than about 1.0 mg/g dry weight free amino acid content when field grown at the end of curing, or less than about 0.5 mg/g dry weight free amino acid content when field grown at the end of curing. Mutant, transgenic or non-naturally occurring plants or parts thereof that are sun-cured can have an ammonia content that is less than about 0.02% dry weight when field grown at the end of curing, or less than about 0.10% dry weight when field grown at the end of curing, or less than about 0.05% dry weight when field grown at the end of curing.

In certain embodiments, the use of plants that are air-cured or sun-cured is preferred.

Amino acid content can be measured using various methods that are known in the art. One such method is Method MP 1471 rev 5 2011, Resana, Italy: Chelab Silliker S.r.l, Mérieux NutriSciences Company. For amino acid determination in cured plant leaves, after mid-rib removal, cured lamina are dried at 40° C. for 2-3 days, if required. Tobacco material is then ground in fine powder (~100 uM) before the analysis of amino acid content. Another method for measuring amino acid content in plant material is described in UNI EN ISO 13903:2005. In one embodiment, the method used to measure amino acid content in plant material is described in UNI EN ISO 13903:2005

Ammonia content can be determined by Skalar: MT24-Nitrate, Total Alkaloids, Ammonia, Chloride, TKN. For ammonia determination in cured plant leaves, after mid-rib removal, cured lamina are dried at 40° C. for 2-3 days, if required. Tobacco material is then ground in fine powder (~100 uM) before the analysis of ammonia content. Other methods for measuring ammonia content are known in the art and include the methods described in: Health Canada (1999) Determination of ammonia in whole tobacco. Tobacco Control Programme. Health Canada Official Method T-302; and Tobacco Manufacturers Organization (2002) UK smoke constituent study. Annex A Part 5 Method: determination of ammonia yields in mainstream cigarette smoke using the Dionex DX-500 ion chromatograph, Report Nr GC15/M24/02.

A plant carrying a mutant allele of one or more polynucleotides described herein (or any combination thereof as described herein) can be used in a plant breeding program to create useful lines, varieties and hybrids. In particular, the mutant allele is introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring plant comprising: (a) crossing a mutant or transgenic plant with a second plant to yield progeny tobacco seed; (b) growing the progeny tobacco seed, under plant growth conditions, to yield the non-naturally occurring plant. The method may further comprises: (c) crossing the previous generation of non-naturally occurring plant with itself or another plant to yield progeny tobacco seed; (d) growing the progeny tobacco seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly plant breeding, are well known and can be used in the methods of the disclosure. The disclosure further provides non-naturally occurring plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other tobaccos, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the polynucleotide sequence information for the polynucleotide(s) described herein (or any combination thereof as described herein).

Hybrid tobacco varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross tobacco F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression or function of the polypeptide(s) encoded thereby.

Physical and biochemical methods can be used to identify expression or activity levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme function of polypeptides and polynucleotides; and polypeptide gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression, function or activity of polypeptides or polynucleotides.

Mutant, non-naturally occurring or transgenic plant cells and plants are described herein comprising one or more recombinant polynucleotides, one or more polynucleotide constructs, one or more double-stranded RNAs, one or more conjugates or one or more vectors/expression vectors.

Without limitation, the plants and parts thereof described herein can be modified either before or after the expression, function or activity of the one or more polynucleotides and/or polypeptides according to the present disclosure have been modulated.

One or more of the following further genetic modifications can be present in the mutant, non-naturally occurring or transgenic plants and parts thereof.

One or more genes that are involved in the conversion of nitrogenous metabolic intermediates can be modified resulting in lower levels of at least one tobacco-specific nitrosamine (TSNA). Non-limiting examples of such genes include those encoding nicotine demethylase—such as CYP82E4, CYP82E5 and CYP82E10 as described in WO2006/091194, WO2008/070274, WO2009/064771 and WO2011/088180—and nitrate reductase, as described in WO2016046288.

One or more genes that are involved in heavy metal uptake or heavy metal transport can be modified resulting in lower heavy metal content. Non-limiting examples include genes in the family of multidrug resistance associated polypeptides, the family of cation diffusion facilitators (CDF), the family of Zrt-Irt-like polypeptides (ZIP), the family of cation exchangers (CAX), the family of copper transporters (COPT), the family of heavy-metal ATPases (for example, HMAs, as described in WO2009/074325 and WO2017/129739), the family of homologs of natural resistance-associated macrophage polypeptides (NRAMP), and other members of the family of ATP-binding cassette (ABC) transporters (for example, MRPs), as described in WO2012/028309, which participate in transport of heavy metals—such as cadmium.

Other exemplary modifications can result in plants with modulated expression or function of isopropylmalate synthase which results in a change in sucrose ester composition which can be used to alter favour profile (see WO2013/029799).

Other exemplary modifications can result in plants with modulated expression or function of threonine synthase in which levels of methional can be modulated (see WO2013/029800).

Other exemplary modifications can result in plants with modulated expression or function of one or more of neoxanthin synthase, lycopene beta cyclase and 9-cis-epoxycarotenoid dioxygenase to modulate beta-damascenone content to alter flavour profile (see WO2013/064499).

Other exemplary modifications can result in plants with modulated expression or function of members of the CLC family of chloride channels to modulate nitrate levels therein (see WO2014/096283 and WO2015/197727).

Other exemplary modifications can result in plants with modulated expression or function of one or more AATs to modulate levels of one or more amino acids—such as aspartate—in leaf and modulated levels of acrylamide in aerosol produced upon heating or combusting the leaf (see WO2017042162).

Examples of other modifications include modulating herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB polypeptide of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae.*

Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single polypeptide and significantly delayed the evolution of resistant insects.

Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered.

Another exemplary modification results in altered reproductive capability, such as male sterility.

Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance.

Another exemplary modification results in plants in which the activity of one or more endogenous glycosyltransferases—such as N-acetylglucosaminyltransferase, β(1,2)-xylosyltransferase and a(1,3)-fucosyl-transferase is modulated (see WO/2011/117249).

Another exemplary modification results in plants in which the activity of one or more nicotine N-demethylases is modulated such that the levels of nornicotine and metabolites of nornicotine—that are formed during curing can be modulated (see WO2015169927).

Other exemplary modifications can result in plants with improved storage polypeptides and oils, plants with enhanced photosynthetic efficiency, plants with prolonged shelf life, plants with enhanced carbohydrate content, and plants resistant to fungi. Transgenic plants in which the expression of S-adenosyl-L-methionine (SAM) and/or cystathionine gamma-synthase (CGS) has been modulated are also contemplated.

One or more genes that are involved in the nicotine synthesis pathway can be modified resulting in plants or parts of plants that when cured, produce modulated levels of nicotine. The nicotine synthesis genes can be selected from the group consisting of: A622, 88La, 88Lb, JRE5L1, JRE5L2, MATE1, MATE 2, MPO1, MPO2, MYC2a, MYC2b, NBB1, nic1, nic2, NUP1, NUP2, PMT1, PMT2, PMT3, PMT4 and QPT or a combination of one or more thereof.

One or more genes that are involved in controlling the amount of one or more alkaloids can be modified resulting in plants or parts of plants that produce modulated levels of alkaloid. Alkaloid level controlling genes can be selected from the group consisting of; BBLa, BBLb, JRE5L1, JRE5L2, MATE1, MATE 2, MYC2a, MYC2b, nic1, nic2, NUP1 and NUP2 or a combination of two or more thereof.

One or more such traits may be introgressed into the mutant, non-naturally occurring or transgenic plants from another cultivar or may be directly transformed into it.

Various embodiments provide mutant plants, non-naturally occurring plants or transgenic plants, as well as biomass in which the expression level of one or more polynucleotides according to the present disclosure are modulated to thereby modulate the level of polypeptide(s) encoded thereby.

Parts of the plants described herein, particularly the leaf lamina and midrib of such plants, can be incorporated into or used in making various consumable products including but not limited to aerosol forming materials, aerosol forming devices, smoking articles, smokable articles, smokeless products, medicinal or cosmetic products, intravenous preparations, tablets, powders, and tobacco products. Examples of aerosol forming materials include tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured plant material from the mutant, transgenic and non-naturally occurring plants described herein. Processes of curing green tobacco leaves are known by those having skills in the art and include without limitation air-curing, fire-curing, flue-curing and sun-curing as described herein.

In another embodiment, there is described tobacco products including tobacco-containing aerosol forming materials comprising plant material—such as leaves, preferably cured leaves—from the mutant tobacco plants, transgenic tobacco plants or non-naturally occurring tobacco plants described herein. The tobacco products described herein can be a blended tobacco product which may further comprise unmodified tobacco.

Products and Methods for Crop Management and Agriculture

The mutant, non-naturally occurring or transgenic plants may have other uses in, for example, agriculture. For example, mutant, non-naturally occurring or transgenic plants described herein can be used to make animal feed and human food products.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a polynucleotide (or any combination thereof as described herein) in a sample of polynucleotide. Accordingly, a composition is described comprising one or more primers for specifically amplifying at least a portion of one or more of the polynucleotides and optionally one or more probes and optionally one or more reagents for conducting the amplification or detection.

Accordingly, gene specific oligonucleotide primers or probes comprising about 10 or more contiguous polynucleotides corresponding to the polynucleotide(s) described herein are disclosed. Said primers or probes may comprise or consist of about 15, 20, 25, 30, 40, 45 or 50 more contiguous polynucleotides that hybridise (for example, specifically hybridise) to the polynucleotide(s) described herein. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in amplification or detection). The one or more specific primers or probes can be designed and used to amplify or detect a part or all of the polynucleotide(s). By way of specific example, two primers may be used in a PCR protocol to amplify a polynucleotide fragment. The PCR may also be performed using one primer that is derived from a polynucleotide sequence and a second primer that hybridises to the sequence upstream or downstream of the polynucleotide sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a polynucleotide(s) described herein (or any combination thereof as described herein) in a sample comprising the step of: (a) providing a sample comprising, or suspected of comprising, a polynucleotide; (b) contacting said sample with one or more primers or one or more probes for specifically detecting at least a portion of the polynucleotide(s); and (c) detecting the presence of an amplification product, wherein the presence of an amplification product is indicative of the presence of the polynucleotide(s) in the sample. In a further aspect, there is also provided the use of one or more primers or probes for specifically detecting at least a portion of the polynucleotide(s). Kits for detecting at least a portion of the polynucleotide(s) are also provided which comprise one or more primers or probes for specifically detecting at least a portion of the polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for using the kit.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by polynucleotide variability. Thus, the present disclosure further provides a means to follow segregation of one or more genes or polynucleotides as well as chromosomal sequences genetically linked to these genes or polynucleotides using such techniques as AFLP analysis.

The invention is further described in the Examples below, which are provided to describe the invention in further detail. These examples, which set forth a preferred mode presently contemplated for carrying out the invention, are intended to illustrate and not to limit the invention.

EXAMPLES

Example 1: Identification of Key Amino Acid Up-Regulated Genes after Curing in Burley, Virginia and Oriental Tobacco Leaf To identify key functions contributing to free amino acid changes during early curing time of Burley, Virginia and Oriental tobacco leaf, an overrepresentation analysis for the function of genes up-regulated in cured leaves after 48 h curing, as compared to the ripe leaves at harvest (log 2 fold change >2, adjusted p-value <0.05) is performed in Burley, Virginia and Oriental tobacco. Genes involved in the production of free amino acids that are active after 48 h curing independently of the curing types and tobacco varieties are identified. Tobacco genes impacting the production of aspartate during early curing and belonging to the family of AAT are investigated.

The full set of NtAAT polynucleotides is identified in the tobacco genome, which are NtAAT1-S (SEQ ID NO: 5), NtAAT1-T (SEQ ID NO: 7), NtAAT2-S(SEQ ID NO: 1), NtAAT2-T (SEQ ID NO: 3), NtAAT3-S(SEQ ID NO: 9), NtAAT3-T (SEQ ID NO: 11), NtAAT4-S(SEQ ID NO: 13) and NtAAT4-T (SEQ ID NO: 15) and their deduced polypeptide sequences are NtAAT1-S(SEQ ID NO: 6), NtAAT1-T (SEQ ID NO: 8), NtAAT2-S(SEQ ID NO: 2), NtAAT2-T (SEQ ID NO: 4, NtAAT3-S (SEQ ID NO: 10), NtAAT3-T (SEQ ID NO: 12), NtAAT4-S (SEQ ID NO: 14) and NtAAT4-T (SEQ ID NO: 16).

Gene expression analyses shows that NtAAT2-S(SEQ ID NO: 1) and NtAAT2-T (SEQ ID NO: 3) are the most expressed genes (>11×) after 48 h curing in Burley, Virginia and Oriental tobacco as compared to green leaves (see Table 1). Interestingly, NtAAT1-T (SEQ ID NO: 7) is also up-regulated after 48 h curing, but to a lesser extent (>2.5). Only NtAAT2-S and NtAAT2-T are already upregulated in ripe leaves, suggesting that these genes are the main drivers to provide aspartate for asparagine synthesis.

NtAAT2-S and NtAAT2-T genes are not only highly expressed during early leaf curing when chlorophyll is degraded, but also in petal (see Table 2). Their expression is very low in root and leaf (see Table 2) and other tissues, suggesting that the function of NtAAT2-S and NtAAT2-T is linked to a localization in non-chlorophyll above-ground organs. The same observation seems to be also valid for NtAAT1-S and NtAAT1-T but to a lesser extent. Therefore, we cannot exclude that NtAAT1-S and NtAAT1-T also contribute to aspartate synthesis in cured leaf. On the opposite, NtAAT3-S/NtAAT3-T and NtAAT4-S/NtAAT4-T seem to be more constitutively expressed in all plant tissues (see Table 2).

Figure 2:
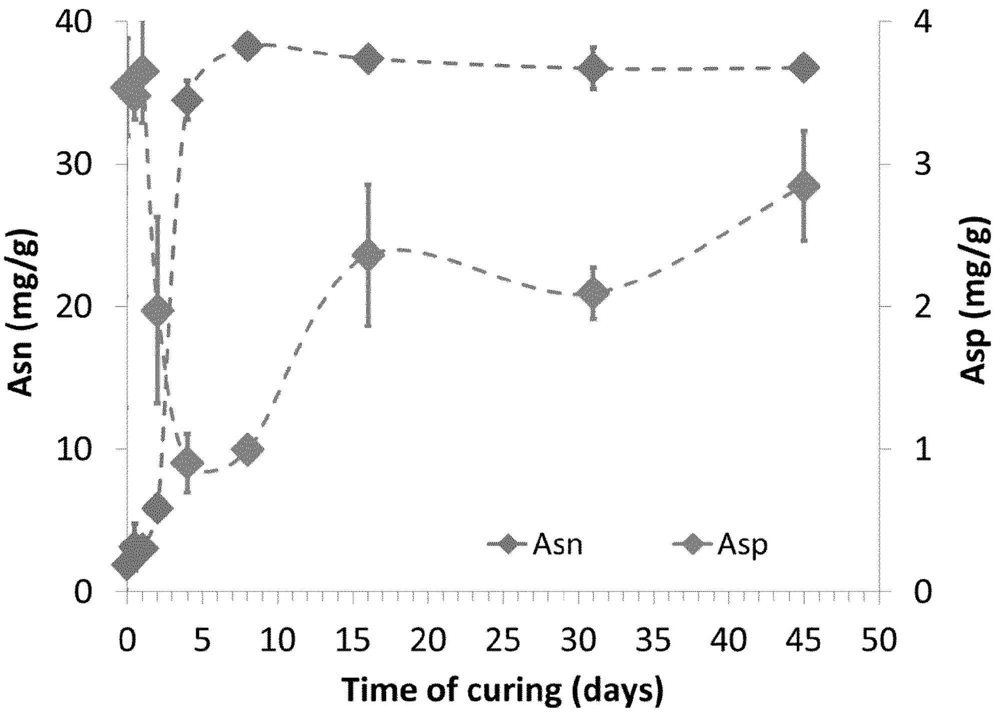
FIG. 2 is a graph showing the post-harvest amounts of aspartate (asp) and asparagine (asn) in leaf samples of Swiss Burley tobacco grown in the field (three bulk leaf replicates). Free amino acids were measured in leaf samples (mid-stalk position) collected in a time-course manner in an air-curing barn till 50 days of curing.

Co-expression analyses confirmed that NtAAT2-S, NtAAT2-T, NtASN1-S and NtASN1-T are co-regulated during the early curing phase. For this, a Burley curing transcriptome database consisting of 34 non-cured and early cured Burley samples was used. 168 genes are found to be co-expressed with NtASN1-S and NtASN1-T and 12 genes with NtAAT2-S and NtAAT2-T (threshold >0.9). Among this transcriptomic set, both NtAAT2-S and NtAAT2-T and NtASN1-S and NtASN1-T transcripts are present in the two sets of RNA sequences (9 sequences in common) associated with 5 other transcripts. Such a co-expression associated with a time-course experiment during curing (see FIG. 2) and co-expression in petals and early cured leaves (see Table 2 and WO2017/042162) suggests that both NtAAT2-S and NtAAT2-T and NtASN1-S and NtASN1-T contribute to nitrate assimilation into amino acids and asparagine in a coordinated manner.

The silencing of NtAAT2-S and NtAAT2-T in Burley tobacco plants is investigated to determine if both genes contribute to decrease aspartate in cured Burley leaves. A specific DNA fragment (SEQ ID NO: 17) within the coding sequence of both NtAAT2-S and NtAAT2-T is cloned with the strong constitutive *Mirabilis* Mosaic Virus (MMV) promoter in a GATEWAY vector. The NtAAT2-S and NtAAT2-T gene fragment is flanked between MMV and the 3' nos terminator sequence of the nopaline synthase gene of *Agrobacterium tumefaciens*. The Burley tobacco line TN90e4e5e10 (Zyvert) is transformed using standard *Agrobacterium*-mediated transformation protocols. TN90e4e5e10 (Zyvert) represents a selection from an ethylmethane sulfonate (EMS) mutagenized Burley population that contains knockout mutations in CYP82E4, CYP82E5v2 and CYP82E10 (see *Phytochemistry* (2010) 71: 17-18), to prevent nornicotine production. Using such a background line can avoid potential complications when interpreting future TSNA data.

Figure 3:
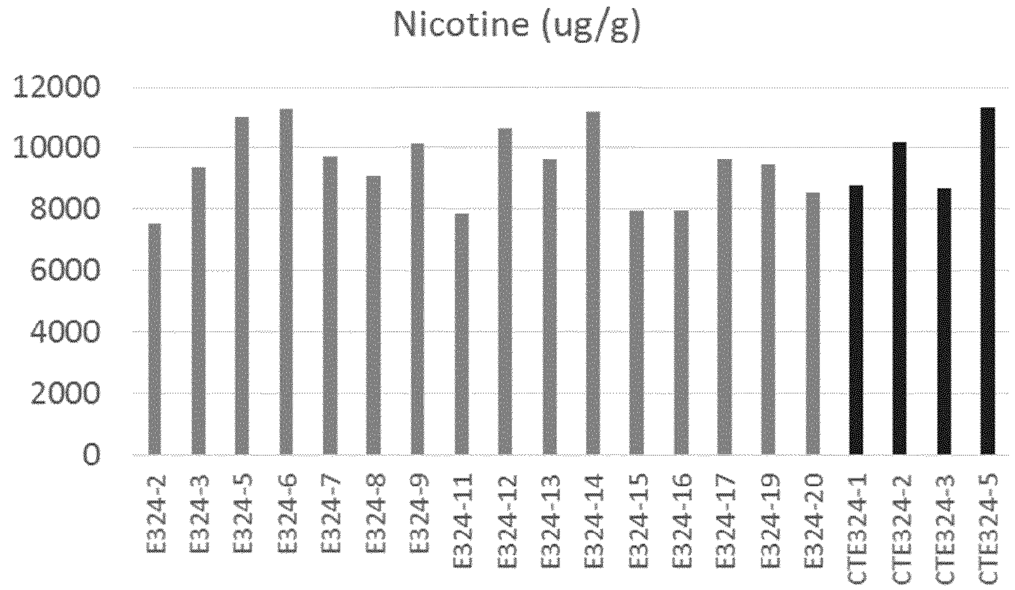
FIG. 3 is a graph showing nicotine content in mid-leaf of NtAAT2-S/T RNAi T0 plants (E324) and the respective control plants (CTE324).
Figure 4:
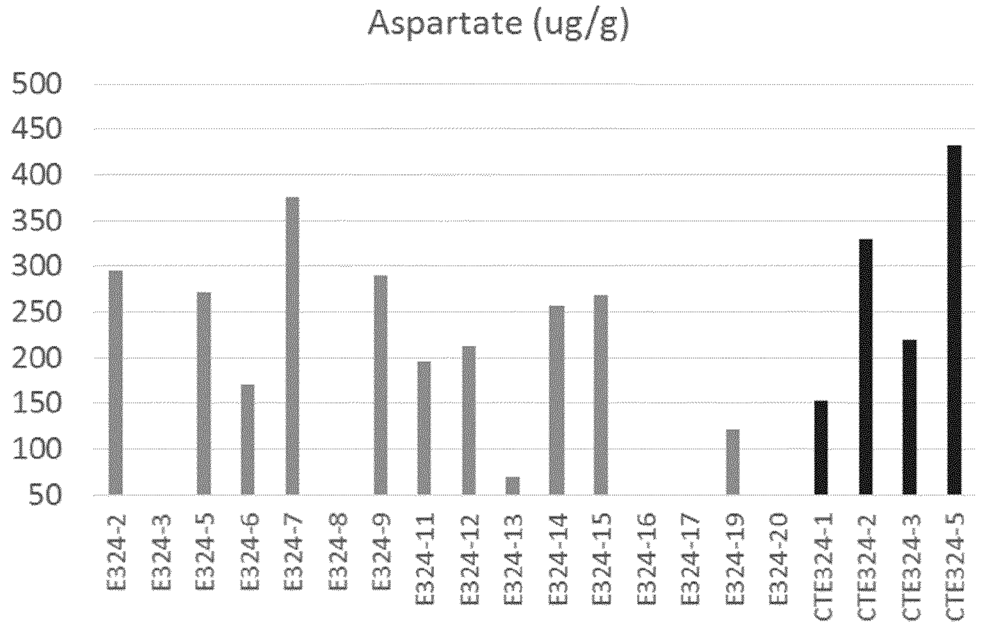
FIG. 4 is a graph showing asparagine content in mid-leaf of NtAAT2-S/T RNAi T0 plants (E324) and the respective control plants (CTE324).

To enable the selection of low aspartate plants, 16 independent T0 plant leaves (E324) and 4 respective control lines (CTE324) are analyzed after 60 h curing to determine the impact on nicotine, as control (see FIG. 3), and aspartate (see FIG. 4). There is no significant difference in nicotine content between the T0 plant leaves (E324) and the control lines (CTE324). The best T0 lines displaying the lowest level of aspartate are 3, 8, 13, 16, 17, and 20, in which the amount of aspartate is either detected at very low levels (75 ug/g) or not detectable. Seeds are harvested from these best T0 lines displaying the lowest level of aspartate. T1 progeny are assayed by qPCR to determine the efficiency of the NtAAT2-S and NtAAT2-T silencing events in relation to both aspartate and asparagine content.

As aspartate is in a key pathway for the synthesis of other amino acids like asparagine, threonine, isoleucine, cysteine and methionine, manipulating NtAAT genes (for example, with either a constitutive promotor or a specific senescence promotor—such as SAG12 or E4) may change the chemistry of tobacco cured leaves. Similarly knocking-out NtAAT genes using a gene editing strategy—such as CRISPR-Cas or mutant selection may change amino acid leaf chemistry as well as smoke and aerosol chemistry of the main varieties of commercial tobacco.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

NtAAT expression (FPKM) during early curing in Burley (BU), Virginia (FC) and Oriental (OR) tobacco

| | BU | | | FC | | | OR | | |
|---|---|---|---|---|---|---|---|---|---|
| | Green | Ripe | 48 h curing | Green | Ripe | 48 h curing | Green | Ripe | 48 h curing |
| NtAAT1-S | 7.8 | 6.7 | 9.2 | 11.4 | 8.1 | 15.8 | 12.9 | 12.9 | 13.0 |
| NtAAT1-T | 10.5 | 13.4 | 28.5 | 11.0 | 5.5 | 28.1 | 12.4 | 10.0 | 38.9 |
| NtAAT2-S | 9.8 | 21.9 | 234.1 | 1.9 | 6.0 | 65.1 | 18.5 | 49.3 | 665.6 |
| NtAAT2-T | 2.7 | 9.4 | 105.8 | 1.1 | 2.3 | 12.0 | 5.1 | 11.7 | 80.4 |
| NtAAT3-S | 14.5 | 10.7 | 17.7 | 21.2 | 13.2 | 11.1 | 24.5 | 18.1 | 22.6 |
| NtAAT3-T | 14.7 | 13.0 | 21.0 | 18.2 | 16.6 | 9.7 | 29.4 | 29.0 | 22.7 |
| NtAAT4-S | 44.5 | 39.8 | 29.0 | 45.6 | 41.7 | 28.9 | 6.4 | 7.0 | 3.2 |
| NtAAT4-T | 60.7 | 47.0 | 21.6 | 57.3 | 55.9 | 19.2 | 44.9 | 47.3 | 25.8 |

TABLE 2

Expression of NtAAT genes in leaf, petal and root of Burley (BU) and Virginia (FC) plants grown in the field

| | Leaf | | Petal | | Root | |
|---|---|---|---|---|---|---|
| | BU | FC | BU | FC | BU | FC |
| NtAAT1-S | 5.2 | 9.8 | 17.3 | 27.6 | 15.0 | 11.1 |
| NtAAT1-T | 6.6 | 6.9 | 52.4 | 33.5 | 3.8 | 4.2 |

TABLE 2-continued

Expression of NtAAT genes in leaf, petal and root of Burley (BU) and Virginia (FC) plants grown in the field

| | Leaf | | Petal | | Root | |
|---|---|---|---|---|---|---|
| | BU | FC | BU | FC | BU | FC |
| NtAAT2-S | 7.6 | 4.1 | 152.7 | 213.0 | 7.1 | 6.1 |
| NtAAT2-T | 2.1 | 1.0 | 68.2 | 128.7 | 3.4 | 4.5 |
| NtAAT3-S | 20.5 | 19.5 | 25.4 | 26.0 | 30.9 | 18.9 |
| NtAAT3-T | 20.9 | 19.9 | 37.4 | 36.9 | 31.3 | 24.4 |
| NtAAT4-S | 69.0 | 44.8 | 42.3 | 49.8 | 29.1 | 24.9 |
| NtAAT4-T | 81.5 | 49.1 | 43.2 | 46.9 | 18.2 | 18.8 |

SEQUENCE LISTING

SEQ ID NO: 1: Nucleotide sequence of NtAAT2-S

```
atgaacatgtcacaacaatcaccgtcaccgtccgctgaccggaggttgagtgttctggcgagacaccttgaactgtc
gtcctccgccaccgtcgaatcctctatcgtcgctgctcctacctctggaaatgctggaaccaactctgtcttctctc
acatcgttcgcgctcccgaagatcctattctcggcgtaactctctctctctctctctctctctctcttcatccacac
acacacgcactcactcacataacatattaagtatatgcgtgctcaaatgttctgtatgtattcatttgttccgtatc
aaatgttctcttgttataagctgaattttagaggaattgtagtgctatttgctaatcgaaagagcttgatactcatt
ctcttcctattgaattaaatattcctttttttcttatggatgatgaatttaagactttttttttagtccgatcactacg
aaatttcgatttcaagttgatagaagtgaaaaatgatggggttaacatatcaattgagcgaataaaaagagaaattc
gtgtgttgatatcttcaaaagtgtatttaaatgtagagatatattgtgatttagtttctgttattatctttgtcttt
tttctattgaaatttgaatattatttgttgaagtcttcgtgacatatcttggtgttatgttttggttattaggtcac
tattgcttacaataaagatagtagccccatgaagttgaatttgggagttggtgcatatcgcacagaggtgatcatcc
tttttggattttgtatttgcgctattatggtcaatggagcactattatcagttgctggataatcatcctttttgata
tttccttgattgaaatctaaaaacacgaataaaaagatatttactgatggatctgtgttttggtttcttcagattga
cgcatttctgttaattgaaaagaattgtgattgttttggtgattgtggtgttattttagcttcatacagttaatccg
acgccgtagtgtactagtgtttggctgatgtgctgccaagagataatgtttaagattatggtttgccataattgata
aaatttaatattaaaagtacttggctggatgttctgcgtttgcataacttgtaatgcatatgaaaaagttacctttg
attttcataattagtgagaaaactcaagtagcttccgcattcctgtcattgcactatcaaacacattaaacggtttc
cgacatatctacctagtttggaacttcatgatttctatttttcacaccttgtaataaatgataattcttggatctgt
ggtgtctttgttcaaaagatcacagagaagattgcatttatttttttgtagtctagttggctcagagtctgtcaaaca
caacttgttacatcgcattttacctgttagttaagaaacttgggtcatcaacaaatttgtcatgaggtggttatttc
ttggggctttgtgaattgctctcagcaatctgctagctttcttatgtggactcaaaacaatgaagctcttgagttga
tgtgttgatttttcaatcagagtaaaacaagttctatatttggctgtgagagtaaagtgggagctattaaaattcct
agctgaatttatgtttcttaatatcttaaatccttaaaggtagagggagaggaaggaggtttattgatgaagggcta
gtagttgtgtatacttagttctttttcaaatttcataagtatctcttgatggtttttctcgctgactgttgaatatg
gggctccacagtttgtgttgctatattgaaatgtttcagctaataaaactaacgtgtttctttttctttctcccttt
tttggggttatcaggaaggaaaacctcttgttttgaatgttgtaagacaagcagagcagctactagtaaatgacagg
tacttgcattgccatttcatggagtatgaataaaatgtttccttaattctatgtgattaaacttcaagatttctgca
ggtctcgcgttaaagagtacctatctattacgggactggcagacttcaataaattgagtgctaagctgatacttggc
gccgacaggtataaaagttcctgttctctgtatagtgttgccgataagatatgcagggagataaagcatgtattttc
ctgttgcataggatgatatcttcagataataaggctccattccaagtgtttgatggcttggtagatctttgtgaagc
atctattaacatttggtcacatttttttaaaaccaacttcccatcccatccatgccattccacgtgtcagttattca
tgaaaatgctgttcacttgcatacatgttactgccgttgtgttgatttcctcaactctactcataatttctctgtgt
ggtcgcattctggtgatctgatttatctgataatatctgtacatgttttgaaatttgggtagtgtctctttgattag
```

-continued cgtgtaaagcaagcaactcttgatgcgtgtgatcaagtgtattgctgtctagagctgacagatgttaaatttatctt atgcgtttccaagatcttccagatgttctatgtaatctttttaggccagcttaaactttgacttgcttcatatacat ttatgttaaaggagagttgttaatatacttcaatttttcacatttttaattcctctttttacctgtggtcctcacga gctcttactttctttgcttggtacagccccgctattcaagagaacagagtaacaactgtgcagtgcttgtctggcac aggctcattgagggttggagctgaatttttggctcgacattatcatcaagtaaactgctacatcttcctaacctacc tttcattttccttcgttttcttagccttcgtgggtaaacaatcttcaaagttgaattaaccttgatgtaaccattcc tgcagcgcacaatttatattccccaaccaacatggggaaaccacccaaaagttttcactttagctggattatcggta aagagttaccgctactatgatccagcaactcgtggactcaattttcaaggtatgaaacacttccctacaatataatg atgtaacaggatattgtcccattagatatctatggctatgctgtttactattactctcttccaggatgatggatgtt cttttagtcttattctggtatttgattacaaattatcacaagtctgaatcaagttgtggatggatggtttcacttgt ttgattgcattgtaatccagcaaacttgtaaagtcatcgtcatctatgctttttctttataccttttttctgcgagga aataagcgaagagagatggagatataacttgataataatggaatgcaacaaacgcctaatttaacatattagggacc aactaacgtctacatttgacattagctcttaacattttgactttttaataccttaccaaaaataaaaaagattgaca ttctaatgtcgcacggaaccaaaggtgggaatagctgataacatagaaaagtaaccaaacaagtcctggaatcttgt caaaaaagaaattcagttgtcgaaatgttcttgaaaaaagttactgcaaccgcaatggtcggaagaataggaggaag aaattcaataatgcgggtcaaatagaggaggtgccactaaaaggccattggagaggggccgggaaacaccatctgaa agaggtacagtggtaccagaaggattatcgaatgctgatgcatagaaacgagtcagagattgaaacagtcactggaa agaggtttgatgttgtgacagcagtcacaataaagaaaagtggtgcaatcagaatgatcactggaaaggctagaatt gtagaactatcataagaaagtgaattgtggagggaaatctctgtgaaaagacaaaatctatttaggtccacaagatc atagaggctctaatgccatgtgagaaactgagagagtggacggaaataaatagattacttgataaaatacaatccat acgtttaaatccgaatgactaactttaattttaacacaacttttacatctaaaagtatgacacgtgacattctaacc tttcgtgcttgtgttcacaactttgcatatcgccgacttgtttacaagaactttctttttcgtacatgacaggtttg ttggaagaccttggatctgctccatcgggagcggtagtgctacttcacgcttgtgcccataaccccactggtgttga tccaaccattgatcagtgggagcaaattaggagattgatgagatcaagaggattgttgcccttctttgatagtgcat atcaggtaagagatcatcaacagatgtgcagagcactttggctgttggagttgttgctgtgtgagcatttaaaagtg atgtggtttgttcagtatatgtcaattaaccttgatattcaaactttgatattctagggctttgccagtggaagcct agatacagatgcacagtctgttcgcatgtttgtggcagatggaggtgaagtacttgttgctcaaagttatgcaaaga atatggggctttatggtgaacgtgttggagctctaagcattgtacgtcttaaaggacaatggacaactgtgccttat ttctgaaaatttatatctccagttggtcatttgttgcattacctttatttttctcagattgattctcatgatgcata aactgtcttactgttttcatagtggccttcttttgtgatgttaaaatttggtagttatgaactgtttaaagcttata tagcttacttccaaataaataactgtgagccttggacatcacatataaattattttatatcacggattcgagccgtg gaaacaacctcttgcagaaatgtagggtaaggttgcgtataatagacccttgtcatccggcccttccccggacccct gcgcatagcgggagcttagtgcaacgggttgcctttttttcatcctgaggcataaaaagtttgtaatttctcaagaa tgaataaagagcctgttataacaggcaatttgcatatcatatggtgttgtttgtcgcacagtgatgacatatttatc acacaaatgaaagaaaaatgaaggatatagttctgaaccctcagttaaactctgctgacagttataattcttcaaat tttctcaaatctgtaggtctgcaggaatgctgatgtggcgagcagagttgagagccagctgaagttggtgattaggc caatgtattccaatccgcccatccatggtgcgtcaatagttgccacaatccttaaagacaggtaatatatcaaccat caggaaattgcttcttgggaccctaaaaagccatttcctttctttctatatgatagaatccagtgtatgttcaaaaa ttatgtttagtcattgttctgcaaaataaatcactaattttctgcagaaacatgtaccgtgaatggacccttgagct gaaagcaatggctgatagaatcatcagaatgcgtcagcaattatttgatgctttacgtgctagaggtaaatttgctg -continued cattattttcacgtatgtgtgctcttattacatgtttcttgttgcatcgacttcggatatttttctcatttttgata atttcggttcaagtgtcattataaatgctacatgttcgtggcatatacttctacccataaaatatgctgcaacttgt tccagctcatttgtctagataatttatcaaaaggaccaatcttcaccagctgactctcctgaatgaaagcttaattt aggaaaaagattaagcaaacaaaacatggaattcgacaaattcaaacatttctccaaatcttaatagatctcgatcc tccttagtgctttcatcaacttcttaggtaattcacctcttaactttggctctgactgggttctctacctttggaaa accatccccaaagatgtcccttgcacgatccttttggggacatgaactgttggatcaggcaagaaactatcccccaa taaagaaaaattgttggatcagatttttttcctgataggttgcattctttcagcattccccttaaagtttgtgatttg gacgttgtcctcattttggtataaaaaatgtcattggaaactttccattttggcacatcaggtgttagaatcatcat gtcttcataaattggctatagacaaagtctcatgtcgtcagctcctttcttcagtatcaggcattctttaatcaatg taagtgtcgagcattgcatgagtaggatacttatttctatttacatgaattgatgggcaagtcgggcatttttttagt cgacttaaaggtcaagcattgcatgtataagatatctatttctgttgaattcaattgattggcaggtacacctggtg actggagtcacattatcaagcagattggaatgtttactttcacgggacttaactcagagcaagttgccttcatgacc aaagagtaccacatctacatgacatcagatgggtaatatgtcatttctcagcaaaaagtactgtatatcatatcaga ctaccatgtctcctccacatctgatatgtgattttattacctcgtaagaatttctaccctcggatggtaaaacagaa agagggaagggagttaaaatcttttcagccatcagttagttcttttcttgcagtattcttgctaccttagctttgat gaacgctaagagaaatgtggctgtattaatgaacatttctagagcatggttctttctaagtttgtatttaattgtgg caacttcaattaagcttgggatatcagataatcccaaagcctttgacatacatcacatatttcattttgcagacgca tcagtatggcaggtctgagctccaggacagttccacatctagcagatgccatacatgctgctgtcgctcgggctcgt tga SEQ ID NO: 2:
Deduced polypeptide sequence of NtAAT2-S as set forth in SEQ ID NO: 1
MNMSQQSPSPSADRRLSVLARHLELSSSATVESSIVAAPTSGNAGTNSVFSHIVRAPEDPILGVTIAYNKDSSPMKL

NLGVGAYRTEEGKPLVLNVVRQAEQLLVNDRSRVKEYLSITGLADFNKLSAKLILGADSPAIQENRVTTVQCLSGTG

SLRVGAEFLARHYHQRTIYIPQPTWGNHPKVFTLAGLSVKSYRYYDPATRGLNFQGLLEDLGSAPSGAVVLLHACAH

NPTGVDPTIDQWEQIRRLMRSRGLLPFFDSAYQGFASGSLDTDAQSVRMFVADGGEVLVAQSYAKNMGLYGERVGAL

SIVCRNADVASRVESQLKLVIRPMYSNPPIHGASIVATILKDRNMYREWTLELKAMADRIIRMRQQLFDALRARGTP

GDWSHIIKQIGMFTFTGLNSEQVAFMTKEYHIYMTSDGRISMAGLSSRTVPHLADAIHAAVARAR

SEQ ID NO: 3: Nucleotide sequence of NtAAT2-T
atgaacatgtcacaacaatcaccgtccgctgaccggaggttgagtgttttggcgaggcaccttgaaccgtcgtcctc cgccaccgtcgaaacctccatcgtcgctgctcctacctctggaaatgctggaaccaactctgtcttctctcacatcg ttcgtgctcccgaagatcctattctcggggtaactttctctctctctctctctctctcttcatccacacgcactc actcacataacatatgtataagtatttaagtatatgcgtgctcaaatgttctgtatatattcatttgttccgtatca aatgttctcttgttataagctgaattttagaggaattgtagtgttatttgctaatcgcaagagcttgcatactcatt ctcttcgtattgaattaaatattcctttttttcttatggatgacgaatttaagcagtttttttgagtccgatcactacg aaatttcgatttcaagttgatagaagtgaaaaatgatggtgtttacatattaattgagcgaataaaaagagaaattc gagtgttgatatcttcaaaaatgttgttaaatgtagagatatactgtgatttagtttctgttataatctttgccttt tttcttttgaaatttgaatattgtttgttgaagtcttcgtgacatattggtgttatgttttggttattaggttacta ttgcatacaataaagatagcagccccatgaagttgaatttgggagttggtgcatatcgcacagaggtgatcatcctt tttggcttttgtatttgcgctattatcgtcgatggagcactattatcagtagctggataatcatcctttttgatatt tccttgattgaaatccaaaaacacgaataaaaagaaatttactgatggatctgtgttttggtttcttcagatttacg catttctgttaattgaaaaaatattatgattgtcttggtgattgtggtgttgttttggcttcatatagttaatccga cgccgtagtgtactaatgtttggctgatgtgctgccaagagaaatgtttaagattatggtctgccataactgataaa -continued

```
atttaatattaaaagtacttggctggatgttctgcgtttgcataacttgtaacgcatatgaaaaaattacctttgat
tttcataattagtgagaaaattaagtagcttccgcattcctgtcattgcactatcaaacacatacggtttatgatat
atctacctagtttggaactttgtgatttctatttttcacaccttgtaataaatgataattcttggatctgtggtgtc
tttgttcaaaagatcacagagaagattgcacttatgttttgtagtctagttggctcagactctgtcaaacacaactt
gttacatcgcatttacctgttagttaagaaacttgggtcatcaacaaatttgtcatgaggtggttatttcttgggg
ttttgtgaattgctctcagcaatctgctagctttcttatgtggactcaaaacaatgaatctcttgagttgatgtgtt
gatttttcaatcgagtaaaacaagttctatatttggctgtgagagtaaagtgggagctattaaaattcctagctgaa
tttatgtttcttaatatcttaaatccttaaaggtagagggagaggaaggaggcttattgatgaaggactagtagttg
tgtatacttagttctttctcaaatttcataagaatctcttgagggtttttctcgctgactgttgaatatggggctcc
acagtttgtgttgctatattgaaatgtttcagctaataatactaacgtgtttctttttctttctcccttttgtgggg
ttatcaggaaggaaaaccgcttgttttgaatgttgtaagacaagcagagcagctactagtaaatgacaggtacttgt
gttgccatttcatggagtatgaataaaatgtttccttaattctatgtgattaaacttcaagatttctgcaggtctcg
cgttaaagagtacctatctattactggactggcagacttcaataaattgagtgctaagctgatacttggtgccgaca
ggtatacaagttcctgttctctgtatagtgttgctgataagatatgcagggagataaagcatgtattttcctgttgc
ataggatgatatcttccgataataaggctccgttccaagtgtttgatggcttggtagatctttgtgaagcatctatt
aacatttgctcacgtttttttaaaaccaacttcccatcccatccatgccattccacgtgtcagttattcatgaaaat
gctgttcacttgcatacatgttactgccgtagtgttggtttctctcaactctactcataatttctgtgtggtcgcat
tctggtgatctgatttatgtgataatatctgtacatgttgttttgaaatttgggtagtgtctctttgattagcgtgt
aaagcaggcaactcttgatgcatgtggtgaagtgtatgattgctgtctagagctgtcagatgttaaatttatcttat
gcgtttgcaagatcttccagatgttctatgtaatctttttaggccagcttaaactttgacttgcttcatatacattt
atgttaaaggagagttgttaatatacttcaattttcacattttaattcctcttttacctgtggtccttacgagctc
ttactttctttgcttggtacagccctgctattcaagagaacagagtaacaactgtgcagtgcttgtctggcacaggc
tcattgagggttggagctgaatttttggctcgacattatcatcaagtaaactgctacgtcttcttaacctacctttc
actctccttcgttttcttagccttcgtgggtaaacaatcttcaaagttgaattgaccttgatgtaaccattcctgca
gcgcactatttatattccccaaccaacatggggaaaccacccaaaagttttcactttagctgggttatcagtaaaga
gttaccgctactatgatccagcaactcgtggactcaattttcaaggtatgaaacacttcccttcaatataatgatgt
aacgggatattgtcccattagatatctatggccatgctgtttcctattactctcttccaggatgatggatgttcttt
tagtcttattctggtatttgattacaaattatcacaagtctgaatcaagttgtggatagatggtttcacttgattga
ttgcattgtaatccagcaaacttgtaaatccgtcatcatctatgctttttctttataccttttttctgcgaggaaat
aagagcagagagatggagatataacttgataataatggaatgcaacaaacgcctaatttaacatattagggaccaac
taacatcagcatttgacattagctcttaacattttgactttttaacaccttatcaaaaaaaagaaggaaaaagattg
acattctaatgtcgcacggaaccaaaggtgggaatagctgataacatagaaaagtaaccaaacaagtcctggaatct
tgtcaaaaaaaaattcagttgccaaaatgttcttggaaaaaattactgcaaccacaatggtcggaagaataggagga
agaaattcaataatgcgggtcaaatagaggaggtgccactaaaaggccattggagaggggccgggaaacaccatctg
aaagaggcacagtggtaccagaaggattatcgaatgctgatgcatagaaacgagtcagagattgaaacagtcactgg
aaagaaggcttgatgttgtgacagcagtcagtcagaataaagagaagtggtgccatcagaatggtcactggaaaggc
tcgaattgtagaactatcataagaaagtgaattgtggctgggagactctttgaaagacaaaatctatttaggtctcc
acaagatcatggatgctctaatgctatgtgagaaactaagagagtggacgaaaataaatggattacttgataaaata
caatccatacgtttaaatccgaatgactaactttaattttaacacaacttttacatctaaaagtatgacacgtgaca
cttaacctttcatgcttgtgttcacaacttcgcatgtcgccgacttgtttacaagaactttatttttcatacatgac
aggtttgttggaagaccttggatctgctccatcgggagcgatagtgctacttcatgcttgtgcccataaccccactg
```

-continued gtgttgatccaaccattgatcagtgggagcaaattaggagattgatgagatcaagaggattgttgcccttctttgat agtgcatatcaggtaagaaatcatcaacagatgttcagagcactttggctgttggagttgttgctgtatgagcattt aaaagtgaggcggtttattcagtatatgtcaattaaccttgatattcaaactttgatattctagggctttgccagtg gaagcctagatacagatgcacagtctgttcgcatgtttgtcgcagatggaggtgaagtacttgttgctcaaagttat gcaaagaatatggggctttatggtgaacgtgtcggagctctaagcatcgtatgtctcaaaggacaaaggacaactgt gccttgtttctgaaaatttatatctccagttgttcatttgttgcattacctttatttttctcagattgattctcatg atgcatgaactgtcttactgttttcatagtgttcttttgtgatcttaaaatttggtagttatgaactgttaaagctt atatagcttacttccaaatatataactgtgagccttggacatcacatataaattattttatatcacggggtcgagat gtggaaacaacctcttgcagaaatgtagggtaaggttgcgtacaatagacccttgtggtccggcccttcctcggacc cctgcacatagcgggagcttagtgcactgggttgcccttgttttcatcctgaggcataaaaagtttttaatttctca agaatgaataaagagcctgttataacaggcactttgcatgtcatatggtgttgtttgtcacacagttatgcatatag tgtagtttatcacacaaatgaaaaaaattgaaggatatagttctgaaccctcagttaaactctgctgacagatataa ttcttcaaaattttctcgaatctgtaggtctgcagaaatgctgatgtggcgagcagagttgagagccagctgaagtt ggtgattaggccaatgtattccaatccgcccatccatggtgcgtcaatagttgccacaatccttaaagacaggtaat atatcaaccatcaggaaattgcttcttgggaccccaaaaaagccatttcctttctttctatatgatagaatccagtg tatgatcaaaaattatgtttagtcattgttctgcaaaataaatcactaaatttctgcagaaacatgtaccatgaatg gacccttgagctgaaagcaatggctgatagaatcatcagaatgcgtcagcaattatttgatgctttacgtgctagag gtaaatttgctgcattattttcacgtatgcgtgctcttattacatgtttcttgctgcatcgacttcggatatttttc tcatttttgataatttcggttcaagtgtcattataaatgctacatgttcgtggcgtatacttctacatataaaatat gctgcaactcgttccagctcatttgtctagataattgatgaaaaggaccaatcttcacagctgactctcctgaatga aagcttaacgaaggaaaaagattaagcaaacaaaacatggaattcgacaaattcaaacatttctccaaatcttaata catctcgatccttcttagtgctttcatcaacttcttaggtaattcacctcttaactttggctctgactggattctct acctttggaaaaccatccccaaagatgtcccttgcacgatccttttggggacatgaactgttggatcaggcaagaaa ctatcccccaataaagaaaaattgttggatcagatttttcctgataggttgcattctttcagcattccccttaaag tttgtgatttggacgttgtcctcattgtgttacaaaaaaatgtcattggaaacttccattttggcacatcaggtgtt agaatcatcatgtcttcataaattggcaatagacaaagtctcatgtcgtcaactcctttcttcagtgtcaggcattc tttaatcaatgcaagtgtcgagcattgcatgaataggatacctattactatttacatgaattgatgggcaagtcggg catttttttagtcggcttaaaggtcaagcattgcatgaacaagatatctatttctattgacttcaattgattggcagg tacacctggtgactggagtcacattatcaagcagattggaatgtttactttcacgggacttaactcagagcaagttg ccttcatgaccaaagagtaccacatctacatgacatcagatgggtaatgtgtcatttcttagcacaaagttctgtat atgtcatatcagactaccatgtccccccctacatctgatatgtgattttattacctcgtaagctcggatggtaaaaca gaaagagggaagggatttaaaatcttatcagccgtcagtttgttcttttcttgtagtattcttgctaccttagcttt gatgttcgctaagagaaatgtggcggtactaatgaacatttctagagcatggttctttctaagtttgtatttaattg tggcaacttcaattaagcttaggatatcagataatccaaagcctttgacatacatcacatatttcattttgcagacg catcagtatggcaggtctgagctccaggacagttccacatctagcagatgccatacatgctgctgttgctcgagctc gttga SEQ ID NO: 4:
Deduced polypeptide sequence of NtAAT2-T as set forth in SEQ ID NO: 3
MNMSQQSPSADRRLSVLARHLEPSSSATVETSIVAAPTSGNAGTNSVFSHIVRAPEDPILGVTIAYNKDSSPMKLNL

GVGAYRTEEGKPLVLNVVRQAEQLLVNDRSRVKEYLSITGLADFNKLSAKLILGADSPAIQENRVTTVQCLSGTGSL

RVGAEFLARHYHQRTIYIPQPTWGNHPKVFTLAGLSVKSYRYYDPATRGLNFQGLLEDLGSAPSGAIVLLHACAHNP

-continued

TGVDPTIDQWEQIRRLMRSRGLLPEEDSAYQGFASGSLDTDAQSVRMFVADGGEVLVAQSYAKNMGLYGERVGALSI

VCRNADVASRVESQLKLVIRPMYSNPPIHGASIVATILKDRNMYHEWTLELKAMADRIIRMRQQLFDALRARGTPGD

WSHIIKQIGMFTFTGLNSEQVAFMTKEYHIYMTSDGRISMAGLSSRTVPHLADAIHAAVARAR

SEQ ID NO: 5: Nucleotide sequence of NtAAT1-S atggcgatccgagccgcgatttccggtcgtcccctcaagtttagctcgtcggtcggagcgcgatctttgtcgtcgtt gtggcgaaacgtcgagccggctcctaaagatcctatcctcggcgttaccgaagctttcctcgccgatcctactcctc ataaagtcaatgttggtgttgtaagtttttttttctctttgctttgtttgattttccacttcatttcgtgtaagcta ggatttagcttacttgaccatttcgctattcttcataggccatagctgtaaaaatggttttactgtgacgaatcttc gacgatctcaatcgctttgggattgggagagagtttattgatttaatttttgtatgcattccactttttcaacttg atctatttaagaaaaaaattgaaaaagatttgacctttttttcttaaattatttcttttaaatttttttatttttgtga ttattatatagggagcttacagagacaacaatggaaaacccgtggtactggagtgtgttagagaagcagagcggagg atcgctggcagtttcaacatgtgagtgctctcctgatttattcaagtttttctgttattttatttgtaattaattac gattacgttaactttgatctattagaaaatagaaacttcagccagtaagattactttttttcttcgaggagtgtgag atgtaaacccaggtcggatgcactggaattcttcactagtttgtgcaaatatattcttaatatttttcaaaaacttc ctgtgtacacacacacatacatgtaattaattaagtaattacctactgatctaggatttttaggtagttcggaaaaa tatattttcaatatcgtttaagaattttctgggtatgcgtagtttgagtatgataaaatgggtgcatgtgcaccact gcttacgctagggaacagcctctaattagctgttggtgagtctggtgagtggtgactgttctttattttcagttact tcgcacattgttggtttttgattaagtataaataaacgaatgttttagtgagtgcttatttctatgaagcatctttt ttaggtctacagaaatgggtggtacgatattttccagccgtcagctccactaaccagtttgattctttgggactttt tctttgtattctcacgtttacttctagtggatggtgcagatggatttctttactaattctttcttctgcgtttgcag agctttctcccaagataaattattaatatcaaattgacctttcgatagttcaatggtgtttaactttttcaaatatt gcccattttatattatgaagtttgaaagtttaactagacatgttgtaataaattttatttgacttgtgtattttatt cattgtggttggagaaagtattaaaataacaagtgaaaagtctgttttacgtcaagtttgaatttgaatttttgaat tgatttgcttctttaagtttatgaaaccatctatgagaatattattggcactccattgtctcattttatgtgaaggc atttgacgttgcacaaaatttaaaaatataaagaaacttatgacgtgtaagttagatatatgcagagtaccatagtt atccttttaagtaagtgatagtgagagtttcacatttctttttgttctctcttcttataaaagaatgaatttttgta tcccaacaagtcatatcattaatgttaacacggggatactaagattaactaatgtctaaaaagagaaagatttcatt cttcttggacgggctaaaaaggaaagtatgtcacataaaatgagacagagatatgttaggatttgtcctgaatttct aatcaattaggactctctttcttgaaggaatggaaaaagactcctaaaaggattaaatctccttaatatgtcttatc cttttcttggaagacaagttttgcacatctataaattaaggatctctgcttttcacaagaacacaaaaaaaaaatat ccacaatgtagttattaaagagtttgtttagggggagatttttctctcgatagtttttcttcttttatattagtttt atcatatgtagatcaattgaccaaatcattataaactattatgcttagtttaatatatttttcttttgttgtctgat ttatcgtccatcaagttttgtattgttagttttcgcatgcaccatgttatttcgaacccaacaagtggtatcagagc caatggttcagagtcaacggttgaacgaggttgaagaaagattcaatgcgtgtttagatcaagacgataatgaagat ttattcaacatgctacatgtggagataaatttacaattacaattgtattcaacacgcctgctgttgcatctttattg gaataaaaactctttctaacccatattttggccactttaaaccaatgccaattttaagtcatgcctacttgcaacac atgagttccagtgccagttttaactcacgcttctttttaatgcatgagcttcttttatcccatgtttattcttaaca cgcgggctccttttaacccatacttggtttttttttaaccaataccaagattttcaatttttaatcatggcaagcag cagtgatgaagattatgtgaagaaggtgaatcaactttgtcaagaaaattcaggccaaggggagattgttaggattt gtcctgaatttctaatcaattaggactctctttcttgaaggaatggaaaaagactcctaaaaggattaaatctcttt actatgtcttatcattttcttggaagacaagttttgcacatctataaattaaggatctctgcttctcacaagagcac -continued aaaaaaaaaaatatccacaatgtagttattaaagagttttgtttaggggagatttttctttcaatagtttttcttc ttttatattagttttatcatatgcagatcaattgaccaaactattatgcttagtttaatatttttttttttttgtcgt ctgatttatcgtccaccaagttttgtattgttagtttccgcatgcaccatgttatttcgaaccctcgtataagtttg tcaaacattttgtgacttcctaaactagaaagtgtcttgggatgggggagaactacgctatctgatctcaaaaaaag tgtgcatcatgtgatactatgtggatagtttagttcacatgttgacaattcatcatttatcagggaatatcttccta tgggaggtagtgtcaacatgatcgaggagtcactgaagttagcctatggggagaactcagacttgataaaagataag cgcattgcagcaattcaagctttatccgggactggagcatgccgaatttttgcagacttccaaaggcgcttttgtcc tgattcacagatttatattcctgttcctacatggtctaagtaagtgtattcttctgcttctcggcatctctacagca tcctaattgatcttcctcaattggtttttgcactttaaaacatgagtatgcaaataccttcaaaattttctaatttc ctgtcattactaatataaagttcttggcagtcatcataacatttggagagatgctcatgtccctcagaaaatgtatc attattatcatcctgaaacaaaggggttggacttcgctgcactgatggatgatataaaggtaagaaaacatatattt gaggttgtttgccatgatggttggttctcctgtttgatgatatagtgtccctcctcaagtggcaattatgtgttcta tcctgacgtatttcaattttcattgacatagaatgccccaaatggatcattctttctgcttcatgcttgcgctcaca atcctactggggtggatcctacagaggaacaatggagggagatctcacaccagttcaaggtaatgatttgtatgttt tgtctctcccttttcttgtcataagtcatattaaatttattacactggttccaggtgaagggacattttgctttctt tgacatggcctatcaaggatttgctagtgggaatccagagaaggatgctaaggctatcaggatatttcttgaagatg gtcatccgataggatgtgcccaatcatatgcaaaaaatatgggactatatggccagagagttggttgcctaaggtaa actactactcccaccatcatatcttatttgccctagttacaatctggagagtcaaacaaactttttattagaccata gttggtctatttttcaaatgatctaattccaaaagcagttactactatttcatgcaaattctagattaattaacctt ttgctatacctcattatcttcatttagtaggcagtagctaattttaccatatatcatatttttcatataatcaatat gtagagttatttatttatttatatattttaaatttatttaggataaattttgttctttccggtaatttcagttcatt tccacctaaaagtccaactcgaagagaaaaacagaattttgctagtcaaaacttagatccaatgaaaagcaccaaaa ttttggttttaaattataaaacatgtctactctaggtttttttcctaggcaagcgatgtgattttacaatcttacaa taaggcatcaatcaatcccaaactagtttggttcaacaatataaatctttgttcctatttcatggcattgggcccat tgcattccaataatggtaaataagacaaattagaggttatctaagattagagattccttattaaaatctcatactta tatctacattgtcacgcaagtctctgaccttaaaagaagacttctagcagacaccagacttaacgtaagtgtaacaa caacaactaagttttaatccaaactagttagtatcgcttatatgaatcccttgcttccattgtgtagcactaaacaa caacaacaacataccgagtataatctcacatagtggggtctggggagggtagtgtgtacgcagactttacccctgcc ttgtggagaaagagaggctatttccaatagaccctcggctcaaaaccattgtgtagcaatggaggcatgaaatagaa aacttgtcttctgattaaaatctgttattaaattaatgaggagaaaaaattggattacttgttggtaaatcttattt gttgttttaaacacacacaaagccgaaagacctctgatacttttcctgagatgcttccgcaattcactgcagtgtgg tttgtgaggatgaaaaacaagcagtggcagtgaaaagtcagttgcagcagcttgctaggcccatgtatagtaatcca cctgttcatggcgcgctcgttgtttctaccatccttggagatccaaacttgaaaaagctatggcttggggaagtgaa ggtaatatggttagaacaagaaaagatttatgattatataactatcattggtattttgacaaaaggtaggaactagg aaccttgctattaaagatattttcttccctttattttggaaaaaaaggtattttcttgctttcttcaaatgtttgag atttggatagagccgttacatggaaatgctgtgcaattttctgctactcacatggaaaagatctttttcttttgctg atctgtttaagcacctatttgctaaagcctactatgtcagtatgttgttcaatcttttcagccacagaaacaggtct aaaccagttccaaactttaaataatcttaccatggtagtttcagcaaagataaattggtccgtgcagccattaactg ttttctttgtcgggcttcttaaacttgttttctccaaggtctagttgttggtgctgtggctgctttttagctttgtg ctcattatcagagcatcatatgtttaagtgtaaaggttcaatgactaagttctttttccagggcatggctgatcgca ttatcgggatgagaactgctttaagagaaaaccttgagaagttggggtcacctctatcctgggagcacataaccaat -continued caggtattgaaatcaacaacttctgttgttttctatgctactagtatataactattaagaaaattactgtggttcac ctactgcgccattaatactcgataccaccaacagattggcatgttctgttatagtgggatgacacccgaacaagtcg accgtttgacaaaagagtatcacatctacatgactcgtaatggtcgtatcaggtataatcattaggtcaccaatttc tgcttaatgctccggtgttcttgtacagagttatatctcattatttttccactatgttgtgtgttttgtacgtgca gtatggcaggagttactactggaaatgttggttacttggcaaatgctattcatgaggccaccaaatcagcttaa SEQ ID NO: 6:
Deduced polypeptide sequence of NtAAT1-S as set forth in SEQ ID NO: 5
MAIRAAISGRPLKFSSSVGARSLSSLWRNVEPAPKDPILGVTEAFLADPTPHKVNVGVGAYRDNNGKPVVLECVREA

ERRIAGSFNMEYLPMGGSVNMIEESLKLAYGENSDLIKDKRIAAIQALSGTGACRIFADFQRRECPDSQIYIPVPTW

SNHHNIWRDAHVPQKMYHYYHPETKGLDFAALMDDIKNAPNGSFELLHACAHNPTGVDPTEEQWREISHQFKVKGHF

AFFDMAYQGFASGNPEKDAKAIRIFLEDGHPIGCAQSYAKNMGLYGQRVGCLSVVCEDEKQAVAVKSQLQQLARPMY

SNPPVHGALVVSTILGDPNLKKLWLGEVKGMADRIIGMRTALRENLEKLGSPLSWEHITNQIGMFCYSGMTPEQVDR

LTKEYHIYMTRNGRISMAGVTTGNVGYLANAIHEATKSA

SEQ ID NO: 7: Nucleotide sequence of NtAAT1-T
atggcgattcgagccgcgatttccggtcgttccctcaagcatattagctcgtcggtcggagcgcgatctttgtcgtc gttgtggcgaaacgtcgagccggctcctaaagatcctatccttggcgttaccgaagctttcctcgccgatcctactc cccataaagtcaatgttggcgttgtgagtttttttttcctctttgttttgcttcattttccacctcatttcgtgtat gcaaggatttagcttacttgaccatttcgctatacttcccttggtaggccatagctgtaaaaaatagttttactgtg acgaatcatcgacatatggatacagagtattctaatggagtagtcaacaacataagtcgatctcaatcgctttggga ttgagaaagagtttattgatttaatttttgtatgcgttccactttttttcaacttgatctatttaagaaaaaaaattga aaaagatttgacctttttttcttaaattatttcttttataaaatttgcttttgtgattattatacagggagcttacag ggacgacaacggaaaacccgtggtactggagtgtgtcagagaagcagagcggaggatcgctggcagtttcaacatgt gagtgcttctcctgatttattcatttttttctgttatttatttgtaattaattacgattacgttaaatttgatctat tagaaaatataaacttcagccagtaagattactttttttcttcgaggagtttgagatgtaaaacccaggtcggatgc actgggattcttaagtagtttgtacaaatatattcttaatagttttgtaaaatttgctgtatacacacacatgtaat taattacctactgatctaggatttataggtagttcggaaaaatatattttcaatatcgtttaagaatttcctgggtg tgtatagtttgagtatgagaaaatgggtgcatgtgcaccactgcttacgctagggatcagcttctaaatagctggtg gtgagtctggtgagtggtgactgttctttattttcagttactgtagccacaaattgttggttattgattaagtataa ataaacgaatgtattagtgagtgcttatttgtatgaagcatctttttttaagtctacagaaatgggtggtccgatatt ttccacccgtcagttcctctaactagtttgattctttgggactttttctttgtattctcacgtttacgcctagtgga tggtgcagatggatttctttactaattctttcttctgcgcttgcagagctttctcccaagataaattattaatatca aattgacctttcgatagttcaatggtgtttaactttttcaaatattgccccacatcccattttatattatgaagttt gaaaagtttaactagacatgttgtaataaatttttatttgagttgtgtattttattcattgtggtaggagaaactag aaagtattaaaataacaagtgaaaagtctgttttatggataaagaatattacgtcaagtttgaatttgaaattttga attgatttgcttctttaaatttatgaaaccatctatgagaatattattagcactccatttgtctcattttatgtgaa ggcatctgactttgcacaaagttaaaaaatataaagatacttacgacgtgaaagtttgatatatgccaagtaccata attatccttttaagcaagtgatagtgagagtttaacatttctttttgttctctcttcttataaaagaatgaattttg tatcaagtgggtcccaacaagtcattcattaagggtaaaacggggatgctaagattaactaatttccaaaaagagaa agatttaattcttctaggacaggctaaaaatggaaagtgtttcacataaaatgagacatagacaatataagtttgtc aaacattttgtgacgtcctaaaatagaaagtgtcctgagatggaggagaactacgttatctgttctcaaaaaagtgt gtatcatgtgatactatgtggatagtttagttcacatgttaacaattcatcatttatcagggaatatcttcctatgg gaggtagtgtcaacatgatcgaggagtcactgaagttagcctatggggagaactcagacttgataaaagataagcgc -continued attgcagcaattcaagctttatctgggactggagcatgccgaatttttgcagacttccaaaggcgcttttgtcctga ttcacagatttatattcctgttcctacatggtctaagtaagtgtattcttctgcttctcggcatctctacagcatcc taattgatcttcctcaattggtttttgcacattaaaacatgagtatgcaaataccttcaaaattttctaatttcctg tcattactaatataaaattcttggcagtcatcataacatttggagagatgctcatgtccctcagaaaacgtatcatt attatcatcctgaaacaaaggggttggacttcactgcactgatggatgatataaaggtaagaaaacatatatttgag gttgttttccatgatggtttgttctcctgtttgatgatatagcgtccctcctcaagtggcaattatgtgttctatcc tgacgtatttcaattttcattgacatagaatgccccaaatggatcattctttctgcttcatgcttgtgctcacaatc ctactggggtggatcctacagaggaacaatggagggagatctcgcaccacttcaaggtaatgattttgtatattttg tctctccttttcttgtaccaagtcatactaaatttattacactggttccaggtgaagggacattttgctttctttg acatggcctatcaaggatttgctagtgggaatccagagaaggatgctaaggcaatcaggatatttcttgaagatggt catccgataggatgtgcccaatcatatgcaaaaaatatgggactatatggccagagagttggttgcctaaggtaaac tactactcccaccatcatatcttatttgccctagttacaatctggagagtcaaactaactttttgttagaccttagt cggtctatttttcaaatgttctaattccaaaagcagttactactatttcctgtaaattctagattaattaactttt attatacctcattatcttcatttagtagctaattttaccatatatcatatttttcatattatcaatatgtagagaga attatttatttaaatatttaagtttatttataaaaaattgagttctttccgataacttcagttcatttccacctca aagtccaactcgacgtgaaaagcagaattttgctagtcaaaacttggatccaacaattatttagaataaattgagtt ctttccgataacttcagttcatttccacctcaaagtccaactcgacgagaaaaacagaattttgctagtcaaaactt ggatccaatgaaaagcaccaaaattttggttttaaattacaaaataatgtatactctaggtttttgtcctatgcaag tgattttacggtcttaaaataaagcatcaatcaatcccttaaacacacacaaagccctctaatacatttgctgagat gcttccgcaattcactgcagtgtggtttgtgaggatgaaaagcaagcagtggcagtgaaaagtcagttgcagcaact tgctaggcccatgtacagtaatccacctgttcatggtgcgctcgttgtttctaccatccttggagatccaaacttga aaaagctatggcttggggaagtgaaggtaatgtgattagaacgagataaagatttatgattgtataactatcattgg tattttgacgacagataggaactaggaaccttgctattaaagatatttcttgccttaattttgaaaaaagggaatt ttctcgctttttggaatgtatgagatttggatagaactatcacatggaaatgctgtaccattttctgctactcaca tggaaaagatccttttcttttgctgatctgtttaagcaccaatttgccatagctttgttgtcctatattttcagcca cagaaataagtctaaaccagtcccaagctttaataagctttcattgcgtggtagtgtcagccgcataaattggtcag tgcagccattaactgttttcttcatggggcctgttaaccttgtatttctccaaggtcaagttgttggtgttgtggct gctttttagctttgtactcattatcagagcatcatatgttaaacgtaaaggttcaatgactaagagttttttttcca gggcatggctgatcgcatcatcgggatgagaactgctttaagagaaaaccttgagaagaagggctcacctctatcgt gggagcacataaccaatcaggtattgaaatcaatgacttctgttgcgttctatactagtatataactattagaacac tatggctcacctattgccccattaatactcgatactgcctacagattggcatgttctgctatagtgggatgacaccc gaacaagttgaccgtttgacaaaagagtatcacatctacatgactcgtaatggtcgtatcaggtataatcactcatt cacgaatttctgcttaatgctccggtgttcttgtacgagttaatatctcattaatttttccactatgttatactgtg tgttttgtatgttgtgcagtatggcaggagttactactggaaatgttggttacttggcaaacgctattcatgaggtt accaaatcagcttaa SEQ ID NO: 8:
Deduced polypeptide sequence of NtAAT1-T as set forth in SEQ ID NO: 7
MAIRAAISGRSLKHISSSVGARSLSSLWRNVEPAPKDPILGVTEAFLADPTPHKVNVGVGAYRDDNGKPVVLECVRE

AERRIAGSFNMEYLPMGGSVNMIEESLKLAYGENSDLIKDKRIAAIQALSGTGACRIFADFQRRECPDSQIYIPVPT

WSNHHNIWRDAHVPQKTYHYYHPETKGLDFTALMDDIKNAPNGSFELLHACAHNPTGVDPTEEQWREISHHFKVKGH

FAFFDMAYQGFASGNPEKDAKAIRIFLEDGHPIGCAQSYAKNMGLYGQRVGCLSVVCEDEKQAVAVKSQLQQLARPM

-continued

YSNPPVHGALVVSTILGDPNLKKLWLGEVKGMADRIIGMRTALRENLEKKGSPLSWEHITNQIGMFCYSGMTPEQVD

RLTKEYHIYMTRNGRISMAGVTTGNVGYLANAIHEVTKSA

SEQ ID NO: 9: Nucleotide sequence of NtAAT3-S
atggcaaattcctccaattctgtttttgcgcatgttgttcgtgctcctgaagatcccatcttaggagtacgtccctt tccactctttctattttacatttccactgaatatgtttcttctgtggctcctttaataatcttccgtaaatatacta ttagtggatttgataagctacttctctctccctctctcttttattttcttattttgggttagattaaaatgaacatt aattaatgatcagatgatttggttaaagatgatatctaggagatcggcataaataagttgattggaatgatcgctat agggtttcctattgtatgcattggatcatggatgtgtgcgctaattatttaatagtacttctttctttttactgtga tctggcaattccttattttattcctggtgtagttgatgaaaggtgtagatttgattctttaacttgctctattgaga aggtaatttgtgcttctcaagtgtttattaatgttgttttcttctgttgtgttacttcattaaaacaggtcacagtt gcttataacaaagataccagcccagtgaagttgaatttgggtgttggcgcatatcgcactgaggtctgccacttcta ctttgtctcgttgttctttattattattatttttttattatagccaaaaaaagttgccccttgaatggatttggtcc tgctatgtgttgaatccttggttaagtttttctttaataggctccttcacaaggatagaaaattgtagacactgatg cttacacattagtaatatttttttcccctgatgcataatgaagtgaaaccacttgtgcttctaaaaaatcatactttg gggcaaggtgaagtacacatttttataagtggttgttttttttcttcaatcttgagttgaatgttagtgttaagtagg agccgcaaacgggcgggtcgggtcggatttggttcagatcgaaaatgggtaatgaaaaaacaggtaaattatctgac tcgacccatatttaatacggataaaaacaggttaaccggcggataatatgggtaaccatattattcatgtcttcttg catatgatcaattatgggagaattcttagcctcaaatgggaacccccaatttgaggctttacaaatttaaaagttag acccattggttaaccatttctaaatggataatatggttcttatccatatttgacccatttttaaaaagttcattat ccaacccatttttagtggataatatgggtgtttaactgatttcttttaaccattttgacacccctagtgttaagct tgaaaacgactaatgcatagtctgatgacaacttgcaggaaggaaagccccttgttcttaatgtggtgagacgggct gaacaaatgctcgtcaatgacacgtaacttgccaaattagaaactagcttacagattttcttttgagatatgatcac ctgataccaagattggaatctaaggctgctatgatgcaggtctcgggtgaaggagtatctctcaattactggactag cggattttaacaaactgagtgcaaagcttatatttggtgctgacaggtttggagatttttttggtgcagttgctcttg ataaatgcttgagtcaatttttttttaaaaaaaatgctcactatccatgtcgctctatttaaacctatcttgccaaac cacttgtataaatgaaaatgagccgtcgatattcttccttccatctagtttgatatttgaattagagattgttgcta aaagggaatgctttatctctacagcgtagagtaactgaatacctgttaaacatgttcctccgtatttcatcttatta tgatgccttgcatctgaagaaaattgttctagagttaactttctctcctctttgttgtactgattatctgtgtgtgg tgaacgcgatatcaggaaatatgtgtcttctgtcactattactccttgttaagtcatatgtaattgacttgttatga tatcaacagatttacttatgtttagatgtagtttaaatgctttttgtgctgttttgttgcttatacagccctgccat tcaagagaacagggtgactactgttcagtgcttgtcgggcacaggttctttgagggttggggctgaatttctggcta agcattatcatgaagttagtattccttgctctctttccctttatatgtctaaatcaaatggacacttgtataagctt ctactgtttgttttgttgccagcataccatatatataccacagccaacatggggaaaccatccgaaggttttcactt tagccgggctttcagtaaaatattaccgttactacgacccagcaacacgaggcctggatttccaaggtactactgta atcactgttcttaaagttctacagttgtaagtaagagccgatttctctttttttatggacaagtgaactttctcctgg tcgtgtctagaaagatctatattttatgtgtagctagcacaggatctttatttatttaattttgtattctcttggta aagatataagcatagtttatctgtggcttttcctgtatttgggtgttgcatatcaaatttaatcatgaaccctgtag gacttttggatgatcttgctgctgcacccgctggagcaatagttcttctccatgcatgtgctcataacccaactggc gttgatccaacaaatgaccagtgggagaaaatcaggcagttgatgaggtccaagggcctgttgcctttctttgacag tgcttaccaggtaaagcttatgatgggattttgaattcaagtgatacttcgttaagaatgattaccaaataatttga agcgccaaactatgtattaatgggctgcccaacggacccttactataatgaatatttttgatattgcaggttttgc -continued cagtggcaacctagatgcagatgcacaatctgttcgcatgtttgtggctgatggtggtgaatgtcttgcagctcaga gttatgccaaaaacatgggactgtatggggagcgtgttggtgcccttagcattgtaagtccttttgtcggttgtaat tgctttcccttttagtaagcgataaaattggtggctgaagaactatccatggctatatcatgctatctatgtctaa agatgattttccttgaaagcataattcaggttatattccctagaaggctaaaaagaagttgttctgatggtacaatg aacacagtctctagagatattgaaagccaaatttttgaatatggcttccccttgattgtaattggaaaacaaagag aaggacagagtggaattagtaccggattgtatgtttaggaaaaagtgtcattttgtttgagttttatcagacagaca ctaaaagctgactaacagtacaataaaattttgtgttgtgttataggtttgcaaagacgcagatgttgcaagcagag tcgaaagccagctaaagctggttatcaggccaatgtactctaatccaccaattcatggtgcgtctattgttgctact atactcaaggacaggtttgtgcaactatttacaagattctgttttgctgttagtagatgctataccttctacatttt gatgtggtttctcatctaatggtgatagacaaatgtacgatgaatggacaattgagctgaaagcaatggccgacagg attattagcatgcgccaacaactctttgatgccttgcaagctcgaggtatttgatcttcatatttgttctttctggg gaagcatactgtattctgtatgatgggtttgactgctactgcaataggagctttttcctgaaaagtaccatggtgaa acaaccacggcaactaaatcttttgacttcattgttcagtttagtgctaatgtaagttttattctgttatgcaggta cgacaggtgattggagtcatatcatcaagcaaattggaatgtttactttcacaggattaaatactgagcaagtttca ttcatgactagagagcatcacatttacatgacatctgatgggtaaggacatctgactattgatattttttttatttg tttagtttgttactttgggttgctttttttctcagtagaaacttaaataattggaacttagaagtccttcgttgatta tttcggcttgaattctttaataaggagaatttcagatttatagcttcagtttggagaggaagcataaacaagtctgt catccatacttaaaatttacagaaaaaaagtgcagttctgttttcccccctcccagattagactaattcccaaaagaa cttaccttcaatctatggaacatttagtattctggtatcagttgaaacatctctttgttgaagttaagattttggtt aaaaagatcttcatctctagtaacattttctacattccattttagaaggaatgattttctcctttctcatttgcag gagaattagcatggcaggccttagttctcgcacaattcctcatcttgccgatgccatacatgctgctgttaccaaag cggcctaa SEQ ID NO: 10:
Deduced polypeptide sequence of NtAAT3-S as set forth in SEQ ID NO: 9
MANSSNSVFAHVVRAPEDPILGVTVAYNKDTSPVKLNLGVGAYRTEEGKPLVLNVVRRAEQMLVNDTSRVKEYLSIT

GLADENKLSAKLIFGADSPAIQENRVTTVQCLSGTGSLRVGAEFLAKHYHEHTIYIPQPTWGNHPKVETLAGLSVKY

YRYYDPATRGLDFQGTTVITVLKVLQLYKHSLSVAFPVEGCCISNLIMNPVGLLDDLAAAPAGAIVLLHACAHNPTG

VDPTNDQWEKIRQLMRSKGLLPFEDSAYQGFASGNLDADAQSVRMEVADGGECLAAQSYAKNMGLYGERVGALSIVC

KDADVASRVESQLKLVIRPMYSNPPIHGASIVATILKDRQMYDEWTIELKAMADRIISMRQQLFDALQARGTTGDWS

HIIKQIGMFTFTGLNTEQVSFMTREHHIYMTSDGRISMAGLSSRTIPHLADAIHAAVTKAA

SEQ ID NO: 11: Nucleotide sequence of NtAAT3-T
atggcaaattcctccaattctgtttttgcccatgttgttcgtgctcctgaagatcccatcttaggagtacctccctt tccactctttctatttacatttccactgaatatgtttcttctgtggctcctttaataatcttccgtaaatatatta ttagtggatttgataagctacttctctctctctctctctctctctctctctctctctctctctctctctctcttt tattttcttattttgggttagattagaatgaacattaattaatgatcagatgattaggttaaaaatgatatcttgga gatcggcataaataagttgattggaatgatcgctatagggttacctattgtatgcattggatcatggatgtgtttac taattatttaatacctctttctttttactgtgatctggcaattccttattttattcctggtgtggttgatggaaggg tgtagatttgattctttaacttgctctattgagaagataatttgttcttctcaagtgtttagtaatggtttttttcc tgttgtgctacttcattaaaacaggtcacagttgcttataacaaagataccagcccggtgaagttgaatttgggtgt tggcgcatatcgcactgaggtctgccacttctactttgtctcgttattctttattttttatttttttattataaccaa aataagttgccccttgaatggatttggtcctgctatgttttgttgaatccttggttaagtttttctttaataggctc cttcacaaggatacaaaattgtagacactgatgcatacacattaatatttttttttccctgatgcataatgaagtgaa -continued accacttgattttataagtggttgtttttttcttcaatcttgagttggatgttagtgttaagcttgaaaattatgtt ctactaatgcatagtccgatgacaacttgcaggaaggaaagccccttgttcttaatgtggtgagacgagctgaacaa atgctcgtcaatgacacgtaacttgccaaattagaaactagcttacagattttcttttgagatatgatcacctgatg ccatgattggaatctaaggctgatatgatgcaggtctcgggtgaaggagtatctctcaattactggactagcggatt ttaacaaactgagtgcaaagcttatatttggatctgacaggtttggagaatttttggtgcagttgctcttgataaat gcttgaatcaaaaatataaaaaaatgctcactatccatgtcgctccagttaaacctatcttgccaaaccacttgtat aaaagaaaatgagccttcaatattcttccttccatctagtttgatatttgaatgagagattgttgctaaaagggaat gctttatctctacaaagtagagtaactgaatacctgttaaaacatattcctccgtatttcatcttattatgatgcct tgcatcagaagaaaattgttctagagttaactttctctcctctttgttgtactgactttctgtgtaaggtgaacgtg atatcaggaaatatgtgtcttctatcactattactccttgttaagtcatatgtaagatatcagcagatttacttatc tttagatgtagtttaaatgctttttgtgctgttttgttgctgatacagccctgccattcaagagaacagggtgacta ctgttcagtgcttgtcgggcacaggttctttgagggttggggctgagtttctggctaagcattatcatgaagttagt attccttgctctctttccctttatatgtctaaatcaaatggacacttctataagcttctactgtttgttttgttgcc agcatactatatatataccacagccaacatggggaaaccatccgaaggttttcactttagctgggctttcagtaaaa tattatcgttactacgacccagcaacacgaggcctggatttccaaggtactactgtaatcaatgttcttaaagttct acagttgtaagtaagaaccgatttctctttttcatggacaagtgaacttgctcctggtcgtgtctagaaagatctat atattatgtgtagctagcacaggatctttatttatttaattttgtattctgttggtaaagatataagcatagtttat ctgtggcttctcctgtatttgggtgttgcgtatcaaatttaatcatgaaccctgtaggacttttggatgatcttgct gctgcacccgctggagtaatagttcttctccatgcatgtgctcataacccaactggcgttgatccaacaaatgacca gtgggagaaaatcaggcagttgatgaggtccaaggggctgttacctttctttgacagtgcttaccaggtaaagctta tgatgggattttgaattcaagtgatacttcgttaagaatgattaccaaataatttgaagccccaaactatgtattaa tgggctgctcaatggacccctactataatgaatatttttgatattgcagggttttgccactggcaacctagatgcag atgcacaatctgttcgcatgtttgtggctgatggtggtgaatgtcttgcagctcagagttatgccaaaaacatggga ctgtatggggagcgtgttggtgcccttagcattgtaagtccttttgtcggttgtaattgctttcccttttttaataag caataaaattgctttccctttttaataagcaatatagcatgatatccatggctatatcatgctatttatgtctaaag atgatttttttctttggaagcataattcaggttatattccctaaaaggctaaaaagaggttgttctgttggtacaatg aacacagtctctagagatattgaaagccaatttttttgaagatggcttccacttagattgtaattggaaaagaaagag aaggacaaagtggaattagtaccggattgtatgtttaggaaaaagtgtcgtttttttttgagttttatcagacaggta ctaaaagctgactaacactacaataaaattttgtgttgtgttataggtttgcaaagatgcagatgttgcaagcagag tcgaaagccagctaaagctggttatcaggccaatgtactctaatccaccaattcatggtgcgtctattgttgctact atactcaaggacaggtttgtacaactatatacaagattctgttttgttgttagtagatgctataccttctacatttt gatgtggttgctcatctaatggtgatagacaaatgtacgatgaatggacaattgagctgaaagcaatggccgacagg attattagcatgcgccaacaactctttgatgccttgcaagctcgaggtatctgatcttcatatttgttctttctagg gaagcatactgtattctgtatgatgggtttgactgctactgcaataggaactttttctggaaaagtgccagggtgaa agaaccacggcaactaaatcttctgacttcattgttcagtttagtgctaatgtaagttttattctgttatgcaggta cagcaggtgattggagtcatatcatcaaacaaattggcatgtttactttcacaggattgaatactgagcaagtttca ttcatgactagagagcatcacatttacatgacatctgatgggtaaggacatctgactgttgatatttttttttattt gtttagtttgttactttgggttgctttttttctcagtagaaacttaaataattggaacttagaagcccttatcattga ttatttcggcttgaattctttaataaggagaatttcagacttatagcttcagttttgagaggaagcataaacaagtc cagctctgtcattcatacttaaaatttacagaagaaagtgcagttctgtttttccccccctcccaaattatattgatt ctcaaaagaacttaccttcaatctatggcacatttagtaatctggtatcagttgaaacatctctttgttgaagttaa -continued gattttggttaaaaagatcatcatctctagtgacattttctactttccatttttagaaggaatgattttctcctttc tcatttgcaggagaattagcatggcaggccttagttctcgcacaattcctcatcttgccgatgccatacatgctgct gttaccaaagcggcctaa SEQ ID NO: 12:
Deduced polypeptide sequence of NtAAT3-T as set forth in SEQ ID NO: 11
MANSSNSVFAHVVRAPEDPILGVTVAYNKDTSPVKLNLGVGAYRTEEGKPLVLNVVRRAEQMLVNDTSRVKEYLSIT

GLADFNKLSAKLIFGSDSPAIQENRVTTVQCLSGTGSLRVGAEFLAKHYHEHTIYIPQPTWGNHPKVFTLAGLSVKY

YRYYDPATRGLDFQGTTVINVLKVLQLYKHSLSVASPVFGCCVSNLIMNPVGLLDDLAAAPAGVIVLLHACAHNPTG

VDPTNDQWEKIRQLMRSKGLLPFFDSAYQGFATGNLDADAQSVRMFVADGGECLAAQSYAKNMGLYGERVGALSIVC

KDADVASRVESQLKLVIRPMYSNPPIHGASIVATILKDRQMYDEWTIELKAMADRIISMRQQLFDALQARGTAGDWS

HIIKQIGMFTFTGLNTEQVSFMTREHHIYMTSDGRISMAGLSSRTIPHLADAIHAAVTKAA

SEQ ID NO: 13: Nucleotide sequence of NtAAT4-S
atggtttccacaatgttctctctagcttctgccactccgtcagcttcattttccttgcaagataatctcaaggtaat ttcatcgtcaattacattatttggaaatttgccttatcttagactattcctaatgaggtggattcatgctgttgttt gtgtttgaacagtcaaagctaaagctggggactactagccaaagtgcctttttcgggaaagacttcgtgaaggcaaa ggtaggattttgtgttgtttgtgtacatttggtgagaggtaatagctctactgctatagagaaactccctgtaggt tctgtcctttagagtatagaagagaaggaaagagtttaattgggaataatggtggggatgggatgatttgcatacaa ttgaacatgtgtttcttgctttggtatattatgatataggatgatccaatcatgctccgtaaatcaactccagaact tattattctttcggcacttactaattataaaaatcgggttggagtcctgaaaataagtgattgcctaaccaacttac agaactaattttattatccgtatactcaaatcaaaacgacattatgccagtactggtttcttgagagggatgatatt agtgtagaattatttataaagttgcagtttaacgtagggtgttttactaaccagaaaggtgtagatgattccattca gtttattagatgctaagaagtataacagtgaggcctgtgaaacttctggtagtaccaacgattggggttttatggcg tttaggaatttagacattaattggcacattttagaacgaaaaatatgacatttaacttacaacagttcttttctgaa taaaatattactagtaactaatttgtttgaactttgccattgctaaaatgtggctcaagatcttcttggtacttcta tttgtaatatcagagttatagggggtctaattctagctcttgagtcgaaattgttattagtaaagataattctttctt gtccccccttcagtgctaacattctcatcttcacttatggtattggtttataaaaaattgtgattcagattataaagt aaaaaattatgcctcagtttgtacagcattttgggttatctgacgttcaattcaacagggttctttaatatctattt ttctatcttttgtaatcattgcaacaccgagctgtttaatgtgctcaaaggctattattagtcctcccactcaccag atccttagaaaaaagcccagaagagaaaggcaaagaatacaagcccagaccgattgctcgttttataaattttggga attgggatctcttttctcatattcttactttttctctttcttttttccagtcaaatggccgtactactatgactg ttgctgtgaacgtctctcgatttgagggaataactatggctcctcctgaccccattcttggagtttctgaagcattc aaggctgatacaaatgaactgaagcttaaccttggtgttggagcttaccgcacggaggagcttcaaccatatgtcct caatgttgttaagaaagtaagttcttggtctcttgtttatgctcaagtagtttgtaaacttttagtcacttggcctt gttcccatgggtggataccttgtccaaggggagtcaatttattacactctgtaaataggttaattctttttaaaa tgtatgtatgtatgtatgtatgtatgtatgtatacacacacactatgttgaatcgcccctggcttcttctgtttact tctatatattttgtatccaatgggtgaaaattctggagtgactgcttgttcctaagcgttcatcattcattaactgt tttaataaccttctataattttgcatctgaatgatgaggaaattgcttttctgtaggcagaaaaccttatgctagaa agaggagataacaaagaggtacttgatttactaaattcatcttttggccttgactagtgtcacttggtgccaattct tacttatttttaatctatggatatatagtatcttccaatagaaggtttggctgcattcaacaaagtcacagcagag ttattgtttggagcagataacccagtgattcagcaacaaagggtaagtatttttgtttttaactcttaggaaaatat atcctggaacaaacatgtaaatttggtctctatggcctttgttgtgaacgacgttgtacctttcgtgatcaggtggc tactattcaaggtctgtcaggaactgggtcattgcgtattgctgcagcactgatagagcgttacttccctggctcta -continued aggttttaatatcatctccaacctggggtacgtagatagtgcttttggattaatttggttgaatctcatgatactga tttttacagttatgttttgcaggaaatcataagaacattttcaatgatgccagggtgccttggtctgaatatcgata ttatgatcccaaaacagttggcctggattttgctgggatgatagaagatattaaggttattatcgtcctcgcatttg taatctttgtggttgaaattgtaaagcagcagtgagcactgtctttttcctttctccacaagtcaattgatggtgcc tttgtttgtggcacgtgttttgactttcagtaattgaaggagagatgcgttgttcattctagaatagcactgtatct cccaattgcattttctgtttcctgttcttcctccctatgtttgcattgatccatgtctctgctaaacatggacaatt tgcgcccttggcaatgacatgtgtgttgcttgcttttcttctctttctatttcttggtaggagtgacttggttcttt caatgtgagcagtcatatttctgaaaatgaaaatcagaggaacttgggatgtggaagggattggcagaacaagtttg ataatgtaatttttcttgtgaggatggaatatgcaaaaataggctgcacgcttgccttttagatctttggttcctat gtcggttgtgaatgtagatttctatttttcaacattgtctcgcaaggaaaataggattatccagtattggatgtctt tcctatgtttgatatgtgtatgtgcagtcttgtttgaccgtcttgctctcttcccacgtctaaaaagagagtctgat gggaaagtttttttccttccagttcttgtgcaagtcattgacatagtttatggcattacttgtttataggctgctcc tgaaggatcatttatcttgctccatggctgtgcgcacaacccaactggtattgatcccacaattgaacaatgggaaa agattgctgatgtaattcaggagaagaaccacattccatttttgatgtcgcctaccaggtaatctgtgctaaaccc aattatttcatttggtgaagctgtaaaatttcaagtttcttagaagttttgatggttgtgtgtgcgtgtgaagagaa tgaatgatataggaattggttttgaaatagtgaaagatctctcgtatttcatttgttcttttggtgtgaggagagta tacattgttgttttgatagatgggcaaattcgatagatgaaggtggttaagccacgtgttactttgtaattttttt tgacaccgtcatggtgtttatcaataaaatttactgatttttcagtaaagttattagaacaagataatctgaagtca tttctattcagagaattgcattgaatagctgtatactataataatcgagatgcctcatctgtctacacgctgcccta cagggatttgcaagcggcagccttgacgaagatgcctcatctgtgagattgtttgctgcacgtggcatggagctttt ggttgctcaatcatatagtaaaaatctgggtctgtatggagaaaggattggagctattaatgttctttgctcatccg ctgatgcagcgacaaggtacagtcacccgcactagcaactacataattgtcctctgtataggaaaaatgatgcactg gaaaacaatggttccatatgaaatgccaattacgagatgctgtccctttgctttgatattgtttactacaattggta tctcccatcacctgagcctatggcttgattggattttatgtgggcgaaccaatagaattatttgcttaattttctca actaatggatgcatctctgctaactcacagggtgaaaagccagctaaaaaggcttgctcgaccaatgtactcaaatc ccccaattcacggtgctagaattgttgccaatgtcgttggaattcctgagttctttgatgaatggaaacaagagatg gaaatgatggcaggaaggataaagagtgtgagacagaagctatacgatagcctctccaccaaggataagagtggaaa ggactggtcatacattttgaagcagattggaatgttctccttcacaggcctcaacaaagctcaggtaaatccccgtg atttaagctattgcttcatcacaatatgcttaaattcaatttgatcattcatcgcaaagcacattctgaactcagca catattttcattaacacattctttccgtcctttctgatcaattccataagtccgatatgcaaaagatagtgcagtga gagtctcttactggagtataactagattatcgacaatgcatacatttctttccctgtacctgcacttctggtgctca tatttgatctctcttcttggccacgcagagcgagaacatgaccaacaagtggcatgtgtacatgacaaaagacggga ggatatcgttggctggattatcagctgctaaatgcgaatatcttgcagatgccataattgactcgtactacaatgtc agctaa SEQ ID NO: 14:
Deduced polypeptide sequence of NtAAT4-S as set forth in SEQ ID NO: 13
MVSTMFSLASATPSASESLQDNLKSKLKLGTTSQSAFFGKDFVKAKSNGRTTMTVAVNVSRFEGITMAPPDPILGVS

EAFKADTNELKLNLGVGAYRTEELQPYVLNVVKKAENLMLERGDNKEYLPIEGLAAFNKVTAELLFGADNPVIQQQR

VATIQGLSGTGSLRIAAALIERYFPGSKVLISSPTWGNHKNIFNDARVPWSEYRYYDPKTVGLDFAGMIEDIKAAPE

GSFILLHGCAHNPTGIDPTIEQWEKIADVIQEKNHIPFFDVAYQGFASGSLDEDASSVRLFAARGMELLVAQSYSKN

LGLYGERIGAINVLCSSADAATRVKSQLKRLARPMYSNPPIHGARIVANVVGIPEFFDEWKQEMEMMAGRIKSVRQK

-continued

LYDSLSTKDKSGKDWSYILKQIGMFSFTGLNKAQSENMTNKWHVYMTKDGRISLAGLSAAKCEYLADAIIDSYYNVS

SEQ ID NO: 15: Nucleotide sequence of NtAAT4-T atggcttccacaatgttctctctagcttctgccgctccatcagcttcattttccttgcaagataatctcaaggtaat ttcattgtgaattacattatttggaaatttgccctatcttagactgttcctaatgaggtggattcatgctgttgttt gtgtttgaacagtcaaagctaaagctggggactactagccaaagtgcctttttcgggaaagacttcgcgaaggcaaa ggtaggattttgtgttgtttgtgtacatttggtgagaggtaatagctctactgatatagagcaactccctgtaggt tctgtcctttagagtatagaagagaagagaagagtttaattgggaataatggtggggatggaatgatttgcatacaa atgaacatgtgtttcttgcttttggtgtatgatataggatgatccaatcatgctccgtaaatcaactccagaactta ttattctttcggcacttctaattataaaaatctggttggagtaatgaatataagtgattacctaaccaacttacaga attgattttattatccatatactgaaattcaaaaacggcgttttgccagtactggtttcttgagagggatgatatta atatagaattattttataaagttgcagtttaacgtagggtattttactaactagaaaggtgatagatggttccgttc agtttattagaagtataacagtgaggcctgttaaacttttgctagtatcaatgattggggttttatggcgtttagga atttagacatcaattggcacattttagaacgaaaaacatgacatttaagttacatcagttcttttctgaataaaata gtactagtaaataacttgtttgaactttgccatttgctaaaatgtggctcaagatcttcttggtacttctatttgta atatcagagttataggggtctaattctaccactgttttgagtcaaaatgttattagtaaagataattctttcttgtc ccccttcagtgctaacattctcatcttcaattatggtattggtttataaaaaaattgtgcttcagatcactttataa agcaaaaattatgcctcagtttgtacagcattttgggttttataacattcaattcaacagggctctttaatatctat gtttctactttttgtaatctacatcgagctgtttaatgtgctcaaaggctttaattagtcctcctactcaccagatc cttagaaaaaagcccagaagagaaaggcaaagacaacgagctcggacagattgctcaatttatattgcaaaaagatc caaaccctcggggagggaggagcatgaaccaaagatgatacattgatattattttctaaatttgggaattgtgatct tatcttaaattttactttttctctttttctttttttatagtcaaatggtcggactactatggctgtttctgtgaa cgtctctcgatttgagggaataacaatggctcctcctgaccccattcttggagtttctgaagcattcaaggctgata caaatgaactgaagcttaaccttggagttggagcttaccgcacagaagatcttcaaccctatgtcctcaatgttgtt aaaaaagtaagtcctcggtctcttgtttatgctcaacgtagtttgtaaactaagagtcacttaaccttgttcccatg tgttcgtcattaaacatagtaataactttctatagttttgcatctgaatgatgaggaaattacttttctgtaggcag aaaaccttatgctagagagaggtgacaacaaagaggtacttgatatactaaattcatcttttggcctattagtgtct cttggtgccatttcttacttatttttgtccatgaatatatagtatcttccaatagaaggtttggctgcattcaaca aagtcacagcagagttattgtttggagcagataatccagtgattcagcaacaaagggtaagtattttggtttttaac tcttagcaaaaaagtatcctggaacaaacttgtagattcagtttccacggattgaatggcattgtatgtttcttgat caggtggctactattcaaggtctatcaggaactgggtcattgcgtattgctgcagcactgatagagcgttacttccc tggctctaaggttttgatatcatctccaacctggggtacgtatatagtgctttggattaatttggttgaatctcata atactgattttgcagttatgttttgcaggaaatcataagaacattttcaatgatgccagggtgccttggtctgaat atcgatattatgatcccaaaacagttggtctagattttgctgggatgatagaagatataaaggttattatcttcctc acttttgtaatctttgtggttgaaattgtaaagcagcagtgagcagtgtctttttcctttctccacaagtccattga tggtgcctttgcatgtgggacatgctttgactttcagtcgttgaaggagagatgcgttattcattctaggatagcat tgtatctcccaaatgctttttctgtttcctgctcttccttcccattttgcatcgatcctgtctctgctaaacatgg acaatttgcgcccttggcaaatggcaatgacttgtgtgttgcttttcttctctttctatttttggtaggagtgact tggttctttcagtgtgagcagtcatatttctgaaaatgaaaatcagaggaacttggtgctcacacttagagaaagtt tgttatgttttgggatgtgaaaggaattgacagaacaagtttgataatatatttttcttgtgaggatggaatatgc taaaaataggctgcactctttccttttagatctttagttcctatgtcggttgtgaatgtcgatttctattttcaaca ttttctcacgaagaaaataggattatccagtactggatgtctctcctatgtctgatatatgtgtatgtgcagtcttg -continued tttgcccgccttgctctctccccacgtctaaaaacagagtctgatggaaaaggctttttccttccagcttttgtgta agtcattgacatagtttaatgaaactacttgtttataggctgctcctgaaggatcattcatcttgctccatggctgt gcacacaacccaactggtattgatcccacaattgaacaatgggaaaagattgctgatgtaattcaggagaagaacca cattccatttttttgatgttgcctaccaggtaatctgtgctaaacccaattattttcatttggtgaagttgtagaatt ccaagtttcttagaagttttgatggctgtgtgtgcgtgtgtgaaaagaatgaaagatataggagatggtttcaaaat agtgaaagatctctcgtatttcatttgtcttttggtgtgtggagactatacattgttgtattgatagatgagcgaat ttgattgatgttggtggttaagccacatgtgttactttgtccatattttttttacaccgtcttggtttttatcaatga aatttactgatttttcagtgaaattattagaacaagatcatctgaagtcatttctgttcagagaattggattgaata gctgtatactataataatcgagatgcctcatctgtctacacgctgcactgcagggattcgcaagcggcagccttgat gaagatgcctcatctgtgagattgtttgctgcacgtggcatggagcttttggttgctcaatcatatagtaaaaatct gggtctgtatggagaaaggattggagctattaatgttctttgctcatctgctgatgcagcgacaaggtacaacggcc agcactaataatctacatatttctcctctgtattggtaaaatgatgttgcactgaagattttggttaatgtatgatg ccatttatttatgttatgcatgtgcagttctttccgtgtatgatttgttatacaatatagcaagatgagatgcttta atctcctttggattttatgtggttgaaccaatataacttttcttctgttaatggatgcatatctactaacttacagg gtgaaaagccagctaaaaaggcttgctcgaccaatgtactcaaatccccccattcacggtgctagaattgttgccaa tgtcgttggaattcctgagttctttgatgaatggaaacaagagatggaaatgatggcaggaaggataaagagtgtga gacagaagctatatgatagcctctccgccaaggataaaagtggaaaggactggtcatacattctgaagcagattgga atgttctccttcacaggcctcaacaaagctcaggtaaaaccccgtgaattaagttattgctgttgcggaagccaaat atatagagagtgattaaatcacaactactatatctaaaggtagctangtaaatgagacaataataaaatgaacacca gaaattaatgaggttcggcaaaatttgattttttgcctagttctcggacacaatcaactcaaatttatttcactcca aaaatacaaatgaaatactacaagagagaaagaagattcaaatgccttaggaaataagaaggcaagtgagagatgtt tacaaatgaacaaaatccttgctatttatagaagagaaatggccttaataatgtcatgcatgacatcatattaagtg tgaacatgtaatgtaaatgcacgaaaaatgcatctaccaatttcttaaggcttcaaatgttcacactagttcacatt aatcttgtcaaaattcaacaattgctgcatcacaatatgcttaaattcaatttgatttggttgacaactttctagct ttgatcattcatcacaaagcgcattcttcactcagcacgtatttttattaagacattctttccttccattctgaccg atttcataagttaaatatgcaaaagatagtgcagtgagagtctccttactggattataactatggactaaagttaaa tgcatacatttctttccctgtacttgcacttctcgtgctcatatttgatatctcttcttggctacacagagcgagaa catgaccaacaagtggcatgtgtacatgacaaaagacgggaggatatcgttggctggattatctgctgccaaatgtg aatatcttgcagatgccataattgactcatactacaatgtcagctaa SEQ ID NO: 16:
Deduced polypeptide sequence of NtAAT4-T as set forth in SEQ ID NO: 15
MASTMFSLASAAPSASESLQDNLKSKLKLGTTSQSAFFGKDFAKAKSNGRTTMAVSVNVSRFEGITMAPPDPILGVS

EAFKADTNELKLNLGVGAYRTEDLQPYVLNVVKKAENLMLERGDNKEYLPIEGLAAFNKVTAELLFGADNPVIQQQR

VATIQGLSGTGSLRIAAALIERYFPGSKVLISSPTWGNHKNIFNDARVPWSEYRYYDPKTVGLDFAGMIEDIKAAPE

GSFILLHGCAHNPTGIDPTIEQWEKIADVIQEKNHIPFFDVAYQGFASGSLDEDASSVRLFAARGMELLVAQSYSKN

LGLYGERIGAINVLCSSADAATRVKSQLKRLARPMYSNPPIHGARIVANVVGIPEFFDEWKQEMEMMAGRIKSVRQK

LYDSLSAKDKSGKDWSYILKQIGMFSFTGLNKAQSENMTNKWHVYMTKDGRISLAGLSAAKCEYLADAIIDSYYNVS

SEQ ID NO: 17: Nucleotide sequence used to generate AAT2S/T RNAi plants
gctattcaagagaacagagtaacaactgtgcagtgcttgtctggcacaggctcattgagggttggagctgaattttt ggctcgacattatcatcaacgcac

The invention claimed is:

1. Cured *Nicotiana tabacum* plant material, or cured *Nicotiana tabacum* homogenized plant material, obtained from a *Nicotiana tabacum* plant or part thereof, the plant or part thereof comprising a *Nicotiana tabacum* plant cell, wherein the plant cell comprises:

a non-naturally occurring interference polynucleotide comprising a sequence having at least 90% sequence identity to at least 19 contiguous nucleotides of SEQ ID NO: 17;

wherein the interference polynucleotide decreases the expression of a *Nicotiana tabacum* aspartate transaminase 2-S (NtAAT2-S) polynucleotide having SEQ ID NO: 1 and a *Nicotiana tabacum* aspartate transaminase 2-T (NtAAT2-T) polynucleotide having SEQ ID NO: 3 in the plant cell as compared to a control plant cell without the interference polynucleotide, and wherein the amount of aspartate and/or ammonia is reduced in the *Nicotiana tabacum* plant material as compared to the amount of aspartate and/or ammonia in control *Nicotiana tabacum* plant material.

2. A tobacco product comprising cured *Nicotiana tabacum* plant material or cured homogenized *Nicotiana tabacum* plant material according to claim 1.

3. A method for producing cured *Nicotiana tabacum* plant material with a decreased amount of aspartate and/or a decreased amount of ammonia as compared to control *Nicotiana tabacum* plant material, comprising the steps of:

(a) providing a *Nicotiana tabacum* plant or part thereof, wherein the *Nicotiana tabacum* plant or part thereof comprises a *Nicotiana tabacum* plant cell comprising a non-naturally occurring interference polynucleotide comprising a sequence that has at least 90% sequence identity to at least 19 contiguous nucleotides of SEQ ID NO: 17; and wherein the interference polynucleotide decreases the expression of an NtAAT2-S polynucleotide having SEQ ID NO: 1 and an NtAAT2-T polynucleotide having SEQ ID NO: 3 in the plant cell as compared to a control *Nicotiana tabacum* plant cell without the interference polynucleotide;

(b) harvesting *Nicotiana tabacum* plant material therefrom; and (c) curing the *Nicotiana tabacum* plant material;

thereby producing cured *Nicotiana tabacum* plant material with a decreased amount of aspartate and/or a decreased amount of ammonia as compared to control *Nicotiana tabacum* plant material.

4. The cured *Nicotiana tabacum* plant material of claim 1, wherein the *Nicotiana tabacum* plant material is air-cured, sun-cured or flue-cured plant material.

5. The cured *Nicotiana tabacum* plant material of claim 1, wherein the *Nicotiana tabacum* plant material comprises biomass, seed, stem, flowers, or leaves which comprise the plant cell.

6. The method of claim 3, wherein the cured *Nicotiana tabacum* plant material (c) comprises cured leaves, cured stems, cured flowers, or a mixture thereof.

7. The method of claim 3, wherein curing the *Nicotiana tabacum* plant material (c) comprises air curing, fire curing, smoke curing, or flue curing the plant material.

* * * * *